(12) United States Patent
Defrees et al.

(10) Patent No.: US 7,888,331 B2
(45) Date of Patent: *Feb. 15, 2011

(54) GANGLIOSIDE COMPOSITIONS AND METHODS OF USE

(75) Inventors: Shawn A. Defrees, North Wales, PA (US); Karl Frank Johnson, Hatboro, PA (US); Zhi-Guang Wang, Dresher, PA (US)

(73) Assignee: Seneb Biosciences, Inc., North Wales, PA (US)

( * ) Notice: Subject to any disclaimer, the term of this patent is extended or adjusted under 35 U.S.C. 154(b) by 516 days.

This patent is subject to a terminal disclaimer.

(21) Appl. No.: 10/547,566

(22) PCT Filed: Mar. 4, 2004

(86) PCT No.: PCT/US2004/006904

§ 371 (c)(1),
(2), (4) Date: Jun. 15, 2007

(87) PCT Pub. No.: WO2004/080960

PCT Pub. Date: Sep. 23, 2004

(65) Prior Publication Data

US 2007/0275908 A1 Nov. 29, 2007

Related U.S. Application Data

(60) Provisional application No. 60/452,796, filed on Mar. 6, 2003.

(51) Int. Cl.
  A61K 31/706 (2006.01)
  C07H 15/10 (2006.01)
  C07H 15/26 (2006.01)

(52) U.S. Cl. .................................. 514/53; 536/1.11

(58) Field of Classification Search ............ 514/53; 536/1.11

See application file for complete search history.

(56) References Cited

U.S. PATENT DOCUMENTS

| | | | | |
|---|---|---|---|---|
| 4,940,694 A | * | 7/1990 | della Valle et al. | 514/25 |
| 5,264,424 A | * | 11/1993 | Della Valle et al. | 514/54 |
| 6,440,703 B1 | * | 8/2002 | DeFrees | 435/84 |
| 7,273,852 B2 | * | 9/2007 | Tsuji et al. | 514/23 |
| 2002/0072502 A1 | | 6/2002 | Ho | |

FOREIGN PATENT DOCUMENTS

| | | |
|---|---|---|
| DE | 19733255 A1 | 2/1999 |
| EP | 0577580 * | 1/1994 |
| WO | WO 03/017949 A2 | 3/2003 |

OTHER PUBLICATIONS

Helling, F. et al, Cancer Research, 1994, 54, 197-203.*
The Merck Manual,16th edition, 1992, pp. 2657, 1466-1471,1464-1465, 1518-1519.*
Allen et al, J. Am. Chem. Soc., 2001, 123, 1890-1897.*
Helling, Friedhalm, et al.; "$G_{D3}$ Vaccines for Melanoma: Superior Immunogenicity of Keyhole Limpet Hemocyanin Conjugate Vaccines"; *Cancer Research*; Jan. 1, 1994; pp. 197-203; vol. 54.

* cited by examiner

*Primary Examiner*—Shaojia Anna Jiang
*Assistant Examiner*—Ganapathy Krishnan
(74) *Attorney, Agent, or Firm*—Morgan, Lewis & Bockis, LLP

(57) ABSTRACT

Novel synthetic glycosphingolipids and pharmaceutical compositions containing such synthetic glycosphingolipids are described. Methods of making the novel synthetic glycosphingolipid compounds and compositions as well as their use in the field of neuroprotection and cancer treatment is also described.

10 Claims, 37 Drawing Sheets

GANGLIOSIDE COMPOSITIONS AND METHODS OF USE

CROSS REFERENCE TO RELATED APPLICATIONS

This application is related to PCT/US02/27935, filed on Aug. 29, 2002 which is herein incorporated in its entirety by reference.

FIELD OF THE INVENTION

This invention pertains to novel glycosphingolipids and methods of preparing and using them.

BACKGROUND

Glycosphingolipids are a class of lipid that having a carbohydrate moiety linked to a ceramide. An exemplary class of glycosphingolipid is the gangliosides. The carbohydrate moiety includes at least one sialic acid moiety. Gangliosides typically include saccharide moieties in addition to the sialic acid moiety and are classified according to the number of monosaccharides and sialic acid groups present in the structure. Gangliosides are known as mono-, di-, tri- or poly-sialogangliosides, depending upon the number of sialic acid residues. Abbreviations employed to identify these molecules include "GM1", "GD3", "GT1", etc., with the "G" standing for ganglioside, "M", "D" or "T", etc. referring to the number of sialic acid residues, and the number or number plus letter (e.g., "GT1a"), referring to the elution order in a TLC assay observed for the molecule. See, Lehninger, Biochemistry, p. 294-296 (Worth Publishers, 1981); Wiegandt, Glycolipids: New Comprehensive Biochemistry (Neuberger et al., ed., Elsevier, 1985), pp. 199-260.

For example, the international symbol $GM_{1a}$ designates one of the more common gangliosides, which has been extensively studied. The "M" in the symbol indicates that the ganglioside is a monosialoganglioside and "1" defines its position in a TLC elution profile. The subscripts "a", "b" or "c" also indicate the positions in a TLC assay of the particular ganglioside. The terminal saccharide is the saccharide, which is located at the end of the carbohydrate moiety, which is opposite to the end that is attached to the ceramide moiety.

The term "glycosphingolipids" (GSLS) refers to a genus that encompasses six classes of compounds, five of which are derived from glucosylceramide (GlcCer), which is enzymatically formed from ceramide and UDP-glucose. The enzyme involved in GlcCer formation is UDP-glucose:N-acylsphingosine glucosyltransferase (GlcCer synthase). The rate of GlcCer formation under physiological conditions may depend on the tissue level of UDP-glucose, which in turn depends on the level of glucose in a particular tissue (Zador, I. Z. et al., *J. Clin. Invest.* 91: 797-803 (1993)). In vitro assays based on endogenous ceramide yield lower synthetic rates than mixtures containing added ceramide, suggesting that tissue levels of ceramide are also normally rate-limiting (Brenkert, A. et al., *Brain Res.* 36: 183-193 (1972)).

The level of GSLs controls a variety of cell functions, such as growth, differentiation, adhesion between cells or adhesion between cells and matrix proteins, binding of microorganisms and viruses to cells, and metastasis of tumor cells. In addition, the GlcCer precursor, ceramide, may cause differentiation or inhibition of cell growth (Bielawska, A. et al., *FEBS Letters* 307: 211-214 (1992)) and be involved in the functioning of vitamin $D_3$, tumor necrosis factor-$\alpha$, interleukins, and apoptosis (programmed cell death). The sphingols (sphingoid bases), precursors of ceramide, and products of ceramide catabolism, have also been shown to influence many cell systems, possibly by inhibiting protein kinase C(PKC).

A class of glycosphingolipids, the gangliosides are known to be functionally important in the nervous system and it has been demonstrated that gangliosides are useful in the therapy of peripheral nervous system disorders. Numerous gangliosides and derivatives thereof have been used to treat a wide variety of nervous system disorders including Parkinson's disease. Ganglioside $GM_1$, is currently being used in phase II clinical development for the treatment of Parkinson's Disease and cerebral ischemic strokes (see, U.S. Pat. Nos. 4,940,694; 4,937,232; and 4,716,223). Gangliosides have also been used to affect the activity of phagocytes (U.S. Pat. No. 4,831,021) and to treat gastrointestinal disease-producing organisms (U.S. Pat. No. 4,762,822). The gangliosides $GM_2$ and $GD_2$, purified from animal brain, have been conjugated to keyhole limpet hemacyanin (KLH) and mixed with adjuvant QS21, and used to elicit immune responses to these gangliosides, as the basis of a cancer vaccine in phase II and III trials (Progenics, Tarrytown, N.Y.). Ganglioside $GM_3$ is being investigated for use as an anti-cancer agent (WO 98/52577; Nole et al., *Exp. Neurology* 168: 300-9 (2001)). Glycolipids are also of interest in the treatment of inflammatory bowel disease. See, Tubaro et al., *Naunyx-Schmiedebergg's Arch. Pharmacol.* 348: 670-678 (1993).

Gangliosides are generally isolated via purification from tissue, particularly from animal brain (GLYCOLIPID METHODOLOGY, Lloyd A. Witting Ed., American Oil Chemists Society, Champaign, Ill. 187-214 (1976); U.S. Pat. Nos. 5,844,104; 5,532,141; Sonnino et al., *J. Lipid Res.* 33: 1221-1226 (1992); Sonnino et al., *Ind. J. Biochem. Biophys.*, 25: 144-149 (1988); Svennerhohn, *Adv. Exp. Med. Biol.* 125: 533-44 (1980)). Gangliosides have also been isolated from bovine buttermilk (Ren et al., *J. Bio. Chem.* 267: 12632-12638 (1992); Takamizawa et al., *J. Bio. Chem.* 261: 5625-5630(1986)). Even under optimum conditions, the yields of pure gangliosides, e.g., GM2 and GM3, are vanishingly small. Moreover, purification from mammalian tissue carries with it the risk of transmitting contaminants such as viruses, prion particles, and so forth. Alternate methodologies for securing gangliosides are thus highly desirable.

Despite the many advantages of naturally occurring gangliosides, there is a need for ganglioside analogues that have characteristics, e.g., bioavailability, target specificity, activity, etc. that are enhanced relative to naturally occurring gangliosides. Furthermore, ganglioside analogues, synthetically prepared from sphingosine and sphingosine analogues, are free of the risk of transmission of animal disease, such as bovine spongiform encephalitis.

Due to the importance of gangliosides, efforts have been expended to develop methods of synthesizing pure gangliosides in high yields. Methods of chemically synthesizing gangliosides are described in Hasegawa et al., *J. Carbohydrate Chemistry*, 11(6): 699-714 (1992) and Sugimoto et al., *Carbohydrate Research*, 156: C1-C5 (1986). U.S. Pat. No. 4,918,170 discloses the synthesis of GM3 and GM4. Schmidt et al. describe the chemical synthesis of GM3 (U.S. Pat. No. 5,977,329). The references describe multi-step synthetic procedures using laborious protection-activation-coupling-deprotection strategies, at each step of which the intermediate is purified, generally by a combination of extraction and column chromatography. Moreover, none of the synthetic methods is appropriate for the large-scale preparation of gangliosides.

In view of the difficulties associated with the chemical synthesis of carbohydrates, the use of enzymes to synthesize the carbohydrate portions of gangliosides is a promising approach to preparing gangliosides. Enzyme-based syntheses have the advantages of regioselectivity and stereoselectivity. Moreover, enzymatic syntheses can be performed using unprotected substrates. Two principal classes of enzymes are used in the synthesis of carbohydrates, glycosyltransferases (e.g., sialyltransferases, galactosyltransferases), and glycosidases. The glycosidases are further classified as exoglycosidases (e.g., β-galactosidase, β-glucosidase), and endoglycosidases (e.g., endoglycoceramidase). Each of these classes of enzymes has been successfully used to prepare carbohydrates. For a general review, see, Crout et al., *Curr. Opin. Chem. Biol.* 2: 98-111 (1998) and Arsequell, supra.

Glycosyltransferases have been used to prepare oligosaccharides, and have been shown to be effective for producing specific products with good stereochemical and regiochemical control. For example, β-1,4-galactosyltransferase was used to synthesize lactosamnine, illustrating the utility of glycosyltransferases in the synthesis of carbohydrates (see, e.g., Wong et al., *J. Org. Chem.* 47: 5416-5418 (1982)). Moreover, numerous synthetic procedures have made use of α-sialyltransferases to transfer sialic acid from cytidine-5'-monophospho-N-acetylneuraminic acid to the 3-OH or 6-OH of galactose (see, e.g., Kevin et al., *Chem. Eur. J.* 2: 1359-1362 (1996)). For a discussion of recent advances in glycoconjugate synthesis for therapeutic use, see, Koeller et al., *Nature Biotechnology* 18: 835-841 (2000).

Glycosidases normally catalyze the hydrolysis of a glycosidic bond, however, under appropriate conditions they can be used to form this linkage. Most glycosidases used for carbohydrate synthesis are exoglycosidases; the glycosyl transfer occurs at the non-reducing terminus of the substrate. The glycosidase takes up a glycosyl donor in a glycosyl-enzyme intermediate that is either intercepted by water to give the hydrolysis product, or by an acceptor, to give a new glycoside or oligosaccharide.

In addition to the need for an array of synthetic ganglioside analogues having improved therapeutic properties, there remains a need for a simple, high-yielding procedure to prepare the synthetic ganglioside analogues. Since the biological activity of a ganglioside or a synthetic analogue thereof generally depends upon the presence of a particular glycoform, or the absence of a particular glycoform, a need exists for an in vitro procedure to enzymatically prepare a ganglioside analogue with a pre-selected glycosylation pattern, particularly on substrates such as ceramide, sphingosine and their analogues. The present invention is directed to addressing these, and other needs.

SUMMARY OF THE INVENTION

Glycolipids are of general use for treating an array of disorders. The present invention is illustrated by reference to gangliosides, an exemplary class of glycolipid. Gangliosides are of interest as agents to treat neurological diseases and autoimmune disorders. Currently available treatment methods employing gangliosides are, however, inadequate. Generally gangliosides used for therapeutic purposes have been purified by time consuming techniques from biological media, such as bovine brains, resulting in potentially impure preparations. Furthermore, the gangliosides generally require intravenous administration because of insufficient absorption by the intestinal tract. Additionally, the currently available gangliosides exhibit minimal penetration through the blood brain barrier.

Thus, currently available gangliosides generally cannot be readily prepared, nor can they be conveniently administered to subjects to halt the progression, reduce the severity and/or treat neurological and autoimmune diseases and to promote neuritogenesis and neurogenesis. The present invention recognizes the need to develop new, improved and effective gangliosides for the treatment of neurological and autoimmune disease.

The present invention addresses the present deficiencies in the art by providing a class of ganglioside derivatives having the general formula:

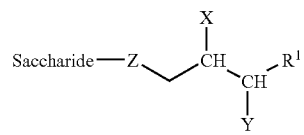

wherein, the symbol Z represents a member selected from O, S, $C(R^2)_2$ and $NR^2$. X is a member selected from H, $-OR^3$, $-NR^3R^4$, $-SR^3$, and $-CHR^3R^4$. The symbols $R^1$, $R^2$ and $R^3$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, $-C(=M)R^5$, $-C(=M)-Z-R^5$, $-SO_2R^5$, and $-SO_3$, in which the symbols M and Z represent members independently selected from O, $NR^6$ or S.

The symbol Y represents H, $-OR^7$, $-SR^7$, $-NR^7R^8$, substituted or unsubstituted alkyl, substituted or unsubstituted heteroalkyl, substituted or unsubstituted aryl, substituted or unsubstituted heteroaryl, or substituted or unsubstituted heterocycloalkyl. $R^5$, $R^6$, $R^7$ and $R^8$ are members independently selected from H, substituted or unsubstituted alkyl, substituted or unsubstituted heteroalkyl, substituted or unsubstituted aryl, substituted or unsubstituted heteroaryl, and substituted or unsubstituted heterocycloalkyl.

The invention also provides pharmaceutical compositions incorporating the compounds of the invention and methods of using the compounds of the invention in therapy and diagnosis. For example, in an exemplary embodiment, there is provided a method for the prevention or treatment of a disorder of the nervous system in a subject. The method includes administering to the subject in need thereof a therapeutically effective amount of a compound of the invention. The treatment of specific disorders of the nervous system is discussed in greater detail herein.

In another embodiment, the invention provides a method of preparing a ganglioside of the invention using enzymatically-catalyzed processes to add the glycosyl subunits of the ganglioside.

Other aspects, objects, and advantages of the present invention will be apparent to those of skill in the art from the detailed description that follows.

DETAILED DESCRIPTION OF THE INVENTION AND THE PREFERRED EMBODIMENTS

Abbreviations

Figure 1:
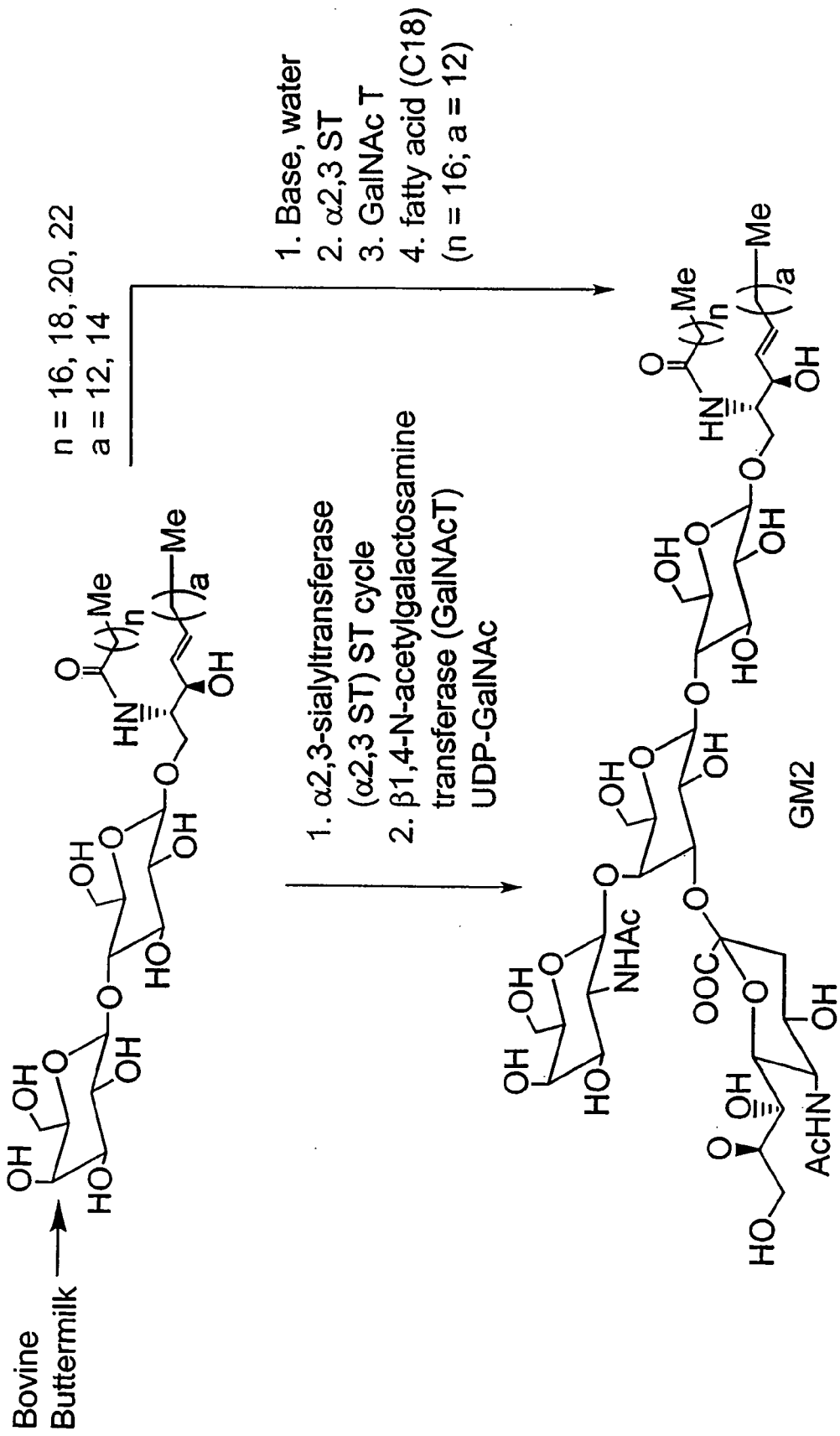
FIG. 1 is a schematic diagram of two methods for synthesis of the ganglioside GM2 by enzymatic synthesis using as the starting material lactosylceramide obtained from bovine buttermilk.

Abrreviations of saccharide moieties refer to both substituted and unsubstituted analogues of the saccharides. Thus, arabinosyl; Fru, fructosyl; Fuc, fucosyl; Gal, galactosyl; GalNAc, N-acetylgalactosyl; Glc, glucosyl; GlcNAc, N-acetylglucosyl; Man, mannosyl; ManAc, mannosyl acetate; Xyl, xylosyl; and Sia and NeuAc, sialyl (N-acetylneuraminyl and derivatives thereof). The abbreviations are intended to encompass both unmodified saccharyl moieties and substituted or other analogues thereof.

Definitions

Unless defined otherwise, all technical and scientific terms used herein generally have the same meaning as commonly understood by one of ordinary skill in the art to which this invention belongs. Generally, the nomenclature used herein and the laboratory procedures in molecular biology, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see genierally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those known and employed in the art. Standard techniques, or modifications thereof, are used for chemical syntheses and chemical analyses.

"Glycosphingolipid analogue" and "glycosphingolipid" are used herein to refer to the compounds of the invention. The terms are used to refer to glycosphingolipid structures in which the saccharyl moiety, the base (e.g., sphingoid-like backbone), or the fatty acid-derived hydrocarbon is of a structure other than that found in naturally occurring glycosphingolipids.

"Saccharide" and "saccharyl" refer to a moiety that includes a substituted or unsubstituted heteroalkyl group that exists in at least one cyclic conformation. Moieties according to this definition will generally have at least one reducing terminus.

"Peptide" refers to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Amino acids that are not gene-encoded may also be used in the present invention. Furthermore, amino acids that have been modified to include reactive groups may also be used in the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

As used herein, "nucleic acid" means DNA, RNA, single-stranded, double-stranded, or more highly aggregated hybridization motifs, and any chemical modifications thereof Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids, phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Modifications can also include 3' and 5' modifications such as capping with a PL, a fluorophore or another moiety.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

An "acceptor moiety" for a glycosyltransferase is a saccharide structure that act as an acceptor of a saccharyl group that is a substrate for the glycosyltransferase. When the acceptor moiety is contacted with the corresponding glycosyltransferase, sugar donor moiety, and other necessary reaction mixture components, and the reaction mixture is incubated for a sufficient period of time, the glycosyltransferase transfers sugar residues from the sugar donor moiety to the acceptor moiety. The acceptor moiety will often vary for different types of a particular glycosyltransferase. For example, the acceptor moiety for a mammalian galactoside 2-L-galactosyltransferase will include a Galβ1,4-Glc-R at a non-reducing terminus of a saccharide. Accordingly, the term "acceptor moiety" is taken in context with the particular glycosyltransferase of interest for a particular application. Acceptor moieties for other glycosyltransferases are described herein.

The term "sialic acid" refers to any member of a family of nine-carbon carboxylated sugars. Also included are sialic acid analogues that are derivatized with linkers, reactive functional groups, detectable labels, components for inclusion into lipid rafts and targeting moieties. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, N.Y. (1992)). The synthesis and use of sialic acid compounds in a sialylation procedure is disclosed in international application WO 92/16640, published Oct. 1, 1992.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. A "recombinant polypeptide" is one that has been produced by a recombinant cell. The present invention optionally makes use of enzymes and/or substrates that are expressed by a cell that includes a recombinant protein.

The term "isolated" refers to a material that is substantially or essentially free from components, which are used to produce the material. For compositions produced by a method of the invention, the term "isolated" refers to material that is substantially or essentially free from components, which normally accompany the material in the mixture used to prepare the composition. "Isolated" and "pure" are used interchangeably. Typically, isolated compounds produced by the method of the invention have a level of purity preferably expressed as a range. The lower end of the range of purity for the glycosphingolipid compounds is about 60%, about 70% or about 80% and the upper end of the range of purity is about 70%, about 80%, about 90% or more than about 90%.

When the compounds produced by a method of the invention are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of compounds produced by a method of the invention in which a selected percentage of the glycosyl donor added to a precursor substrate are added to identical acceptor sites on the individual members of a population of substrate. "Essentially each member of the population" speaks to the "homogeneity" of the sites on the substrate that are conjugated to a glycosyl donor and refers to compounds of the invention, which are at least about 80%, preferably at least about 90% and more preferably at least about 95% homogenous.

"Homogeneity," refers to the structural consistency across a population of acceptor moieties to which the glycosyl donors are conjugated. Thus, if at the end of a glycosylation reaction, each glycosyl donor transferred during the reaction is conjugated to an acceptor site having the same structure, the composition is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the compositions prepared by a method of the invention are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the glycosphingolipids is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

Oligosaccharides described herein are generally described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). Each saccharide is preferably a pyranose. For a review of standard glycobiology nomenclature see, *Essentials of Glycobiology* Varki et al. eds. CSHL Press (1999).

As used herein, "linking member" refers to a covalent chemical bond that includes at least one heteroatom. Exemplary linking members include —C(O)NH—, —C(O)O—, —NH—, —S—, —O—, and the like.

The symbol ∼∼ , whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Fumiss et al. (eds.), VOGEL'S ENCYCLOPEDIA OF PRACTICAL ORGANIC CHEMISTRY $5^{TH}$ED., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "alyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropyhnethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl," and "alkylene." Alkyl groups, which are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from about 1 to about 40 carbon atoms, with those groups having 30 or fewer carbon atoms being preferred in the present invention.

A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR=R")=NR''', —S(O)R', —S(O)$_2$R', —S(O)$_2$NR'R", —NRSO$_2$R', —CN and —$NO_2$ in a number ranging from zero to (2 m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R''', —OC(O)R', —C(O)R', —$CO_2$R', —CONR'R", —OC(O)NR'R", —NR"C(O)R', —NR'—C(O)NR"R''', —NR"C(O)$_2$R', —NR—C(NR'R"R''')=NR'''', —NR—CR'R")=NR''', —S(O)R', —S(O)$_2$R', —S(O)$_2$NR'R", —NRSO$_2$R', —CN and —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 40. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 40. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 40, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_{40}$)alkyl.

As used herein, the term "heteroatom" is meant to include oxygen (O), nitrogen (N), sulfur (S) and silicon (Si).

The term "glycosyltransferase" as used herein refers to enzymes that catalyze the transfer of sugar moieties from activated donor molecules to specific acceptor molecules, each as defined herein, forming glycosidic bonds. Examples of glycosyltransferases include, but are not limited to, galactosyltransferase, glucosyltransferase, fucosyltransferase, and GalNActransferase. Further, glycosyltransferases may be classified according to the stereochemistries of the reaction substrates and products as either retaining, i.e., leading to retention of the anomeric configuration (for instance UDP-glucose->α-glucoside), or inverting, i.e., leading to inversion of the anomeric configuration (for instance UDP-glucose->β-glucoside) (Sinnott, M. L. (1990) Chem. Rev. 90, 1171-1202). The classification groupings of families of glycosyltransferases is explained by Coutinho, P. M. & Henrissat, B. (1999) Carbohydrate-Active Enzymes server, which can be found on the Internet at <<afmb.cnrs-mrs.fr/~pedro/CAZY/db.html>>.

As used herein, the term "trans-sialidase", refers to an enzyme that catalyzes the addition of a sialic acid to galactose through an α-2,3 glycosidic linkage. Trans-sialidases are found in many Trypanosome species and in some other parasites. Trans-sialidases of parasitic organisms retain the hydrolytic activity of a sialidase, but are much less efficient. Consequently, the trans-sialidases catalyze a reversible transfer of terminal sialic acids from host sialyl-glycoconjugates to parasite surface glycoproteins in the absence of CMP-sialic acid.

Trypanosome cruzi, which causes Chagas disease, has a surface trans-sialidase. The trans-sialidase preferentially catalyzes the transfer of α-2,3-linked sialic acid to acceptors containing terminal β-galactosyl residues (Ribeirão et al., 1997, Glycobiol., 7: 1237-1246; Takahashi et al., 1995, Anal. Biochem., 230:333-342; Scudder et al., 1993, J. Biol. Chem., 268:9886-9891; Vandekerckhove et al., 1992, Glycobiol., 2:541-548). T. cruzi trans-sialidase (TcTs) has activity towards a wide range of saccharide, glycolipid, and glycoprotein acceptors which terminate with a β-linked galactose residue, and synthesizes exclusively an α2-3 sialosidic linkage (Scudder et al., supra). At a low rate, the trans-sialidase also transfers sialic acid from synthetic α-sialyl compounds, such as p-nitrophenyl-α-N-acetylneuraminic acid (NeuAc2-3Galβ1-4(Fucα1-3)Glc is not a donor-substrate). Modified 2-[4-methylumbelliferone]-α-ketoside of N-acetyl-D-neuraminic acid (4MU-NANA) and several derivatives thereof can also serve as donors for TcTs (Lee & Lee, 1994, Anal. Biochem, 216:358-364). Enzymatic synthesis of 3'-sialyl-lacto-N-biose I has been catalyzed by TcTs from lacto-N-biose I as acceptor and 2'-(4-methylumbelliferyl)-α-D-N-acelyneuraminic as donor of the N-acetylneuraminyl moiety (Vetere et al., 2000, Eur. J. Biochem., 267:942-949). Further information regarding the use of trans-sialidase to synthesize α2,3-sialylated conjugates can be found in European Patent Application No. 0 557 580 A2; and U.S. Pat. No. 5,409,817.

The intramolecular trans-sialidase from the leech Macrobdella decora exhibits strict specificity toward the cleavage of terminal Neu5Ac (N-acetylneuraminic acid) α2→3Gal linkage in sialyl-glycoconjugates and catalyzes an intramolecular trans-sialylation reaction (Luo et al., 1999, J. Mol. Biol., 285:323-332). Trans-sialidases primarily add sialic acid onto galactose acceptors, but will transfer sialic acid onto some other sugars. Transfer of sialic acid onto GalNAc, however, requires a sialyltransferase. Further information on the use of trans-sialidases can be found in PCT Application No. WO 93/18787; Vetere et al., 1997, Eur. J. Biochem., 247:1083-1090.

As used herein, the term "sialyltransferase," refers to enzymes that catalyze glycoside synthesis by inversion of the configuration of the added sugar and which require sugar nucleotides as the monosaccharide donor. An example of a sialyltransferase is the enzyme from Campylobacter (CST-I and CST-II). See, for example, U.S. Pat. Nos. 6,503,744, 6,096,529, and 6,210,933 and published U.S. Pat. Application 2002/2.042,369.

Other objects, aspects and advantages of the present invention will be apparent from the detailed description below.

DETAILED DESCRIPTION OF THE INVENTION

Introduction

The biological activity of many compounds, e.g, glycolipids, depends upon the presence or absence of a particular glycoform, the structure of the ceramide- or sphingosine-like backbone of the molecule and, in ceramide derivatives, the structure of the fatty acid amide component. Advantages of glycolipid compositions that have structures other than those found in nature include, for example, increased therapeutic half-life of due to reduced clearance rate, enhanced bioavailability, and altered bioactivity. Alteration of the structure of a glycolipid can also be used to target the glycolipid to a particular tissue or cell surface receptor that is specific for the altered glycolipid. The altered glycolipid can also be used as an inhibitor of the receptor, preventing binding of its natural ligand.

The present invention provides glycolipids that have novel structures. The compounds of the invention are exemplified herein by reference to ceramides, sphingosines and their analogues. The focus of the discussion is for clarity of illustration, and those of skill will appreciate that the invention is applicable to glycolipids other than those explicitly recited herein.

The Compounds

The methods of the invention can be practiced using any substrate that includes a suitable acceptor moiety for a glycosyltransferase, a trans-sialidase, and the like. Exemplary substrates include, but are not limited to, sphingosine and its analogues, ceramide and its analogues, peptides, glycosphingolipids and other biological structures (e.g., glycolipids, whole cells, and the like).

In a presently preferred embodiment, the invention addresses the deficiencies in the art by providing a class of glycosphingolipid derivatives according to Formula I:

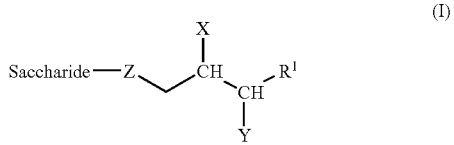

wherein, the symbol Z represents a member selected from O, S, C(R$^2$)$_2$ and NR$^2$. X is a member selected from H, —OR$^3$, —NR$^3$R$^4$, —SR$^3$, and —CHR$^3$R$^4$. The symbols R$^1$, R$^2$ and R$^3$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, —C(=M)R$^5$, —C(=M)-Z-R$^5$, —SO$_2$R$^5$, and —SO$_3$, in which the symbols M and Z represent members independently selected from O, NR$^6$ or S.

The symbol Y represents H, —OR$^7$, —SR$^7$, —NR$^7$R$^8$, substituted or unsubstituted alkyl, substituted or unsubstituted heteroalkyl, substituted or unsubstituted aryl, substituted or unsubstituted heteroaryl, or substituted or unsubstituted heterocycloalkyl. R$^5$, R$^6$, R$^7$ and R8 are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl.

In compounds of the invention in which X is OR$^3$ and R$^3$ is —C(O)R$^5$, Y is generally a group other than OH.

Any of X, Y or R$^1$, alone or in combination, can include a moiety that is a targeting moiety, a detectable label or a species that is intended to be incorporated into a lipid raft.

Exemplary compounds of the invention include those described above in which X is HR$^4$. The symbol R$^4$ represents H or —C(O)R$^5$. The symbol Y represents OH, and Z is O. In these compounds, R$^5$ is preferably other than a member selected from substituted or unsubstituted alkyl.

In another exemplary embodiment, the invention provides compounds according to Formula I in which R$^1$ comprises a moiety having the formula:

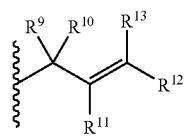

in which R$^9$, R$^{10}$, R$^{11}$, R$^{12}$ and R$^{13}$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, NR$^{14}$R$^{15}$, OR$^{14}$, —CN, and —C(=L)R$^{14}$. The symbol L represents O, S, or NR$^{16}$. R$^{14}$ and R$^{15}$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, C(O)R$^{17}$, OR$^{17}$, SR$^{17}$ and NR$^{17}$R$^{18}$. The symbols R$^{16}$, R$^{17}$ and R$^{18}$ independently represent H, substituted or unsubstituted alkyl, substituted or unsubstituted heteroalkyl, substituted or unsubstituted aryl, substituted or unsubstituted heteroaryl, or substituted or unsubstituted heterocycloalkyl. Moreover, a member selected from R$^9$ and R$^{10}$; R$^9$ and R$^{11}$; R$^9$ and R$^{12}$; R$^9$ and R$^{13}$; R$^{10}$ and R$^{11}$; R$^{10}$ and R$^{12}$; R$^{10}$ and R$^{13}$; R$^{11}$ and R$^{12}$; R$^{11}$ and R$^{13}$; and R$^{12}$ and R$^{13}$, together with the atom to which they are attached, are optionally joined to form a ring. The ring is a preferably a member selected from substituted or unsubstituted cycloalkyl, substituted or unsubstituted aryl, substituted or unsubstituted heteroaryl, and substituted or unsubstituted heteroalkyl ring systems having from 5-7 members.

In a still further exemplary embodiment, the invention provides compounds according to Formula I in which R$^1$ comprises a moiety having the formula:

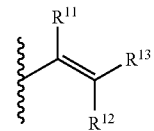

wherein the symbols R$^{11}$, R$^{12}$ and R$^{13}$ independently represent substituted or unsubstituted alkyl, substituted or unsubstituted heteroalkyl, substituted or unsubstituted aryl, substituted or unsubstituted heteroaryl, substituted or unsubstituted heterocycloalkyl, NR$^{14}$R$^{15}$, OR$^{14}$, —CN, or —C(=L)R$^{14}$. L, R$^{14}$, R$^{15}$, R$^{16}$, R$^{17}$, and R$^{18}$ are substantially as described above.

In another exemplary embodiment, the invention provides a compound according to Formula (I) in which R$^1$ comprises a moiety having the formula:

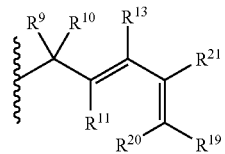

in which R$^9$, R$^{10}$, R$^{11}$, R$^{13}$, R$^{19}$, R$^{20}$ and R$^{21}$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, NR$^{14}$R$^{15}$, OR$^{14}$, —CN, and —C(=L)R$^{14}$. The configuration of the bond joining the carbons substituted with R$^{13}$ and R$^{14}$ may be either cis or trans.

The symbol L represents a O, S, or NR$^{16}$. R$^{14}$ and R$^{15}$ are members independently selected from H, substituted or unsubstituted alkyl, substituted or unsubstituted heteroalkyl, substituted or unsubstituted heteroaryl, substituted or unsubstituted heterocycloalkyl, C(O)R$^{17}$, OR$^{17}$, SR$^{17}$ and NR$^{17}$R$^{18}$. The symbols R$^{16}$, R$^{17}$ and R$^{18}$ independently represent H, substituted or unsubstituted alkyl, substituted or unsubstituted heteroalkyl, substituted or unsubstituted aryl, substituted or unsubstituted heteroaryl, or substituted or unsubstituted heterocycloalkyl.

Moreover, a member selected from R$^9$ and R$^{10}$; R$^9$ and R$^{11}$; R$^9$ and R$^{13}$; R$^9$ and R$^{21}$; R$^9$ and R$^{19}$; R$^9$ and R$^{20}$; R$^9$ and R$^{21}$; R$^{10}$ and R$^{11}$; R$^{10}$ and R$^{13}$; R$^{10}$ and R$^{19}$; R$^{10}$ and R$^{20}$; R$^{10}$ and $R^{21}$; $R^{11}$ and $R^{13}$; $R^{11}$ and $R^{19}$; $R^{11}$ and $R^{20}$; $R^{11}$ and $R^{21}$; and $R^{13}$ and $R^{19}$; $R^{13}$ and $R^{20}$; $R^{13}$ and $R^{21}$; $R^{19}$ and $R^{20}$; $R^{19}$ and $R^{21}$; and $R^{20}$ and $R^{21}$ together with the atoms to which they are attached, are optionally joined to form a ring. The ring is a member selected from substituted or unsubstituted cycloalkyl, substituted or unsubstituted aryl, substituted or unsubstituted heteroaryl, and substituted or unsubstituted heteroalkyl.

In an additional exemplary embodiment, $R^{13}$ is a member selected from substituted or unsubstituted heteroaryl. Preferred heteroaryl groups are those that include at least one endocyclic nitrogen atom. A representative nitrogen-containing heteroaryl group is the pyridyl moiety.

In another exemplary embodiment, the classes of compounds discussed above include species in which $R^{13}$ is —C(O)$NR^{13a}R^{13b}$, wherein $R^{13a}$ and $R^{13}$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

The classes of compounds set forth above also include species in which $R^{11}$ is $NR^{11a}R^{11b}$. The symbols $R^{11a}$ and $R^{11b}$ independently represent H, substituted or unsubstituted alkyl or substituted or unsubstituted heteroalkyl.

The saccharide moiety of the glycosphingolipids of the invention may be of any structure exhibititing a desired biological activity. In general, the saccharide moiety will include at least one of Gal, Glc, GlcNAc or Sia. The saccharide is optionally fucosylated. In certain preferred saccharide moieties, a Sia is bound to a Gal residue. In other preferred saccharide moieties, a Gal is bound to a Glc. In still further preferred saccharide moieties, a GlcNAc is bound to a Gal. A presently preferred saccharide moiety motif includes a backbone with a terminal Gal attached to a penulitimate GalNAc, which is attached to Gal, which is in turn attached to Glc, which is attached to the glycosphingolipid backbone. The saccharide moieties may have one or more groups that are acetylated or deacetylated.

Exemplary saccharide moieties include:

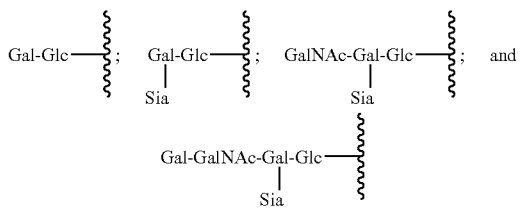

In a still further exemplary embodiment, the sialic acid substituted oligosaccharide is sulfated, i.e., one or more hydroxyl groups in the sialic acid substituted oligosaccharide is modified to form a sulfate ester. Methods of preparing sulfate esters of synthetic gangliosides are disclosed in U.S. Pat. No. 5,849,717.

In another example of a synthetic glycosphingolipid of the invention, the carboxylic acid group of the sialic acid residue is esterified. Included are "inner esters," i.e., where a lactone forms between the carboxyl group and a hydroxyl group in the oligosaccharide, and "outer esters", i.e., where the carboxyl group is esterified with an alcohol ROH. ROH can be a substituted or unsubstituted alkyl, substituted or unsubstituted heteroalkyl, substituted or unsubstituted heterocycloalkyl, substituted or unsubstituted aryl or substituted or unsubstituted heteroaryl group. Methods of preparing synthetic glycosphingolipids in which the carboxyl group of a sialic acid is esterified are disclosed in U.S. Pat. No. 5,264,424.

Further synthetic glycosphingolipids of the invention include a Sia residue that is amidated (i.e., derivatizing the carboxylic acid moiety) with HNR or with an aliphatic amino acid containing a carboxylic acid or sulfonic acid group. R is as described above. Methods of preparing synthetic glycosphingolipids with functionalized sialic acid carboxyl moieties are disclosed in U.S. Pat. No. 5,350,841.

In yet another example of a synthetic glycosphingolipid, one or more of the hydroxyl groups in the oligosaccharide and/or sialic acid residue is acylated, i.e., is converted to —OCOR. R is as described above. Methods of preparing synthetic glycosphingolipids with an acylated sialic acid residue are disclosed in U.S. Pat. Nos. 5,484,775 and 5,264,424.

The N-acyl group ((NC(O)R) of the sphingosine group can be derived from a wide variety of carboxylic acids (or corresponding activated derivative, e.g., active ester, acid halide, etc.). Acylation can be carried out in the conventional way, for example, by reacting the starting products with an acylating agent, particularly with a reactive functional derivative of the acid, whose residue is to be introduced. Exemplary reactive functional derivatives of the acid include halides, anhydrides, and active esters. The acylation may be carried out in the presence of a base, (e.g., TEA, pyridine or collidine). Acylation is optionally carried out under anhydrous conditions, at room temperature or with heating. The Schotten-Baumann method may also be used to effect acylation under aqueous conditions in the presence of an inorganic base. In some cases it is also possible to use the esters of the acids as reactive functional derivatives. For acylation, it is possible to also use methods involving activated carboxy derivatives, such as are known in peptide chemistry, for example using mixed anhydrides or derivatives obtainable with carbodiimides or isoxazole salts.

Exemplary methods of acylation include: (1) reaction of the lysoglycosphingolipid derivative with the azide of the acid; (2) reaction of the lysoglycosphingolipid derivative with an acylimidazole of the acid obtainable from the acid with N,N'-carbonyldiimidazole; (3) reaction of the lysoglycosphingolipid derivative with a mixed anhydride of the acid and of trifluoro-acetic acid; (4) reaction of the lysoglycosphingolipid derivative with the chloride of the acid; (5) reaction of the lysoglycosphingolipid derivative with the acid in the presence of a carbodiimide (such as dicyclohexylcarbodiimide) and optionally of a substance such as 1-hydroxybenzotriazole; (6) reaction of the lysoglycosphingolipid derivative with the acid by heating; (7) reaction of the lysoglycosphingolipid derivative with a methyl ester of the acid at a high temperature; (8) reaction of the lysoglycosphingolipid derivative with a phenol ester of the acid, such as an ester with para-nitrophenol; and (9) reaction of the lysoglycosphingolipid derivative with an ester derived from the exchange between a salt of the acid and 1-methyl-2-chloropyridine iodide or similar products.

The acids maybe derived from saturated or unsaturated, branched- or straight-chain substituted or unsubstituted alkyl acids, substituted or unsubstituted fatty acids (e.g hydroxy fatty acids). The acids are preferably $C_1$-$C_{40}$ acids. The acyl group may include the exemplary substructures: —$(CH_2)_p CH_3$, —CH=CH—$(CH_2)_p CH_3$, —CHOH—$(CH_2)_p CH_3$, —CH=CH—$(CH_2)_2$—CH=CH—$(CH_2)_p CH_3$, —CH=CH—$(CH_2)_2$—C≡C—$(CH_2)_p CH_3$, —CHOH—$(CH_2)_3$—CH=CH—$(CH_2)_p CH_3$, aryl, alkylaryl, or linker, where p is 0-40. In general, the length of the acyl component is preferably from 8 to 30 carbons, more preferably 10-25, and more preferably still from 16 to 20 carbons.

A non-limiting list of acids includes: dichloroacetic acid, trichloroacetic acid and their fluorinated or brominated analogues; 2,2-dichloropropionic acid, 2,3-dichloropropionic acid, 2,2,3-trichloropropionic acid, normal-2,2-dichlorobutyric acid, 2,2-dichlorovalerianic acid, 2-chloroisovalerianic acid, 2,3-dichlorovalerianic acid, pentafluoropropionic acid, 3,3-dichloropivalic acid, 3-chloro-2,2-dimethylpropionic acid, chloro-difluoroacetic acid, 2,2-dichlorocapronic acid, 2-monochloropropionic, normal-2-monochlorobutyric, 2-monochlorovaleric, and 2-monochlorocapronic acids and the fluorinated or brominated analogues of these acids; 2-chloropalmitic acid, 2-chlorostearic acid, 2-chlorooleic acid, 2-chlorolaurinic acid, 2-chlorobehenic acid, 4-chlorophenoxyacetic acid, 2-hydroxypropionic acid (lactic acid), 3-hydroxypropionic acid, 2-hydroxybutyric acid, 2-hydroxyvaleric acid, 3-hydroxyvaleric acid, 2,3-dihydroxybutyric acid and 2,3-dihydroxyvaleric acid and $C_1$-$C_{40}$ lower aliphatic ethers or esters thereof; methoxyacetic acid, 12-hydroxystearic acid, 2-(4-hydroxyphenoxy) propionic acid, 2-hydroxyisocapronic acid, 2-hydroxyisobutyric acid and 4-fluoro-phenoxyacetic acid; pyruvic acid, acetacetic acid, levulinic acid and ketals thereof with lower aliphatic alcohols having a maximum of 4 carbon atoms; mercaptoacetic, 2-mercaptopropionic, 2-mercaptobutyric and 2-mercaptovalerianic acids and $C_1$-$C_{40}$ lower aliphatic thioethers or thioesters thereof; 2-mercaptolaurinic, oleic and palmitic acids and $C_1$-$C_4$ lower aliphatic thioethers or thioesters thereof; malonic acid, glutaric acid, monomethylglutaric acid, 3-hydroxy-3-methylglutaric acid, maleic acid, malic acid, succinic acid, fumaric acid, azelaic acid and $C_1$-$C_{40}$ aliphatic esters thereof; sulfoacetic acid, 2-sulfopropionic acid, 2-sulfobutyric acid, 2-sulfovalerianic acid and $C_1$-$C_{40}$ aliphatic sulfate esters thereof. Also included are 2-sulfolaurinic acid, 2-sulfo-oleic acid, 2-sulfopalmitic acid, 2-sulfostearic acid and $C_1$-$C_{40}$ lower aliphatic sulfate esters thereof; sulfamides or the sulfamides wherein the amine is optionally substituted with one or two $C_1$-$C_{40}$ lower alkyl groups or by $C_1$-$C_{40}$ alkylene groups; acetic acid, propionic, butyric and valerianic acids substituted in the 2-position by a $C_1$-$C_4$ alkyl, acylsulfoxide or $C_1$-$C_{40}$ alkylsulfone group; cyanacetic acid, 2-cyanpropionic acid, 2-cyanbutyric acid, 2-cyanvalerianic acid, aminoacetic acid, 2-aminopropionic acid, 2-aminobutyric acid, 3-aminobutyric acid, 4-aminobutyric acid, 2-aminovalerianic acid, 4-aminovalerianic acid and derivatives thereof with the amine optionally substituted with one or two $C_1$-$C_{40}$ alkyls, $C_1$-$C_{40}$ alkylene groups or $C_1$-$C_4$ acyl group; di-methylglycine, 3-diethylaminopropionic acid, carnitine, and cysteic acid.

In the particular case of acyl groups derived from acids containing free hydroxy, mercapto, carboxy groups, or primary or secondary amino groups, it is generally preferable to protect such groups during the acylation reaction. Methods for protecting such groups are available in the art. Such protective groups should be easily eliminated at the end of the reaction. Exemplary protecting groups include the sulfonamide, alloc, phthaloyl group and the benzyloxycarbonyl group, which serves to advantage for the protection of the amino group. Thus, for example, in the preparation of derivatives containing y-amino butyric acid, a derivative, of this acid is first prepared, where the amino group is bound to the phthaloyl group, and after acylation with the lysoglycosphingolipid derivative the phthaloyl group is eliminated by hydrazinolysis. The benzyloxycarbonyl group can be eliminated by hydrogenolysis. This residue may also serve for the protection of the hydroxy groups. The carboxy group can be protected by esterification, for example, with the alcohols used in peptide chemistry.

The invention also provides methods to prepare metal or organic base salts of the glycosphingolipid compounds according to the present invention having free carboxy functions, and these also form part of the invention. It is possible to prepare metal or organic base salts of other derivatives of the invention too, which have free acid functions, such as esters or peracylated amides with dibasic acids. Also forming part of the invention are acid addition salts of glycosphingolipid derivatives, which contain a basic function, such as a free amino function, for example, esters with aminoalcohols. Of the metal or organic base salts particular mention should be made of those which can be used in therapy, such as salts of alkali or alkaline earth metals, for example, salts of potassium, sodium, ammonium, calcium or magnesium, or of aluminum, and also organic base salts, for example of aliphatic or aromatic or heterocyclic primary, secondary or tertiary amines, such as methylamine, ethylamine, propylamine, piperidine, morpholine, ephedrine, furfurylamine, choline, ethylenediamine and aminoethanol. Of those acids which can give acid addition salts of the glycosphingolipid derivatives according to the invention special mention should be made of hydroacids such as hydrochloric acid, hydrobromic acid, phosphoric acid, sulfuric acid, lower aliphatic acids with a maximum of 7 carbon atoms, such as formic, acetic or propionic acids, succinic and maleic acids. Acids or bases, which are not therapeutically useful, such as picric acid, can be used for the purification of the glycosphingolipid derivatives of the invention and also form part of the invention.

Representative compounds of the invention are set forth in FIG. 16.

The invention also encompasses all pharmaceutically acceptable isomers, salts, hydrates, solvates, and prodrugs of each of the compounds described above. In addition, such compounds can exist in various isomeric and tautomeric forms, and all such forms are meant to be included in the invention, along with pharmaceutically acceptable salts, hydrates, and solvates of such isomers and tautomers.

Methods of Preparation

According to the invention, synthetic glycosphingolipid compounds of the invention are prepared using, unless otherwise indicated, conventional methods and protocols in chemistry and enzymology known in the art. For example, compounds of the invention may be prepared by chemical and enzymatic processes as outlined in Schemes 1-6 set forth below.

The saccharide moiety of the compounds of the invention can be prepared by any means known in the art including those methods described in U.S. Pat. Nos. 5,922,577, 6,284,493 and 6,331,418, each of which is incorporated herein in its entirety by reference. Preferably, the saccharide portion of the compounds of the invention is prepared enzymatically whereby a specific enzyme may be used to affect transfer of a monosaccharide from a donor molecule to an acceptor molecule, each as defined herein.

More specifically, disaccharides, oligosaccharides and polysaccharides, as found in the synthetic glycosphingolipid compounds of the invention, are preferably prepared biosynthetically by the use of glycosyltransferases. Such glycosyltransferase reactions may be carried out in the presence of an organic solvent, such as, for example, methanol, ethanol, dimethylsulfoxide, isopropanol, tetrahydrofuran, chloroform, and the like, either singly or in combination. Alternatively, such glycosyltransferase reactions may be conducted in a biological medium in vitro, such as a biological buffer, a cell lysate, or on a chromatographic support, wherein the glycosyltransferase is immobilized on the chromatographic support and the other components of the reaction mixture are contacted with the glycosyltransferase by contacting the components with the choromatographic support in an aqueous medium.

Glycosyltransferase-mediated synthesis of saccharides can be conducted in vivo or in vitro. For example, whole-cell expression systems may be used for enzymatic synthesis, e.g., glycosyltransferase-mediated synthesis. Cell types useful for the expression of glycosyltransferases and production of saccharide structures include bacterial cells, yeast cells, and insect cells, as would be understood by one of skill in the art. The desired saccharide product can be isolated from the cell in which it was synthesized by lysis of the cell, or by isolation of cell culture medium when using a cell that secretes the saccharide product into the culture medium. The saccharide product may then be purified by means described elsewhere herein, or it may be used without further purification in a lysate or cell culture medium.

As understood by one of skill in the art, the enzyme used may vary depending upon the saccharide to be transferred to the donor. Examples of suitable enzymes include, but are not limited to, glycosyltransferases, trans-sialidases, and sialyltransferases. The choice of glycosyltransferase(s) used in a given synthesis method of the invention will depend upon the identity of the acceptor and donor molecules used as the starting material and the nature of the desired end product. A method of the invention can involve the use of more than one glycosyltransferase, where more than one saccharide is to be added. Multiple glycosyltransferase reactions can be carried out simultaneously, i.e., in the same reaction mixture at the same time, or sequentially.

To obtain sufficient amounts of glycosyltransferase for large-scale in vitro reaction, a nucleic acid that encodes a glycosyltransferase can be cloned and expressed as a recombinant soluble enzyme by methods known to one of ordinary skill in the art. The expressed enzyme may then be purified by means known to one of ordinary skill in the art, or it may be used without further purification in a lysate or cell culture medium.

By way of example, the saccharide moiety:

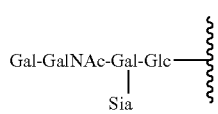

can be prepared by contacting an acceptor molecule, e.g., a ceramide or sphingoid, containing a glucose (Glc) with a galactosyltransferase and a galactose (Gal) donor molecule to form:

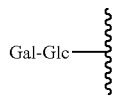

which in turn can be contacted with a trans-sialidase and a Sia donor molecule to form:

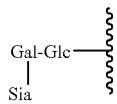

which in turn can be contacted with a N-acetylated galactose (GalNAc)-transferase and a GalNAc donor molecule to form:

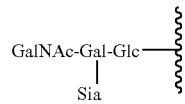

which in turn can be contacted with a galactosyltransferase and a galactose (Gal) donor molecule to form the desired saccharide.

The initial monosaccharide may be added to the substrate, e.g. ceramide, sphingosine or analogue thereof, depending on the desired end product, using either a ceramide glucosyltransferase (e.g., EC 2.4.1.80, for glucosylceramide) or a ceramide galactosyltransferase (e.g., EC 2.4.1.45, for galactosylceramide). For review of glycosphingolipid biosynthesis, see, e.g., Ichikawa and Hirabayashi (1998) *Trends Cell Biol.* 8:198-202. Ceramide glucosyltransferases are available from various sources. For example, the human nucleotide sequence is known (GenBank Accession No. D50840; Ichikawa et al. (1996) *Proc. Nat'l. Acad. Sci. USA* 93:4638-4643), so recombinant methods can be used to obtain the enzyme. The nucleotide sequence of the human ceramide galactosyltransferase also has been reported (GenBank Accession No. U62899; Kapitonov and Yu (1997) *Biochem. Biophys. Res. Commun.* 232: 449-453), and thus the enzyme is easily obtainable. The acceptor used in these reactions can be any of N-acylsphingosine, sphingosine and dihydrosphingosine. Suitable donor nucleotide sugars for the glycosyltransferase include UDP-Glc and CDP-Glc, while the galactosyltransferase typically uses UDP-Gal as a donor.

Another possible biosynthetic method for the synthesis of the saccharide portion of a compound of the invention is exemplified in Scheme 1 below. In a preferred embodiment, the acceptor molecule is non-immobilized. For example, the acceptor molecule may be free in solution or otherwise not associated with other acceptor molecules.

Additional saccharide residues may be added to a compound of the invention without prior modification of the glycosylation pattern of the glycosphingolipid starting material. Alternatively, the invention provides methods of altering the glycosylation pattern of a glycosphingolipid prior to adding the additional saccharide residues. If the starting glycosphingolipid does not provide a suitable acceptor for the glycosyltransferase that catalyzes a desired saccharide addition, one can modify the glycosphingolipid to include an acceptor by methods known to those of skill in the art.

For example, to provide a suitable acceptor for a sialyltransferase, a suitable acceptor can be synthesized by using a galactosyltransferase to attach a galactose residue to, for example, a Glc or other appropriate saccharide moiety that is linked to the glycosphingoid. In other embodiments, glycosphingoid-linked oligosaccharides can be first "trimmed," either in whole or in part, to expose either an acceptor for the sialyltransferase or a moiety to which one or more appropriate residues can be added to obtain a suitable acceptor. Enzymes such as glycosyltransferases and endoglycosidases are useful for the attaching and trimming reactions.

Sialyltransferases and other glycosyltransferases can be used either alone or in conjunction with additional enzymes. For example, FIG. 1 provides a schematic diagram of two methods for synthesis of the ganglioside GM2 by enzymatic synthesis using as the starting material lactosylceramide obtained from bovine buttermilk. In the first method, a ceramide is contacted with one or more enzymes to append a saccharide unit to the ceramide. In the second route, the ceramide is converted to the corresponding sphingosine by hydrolyzing the caboxylic acid amide. One or more enzymes is used to append the saccharyl moiety onto the sphingosine. After the saccharide unit is prepared, the amino group of the sphingosine is acylated with a reactive carboxylic acid derivative, thereby, forming the ceramide.

Figure 2:
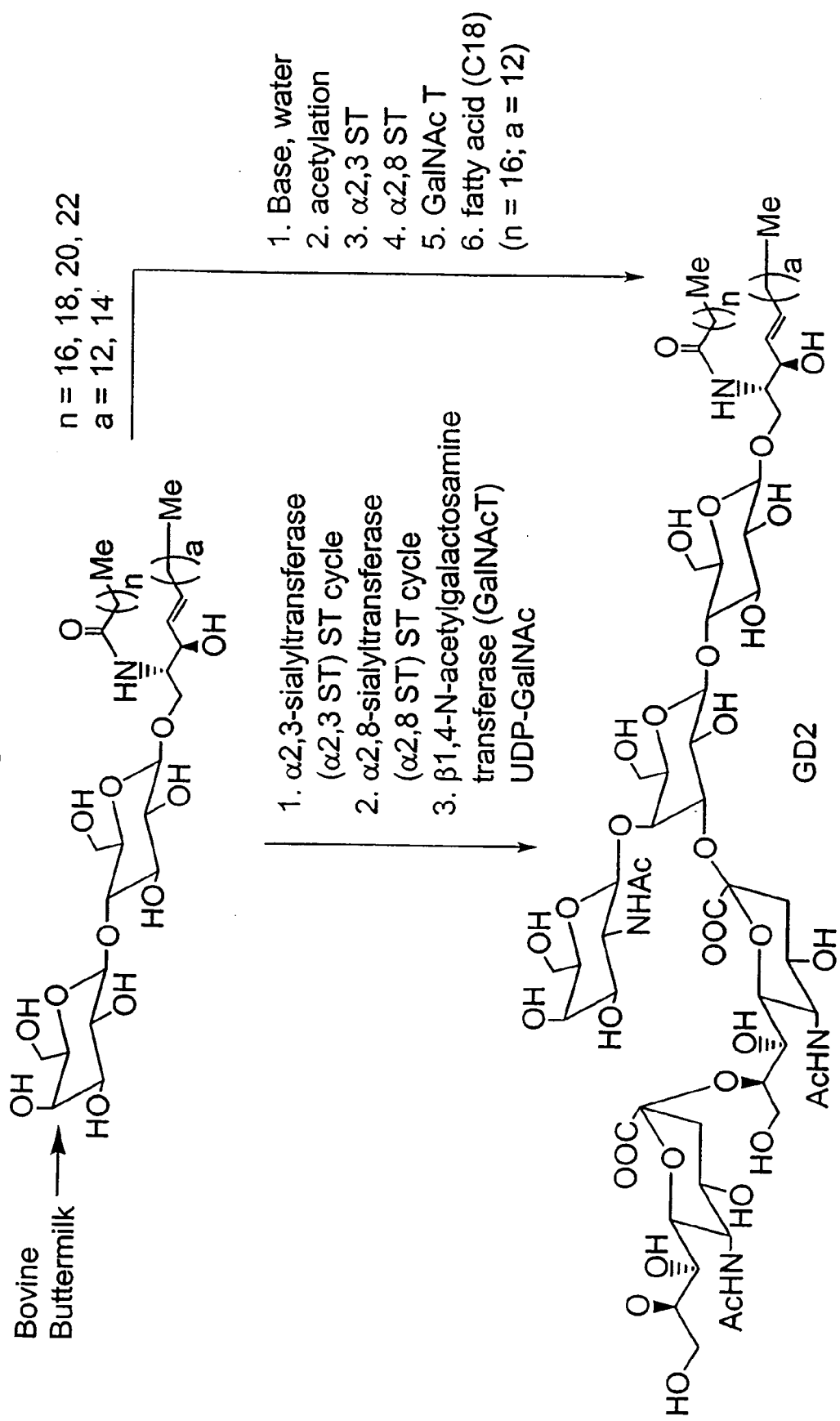
FIG. 2 is a schematic diagram of two methods for synthesizing the ganglioside $GD_2$ from lactosylceramide obtained from bovine buttermilk.

FIG. 2 shows a schematic diagram of two pathways for synthesis of the glycosphingolipid $GD_2$ starting from lactosylceramide. Each pathway involves the use of two different sialyltransferases (an α2,3ST and an α2,8ST), as well as a GalNAc transferase. In an exemplary pathway, the fatty acid is removed from the lactosylceramide by treatment with base (Step 1). Alternatively, can originate from a lysoceramide. Acetylation is then performed (Step 2), after which a sialic acid is attached to the galactose residue in an α2,3 linkage by an α2,3 sialyltransferase (Step 3). The sialylation steps are performed, preferably in the presence of an organic solvent as described herein, thereby driving the reaction nearly to completion. A GalNAc residue is then added to the galactose in a β1,4 linkage using a GalNAc transferase (Step 5). Finally, a fatty acid is added, e.g., by reaction with steroyl chloride, to complete the glycosphingolipid (Step 6). The acylation can be performed at any stage of the process.

Figure 3:
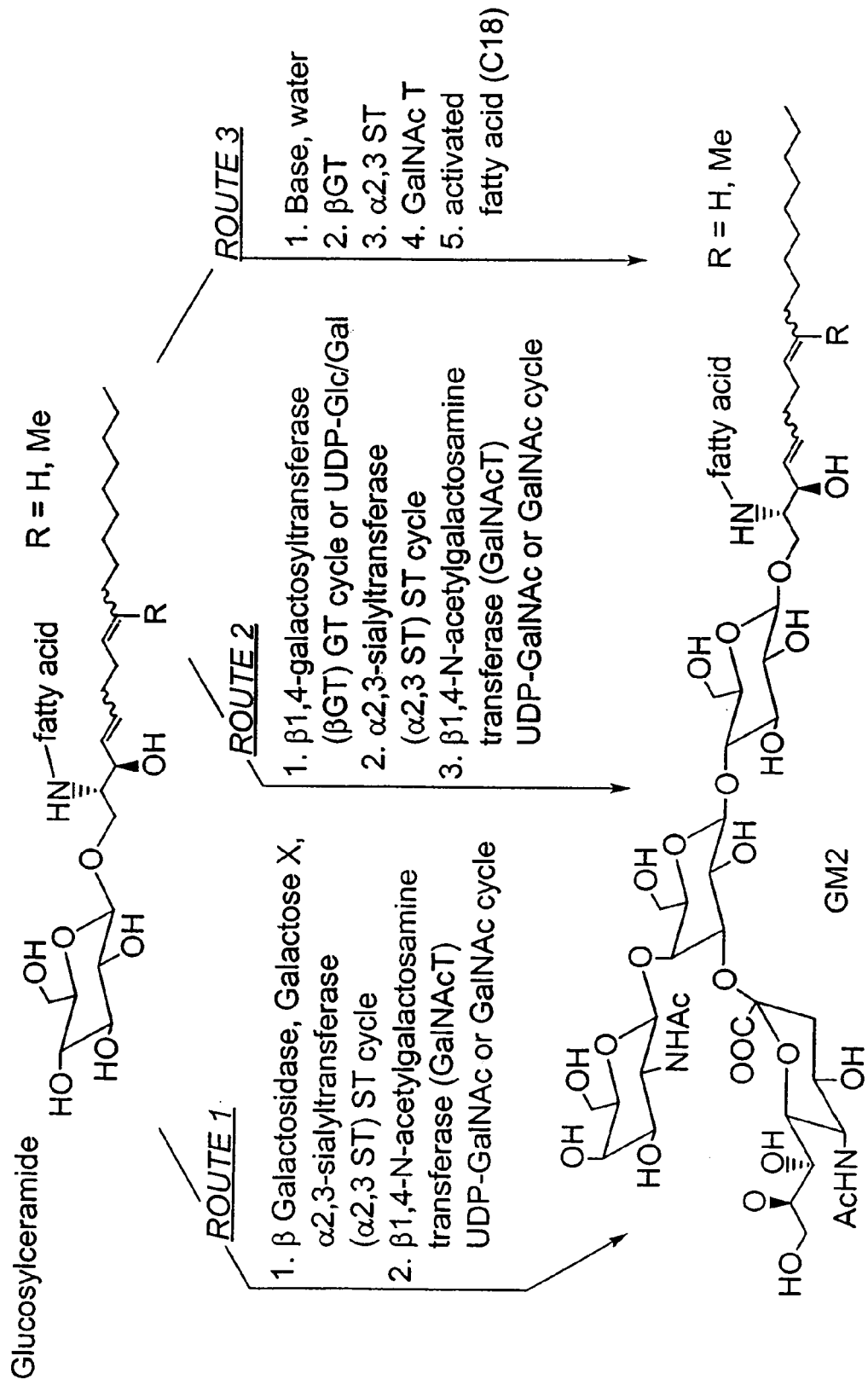
FIG. 3 is a collection of three routes for synthesizing a GM2 ganglioside using a plant glucosylceramide as the starting material.

FIG. 3 provides additional exemplary routes to compounds of the invention. In the first scheme, glucosylceramide is contacted with a galactosidase, an activated galactose donor and a sialyltransferase. The resulting sialylated ceramide is contacted with a GalNAc transferase to provide the desired product. In an alternative route, glucosylceramide is treated with a Gal transferase, followed by a sialyltransferase. The sialylated intermediate is contacted with a GalNAc transferase to produce the desired product. In the first step of the third route, the ceramide is converted to the corresponding sphingosine by hydrolyzing the carboxylic acid amide. The sphingosine if treated with a galactosyltransferase, followed by a sialyltransferase. The sialylated intermediate is contacted with a GalNAc transferease and, subsequently, the amine of the sphingosine is acylated to form the desired ceramide.

Figure 5:
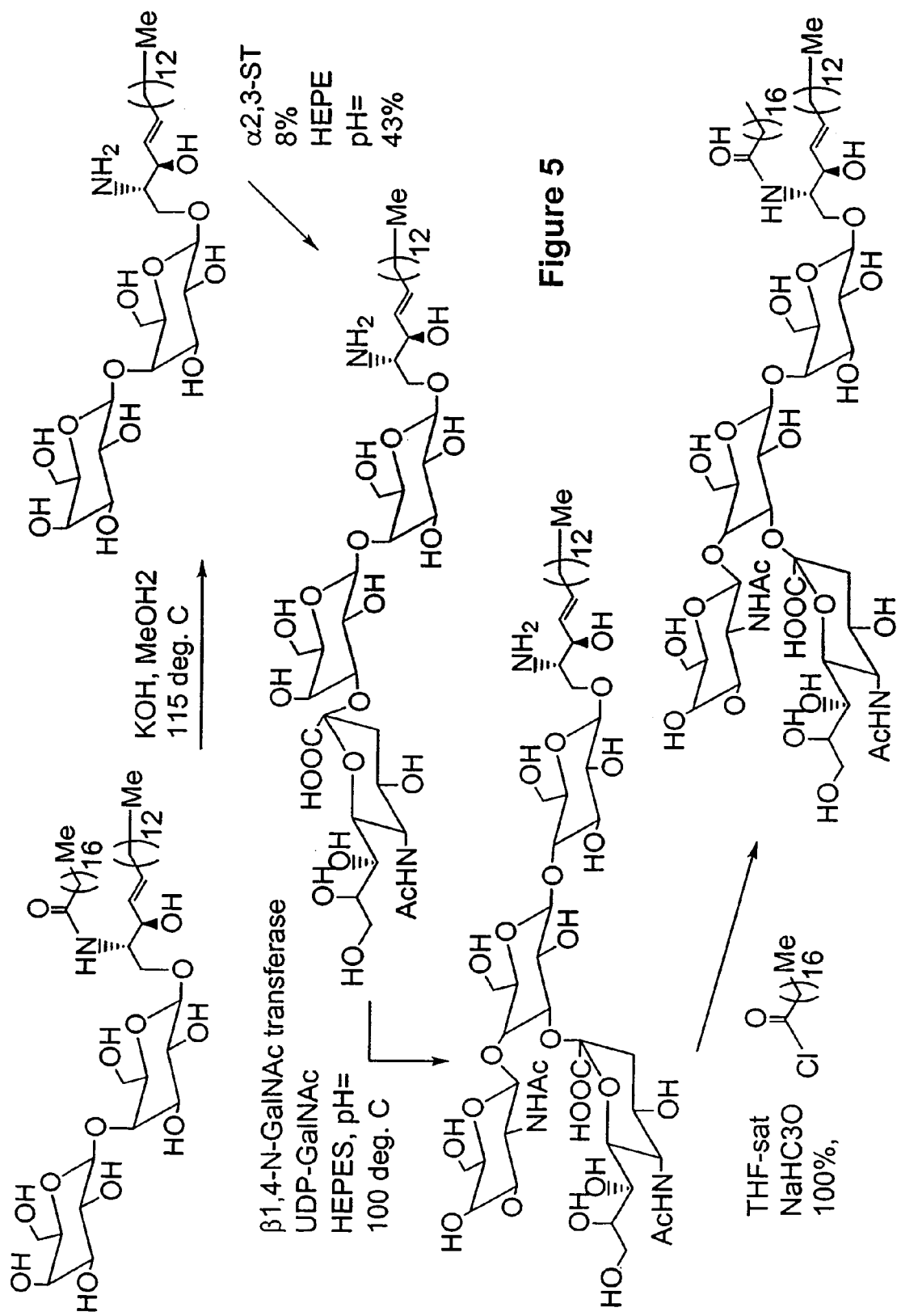
FIG. 5 is a scheme used for synthesis of the ganglioside GM2 from lactosylceramide via deacylation, two consecutive enzymatic glycosylations, and final chemical acylation.
Figure 6:
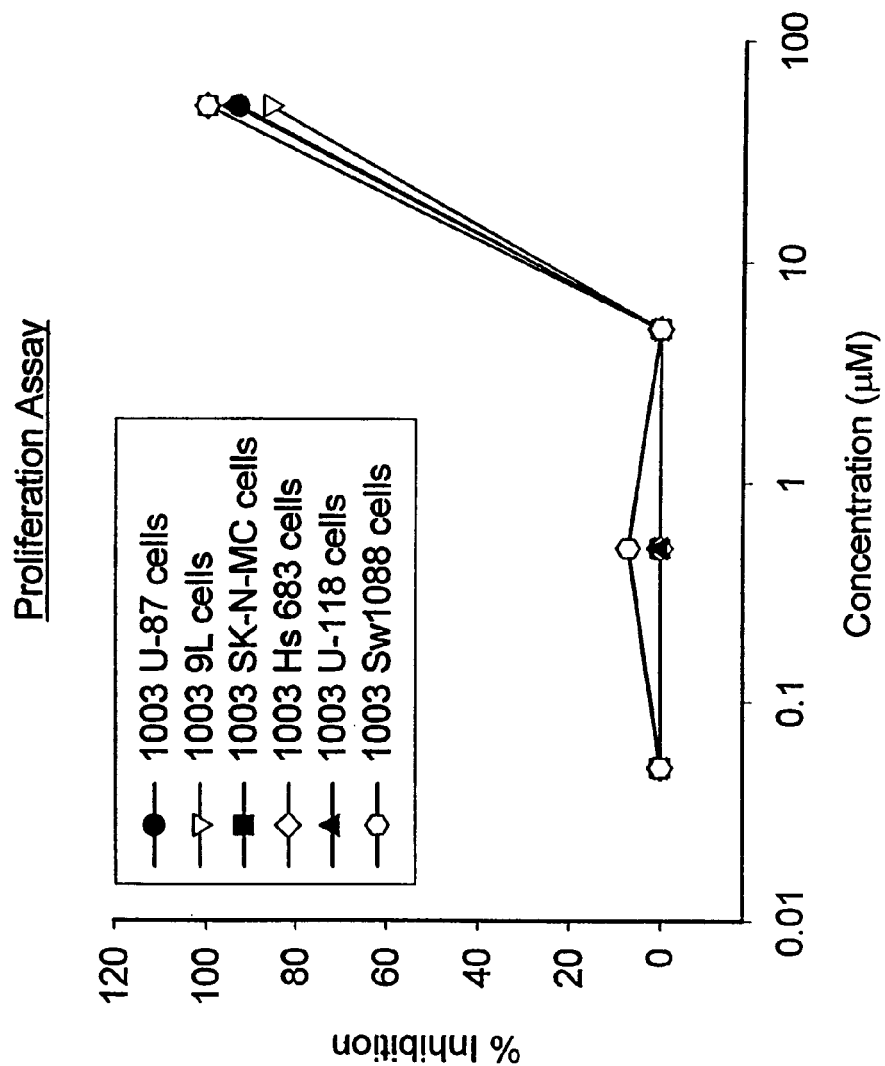
FIG. 6 shows attenuation of brain cancer cell growth when the cells are treated with various compounds of the present invention. Compound 2, at 50 µM, causes almost 100% growth inhibition in all cell lines (86-100%).
Figure 7:
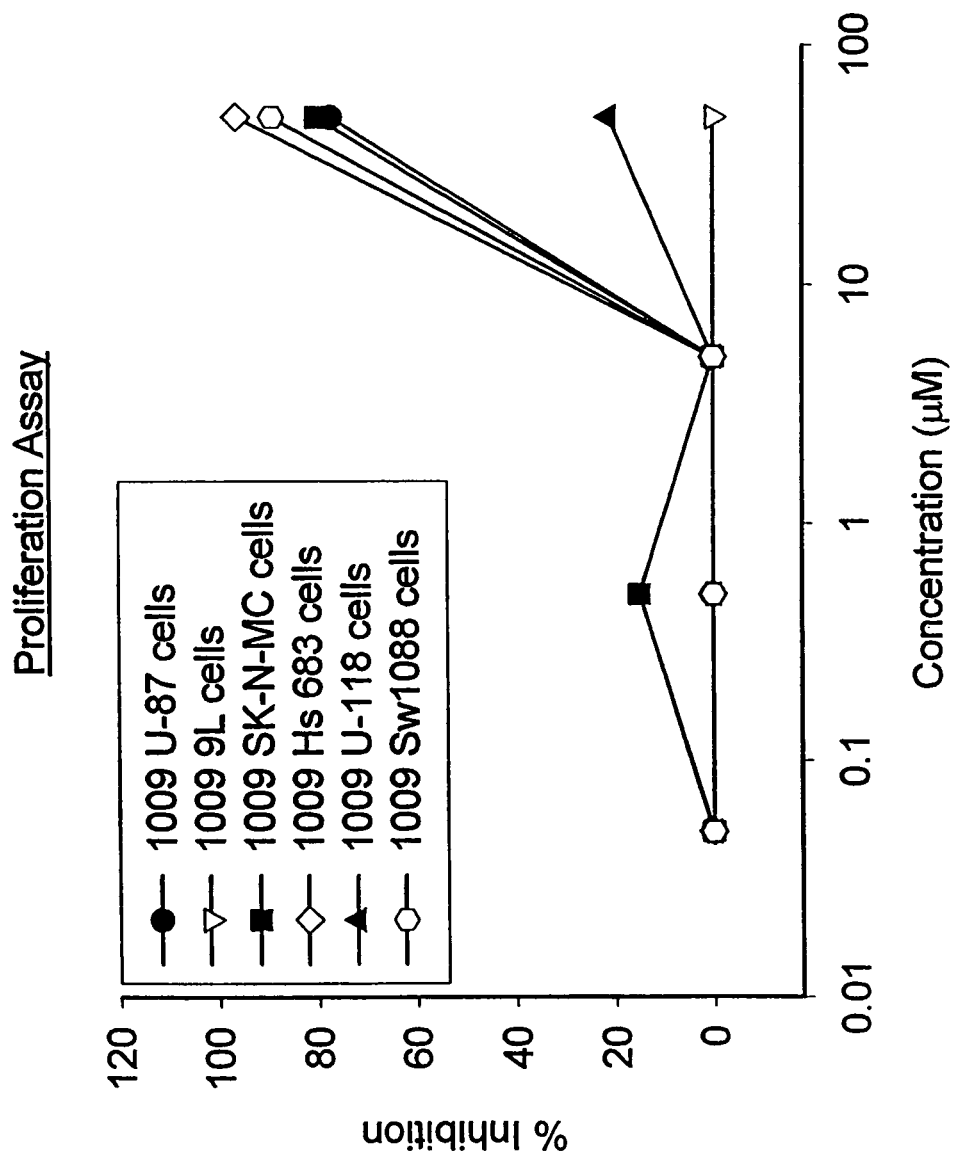
FIG. 7 shows attenuation of brain cancer cell growth when the cells are treated with various compounds of the present invention. Compound 8 has a profile similar to that for compound 2 in four cell lines (77-89% growth inhibition with 50 µM compound 8) and in U-118 cells, the growth inhibition with 50 µM compound 8 is 21%.
Figure 8:
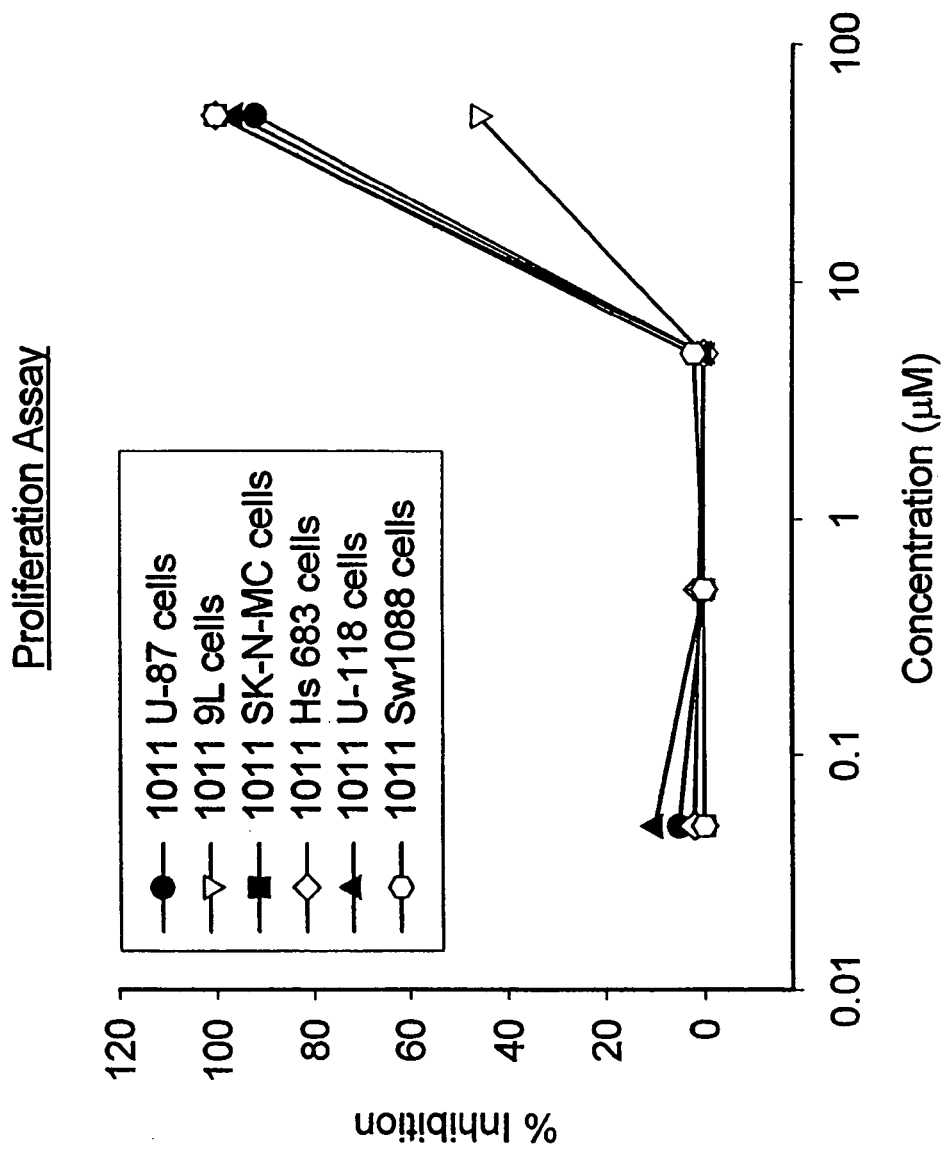
FIG. 8 shows attenuation of brain cancer cell growth when the cells are treated with various compounds of the present invention. Compound 10 has activity similar to compound 2, with the exception that the inhibition of 9L cells by 50 µM compound 10 was 46%.
Figure 9:
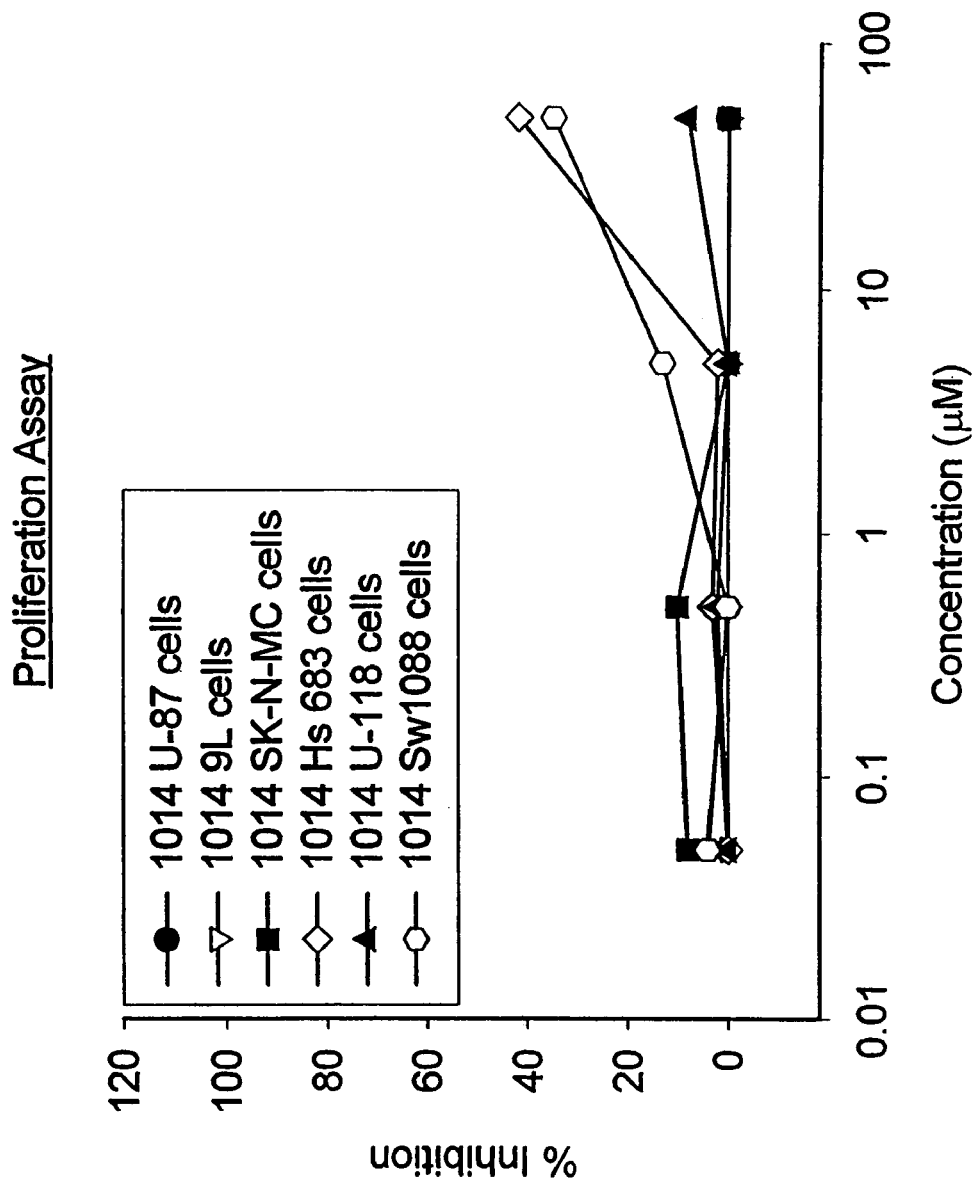
FIG. 9 show attenuation of brain cancer cell growth when the cells are treated with various compounds of the present invention. Compound 13, when used to treat Hs 683 and Sw1088 cells, inhibited proliferation 42% and 35%, respectively, when used at a concentration of 50 µM.
Figure 10:
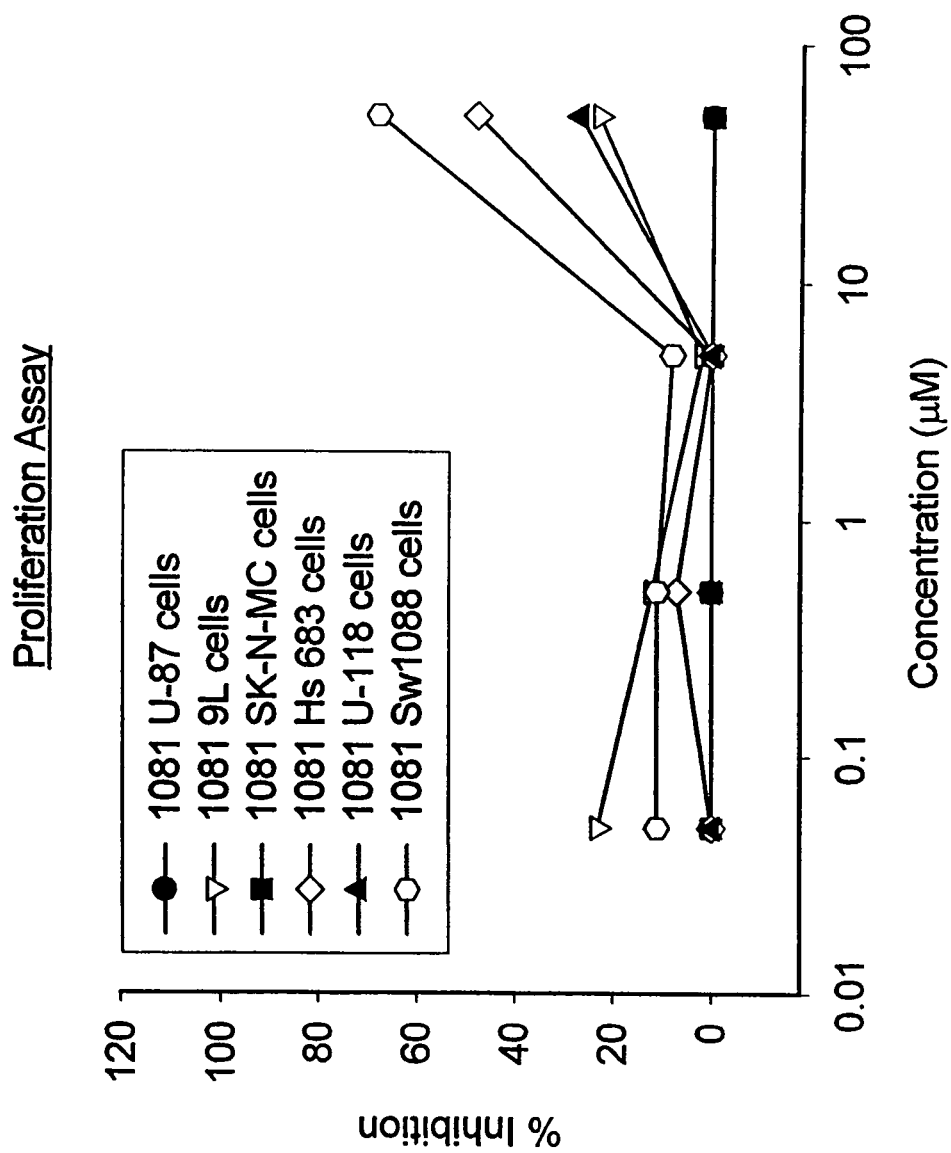
FIG. 10 shows attenuation of brain cancer cell growth when the cells are treated with various compounds of the present invention. 50 µM of compound 56 inhibited proliferation of 9L 23%, U-118 cells 27%, Hs 683 cells 48%, and Sw 1088 cells 68%.
Figure 11:
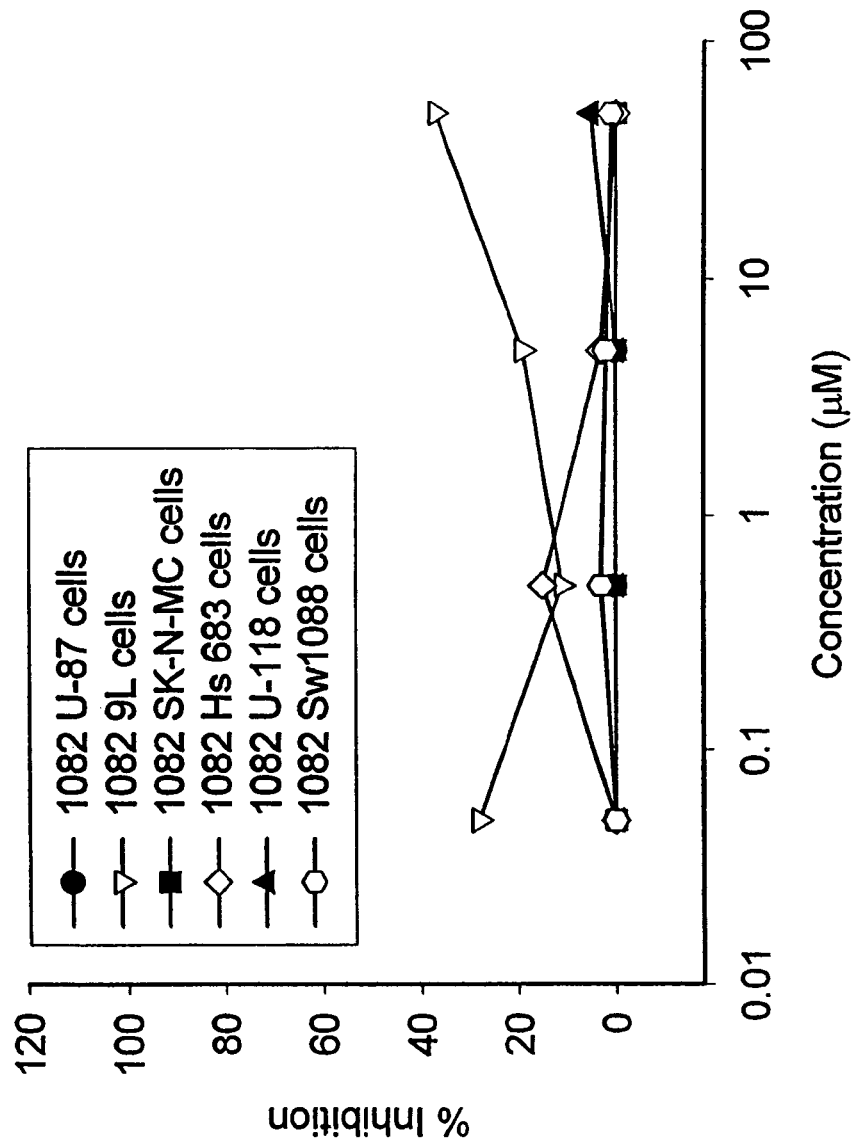
FIG. 11 shows attenuation of brain cancer cell growth when the cells are treated with various compounds of the present invention. Compound 57 inhibited the growth of 9L cells 11-37%.
Figure 12:
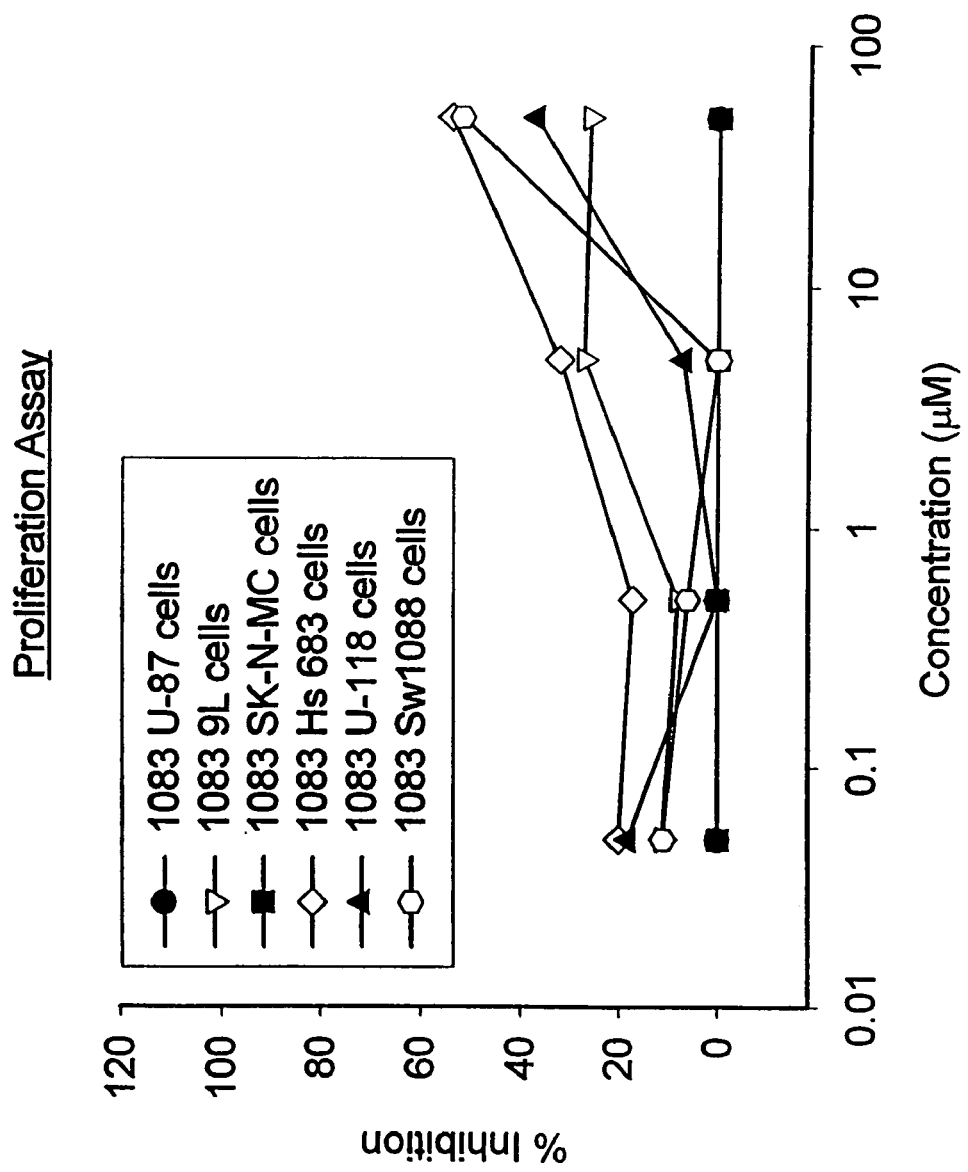
FIG. 12 shows attenuation of brain cancer cell growth when the cells are treated with various compounds of the present invention. Compound 58, at 5 µM, inhibited growth of 9L and Hs 683 cells (27% and 32%, respectively). At 50 µM, compound 58 inhibited growth of 9L, Hs 683, U-118, and Sw 1088 cells 26-54%.
Figure 13:
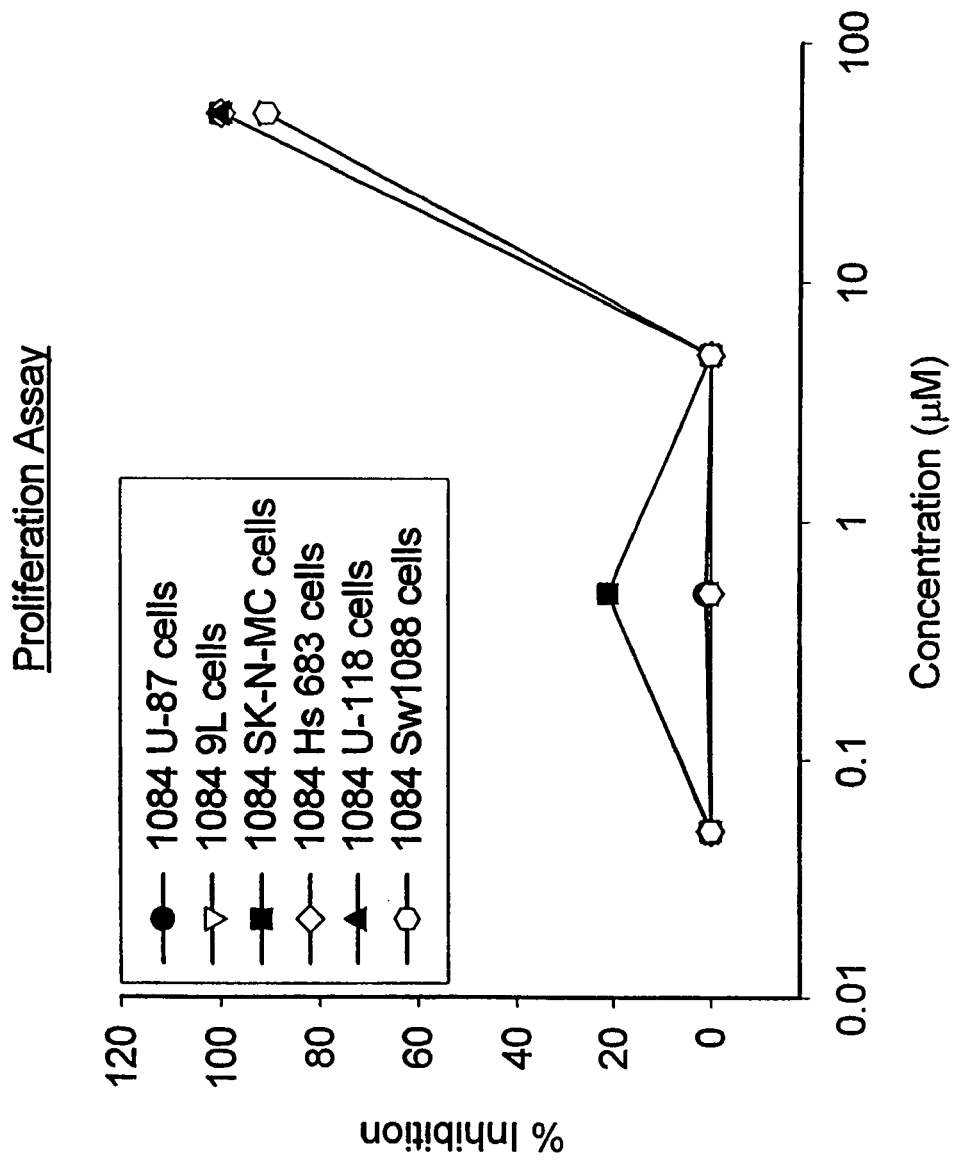
FIG. 13 shows attenuation of brain cancer cell growth when the cells are treated with various compounds of the present invention. Compound 59 strongly inhibited growth in all cell lines at 50 µM compound (91-100%).
Figure 14:
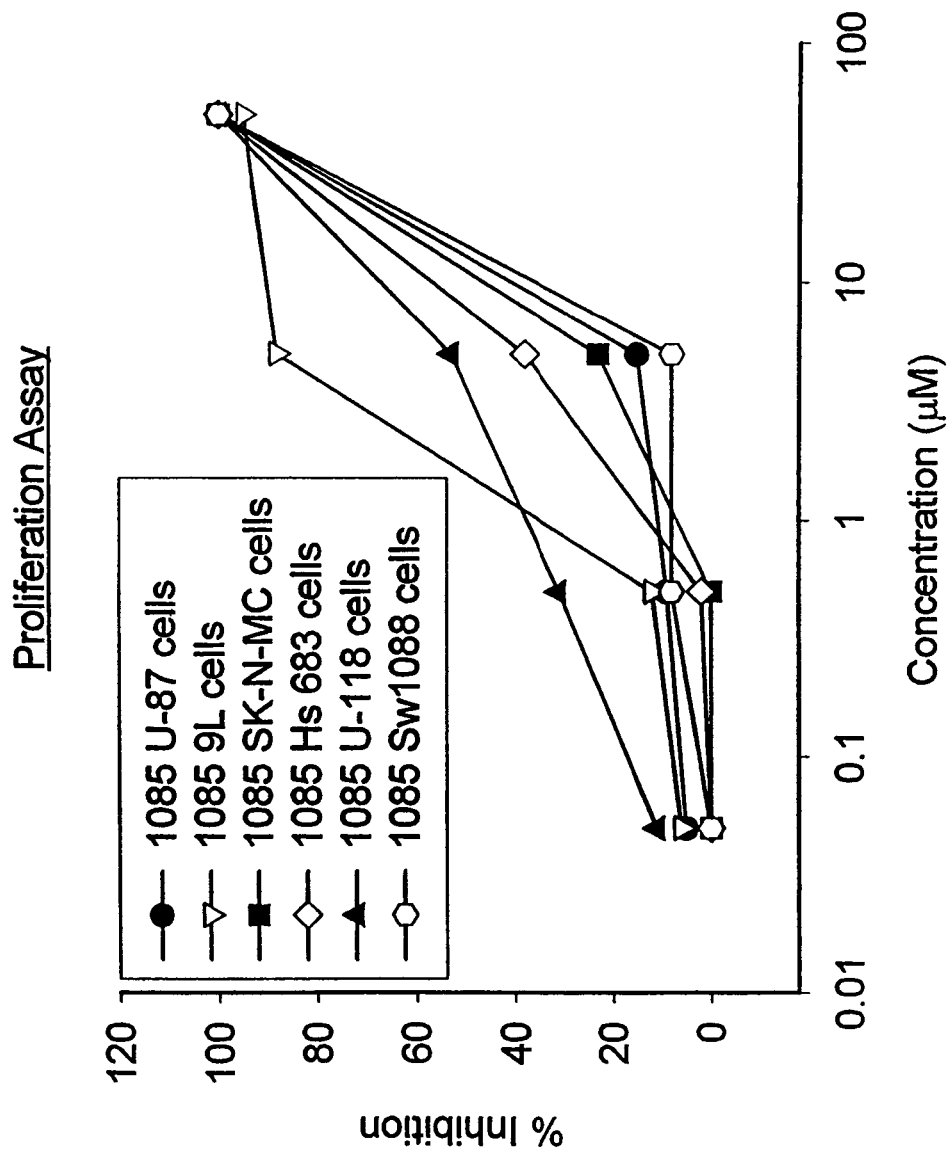
FIG. 14 shows attenuation of brain cancer cell growth when the cells are treated with various compounds of the present invention. Compound 60 was very active in the cell proliferation assay. Compound 60 demonstrated growth inhibition activity at 5 µM in all cell lines tested (15-88%), and strong growth inhibition at 50 µM in all cell lines (95-100%).
Figure 15:
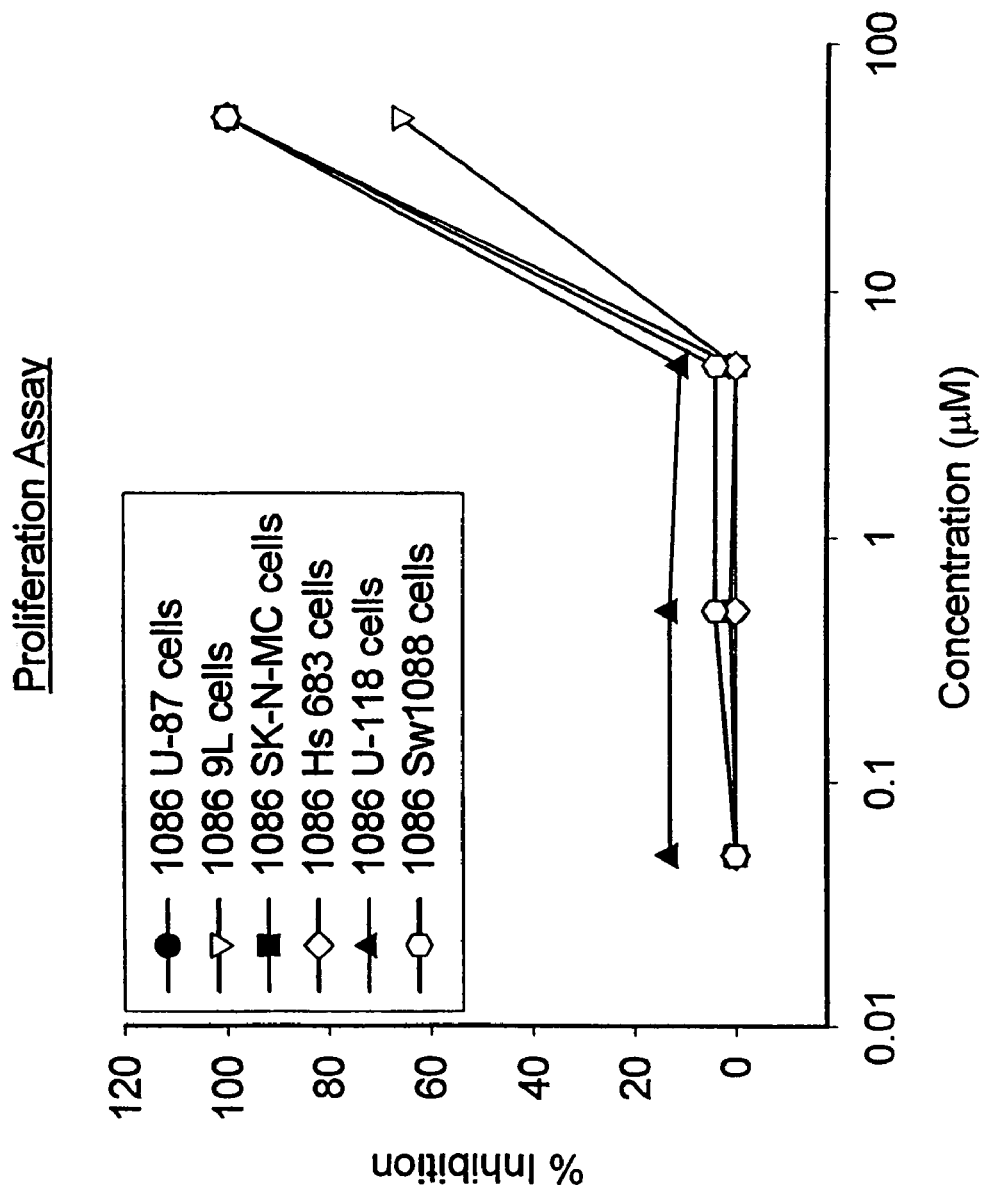
FIG. 15 shows attenuation of brain cancer cell growth when the cells are treated with various compounds of the present invention. Compound 61, at 50 µM, inhibits growth of all cell lines 66-100%.
Figure 16A:
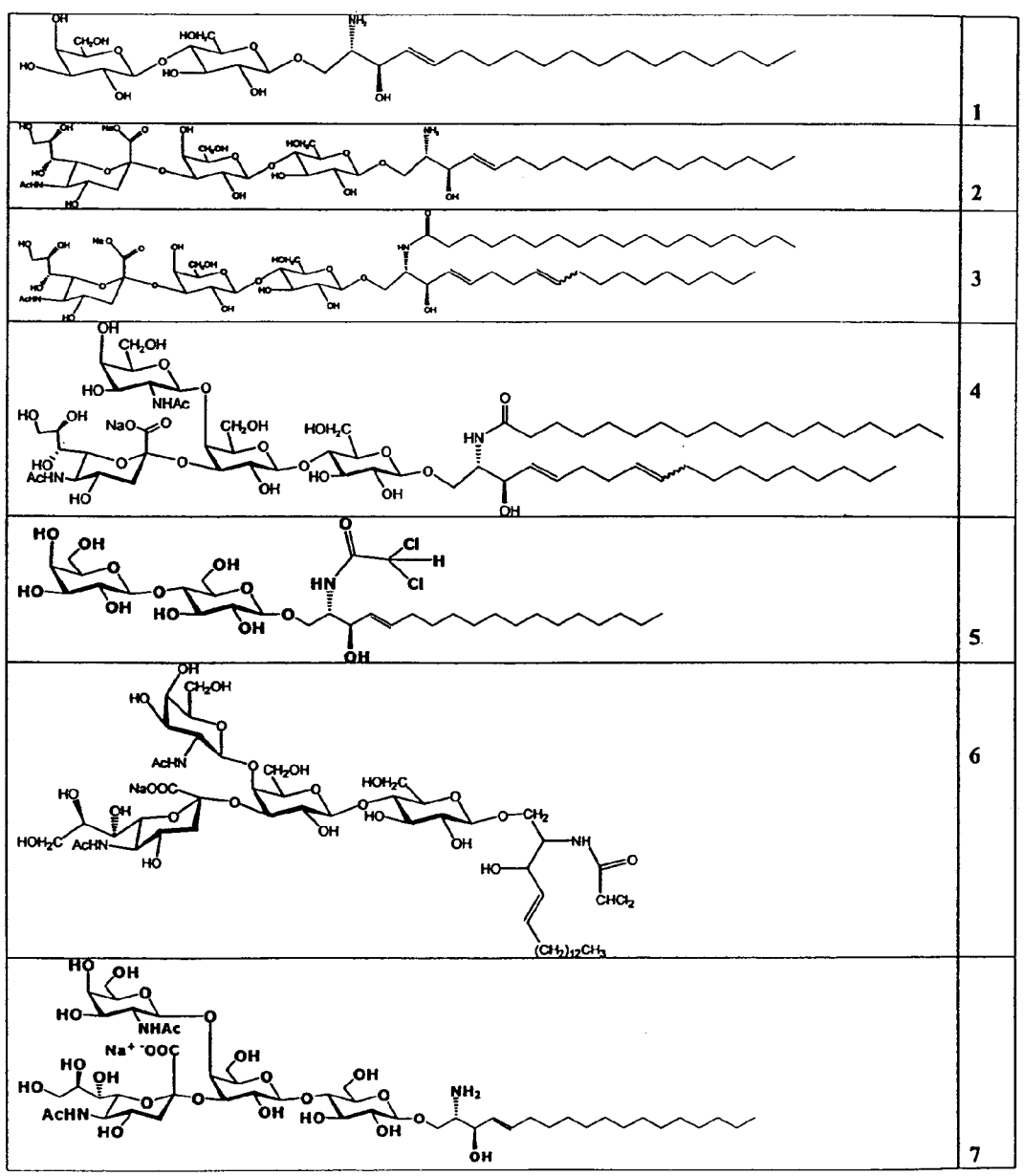
FIG. 16 is a table of representative compounds of the invention.
Figure 16B:
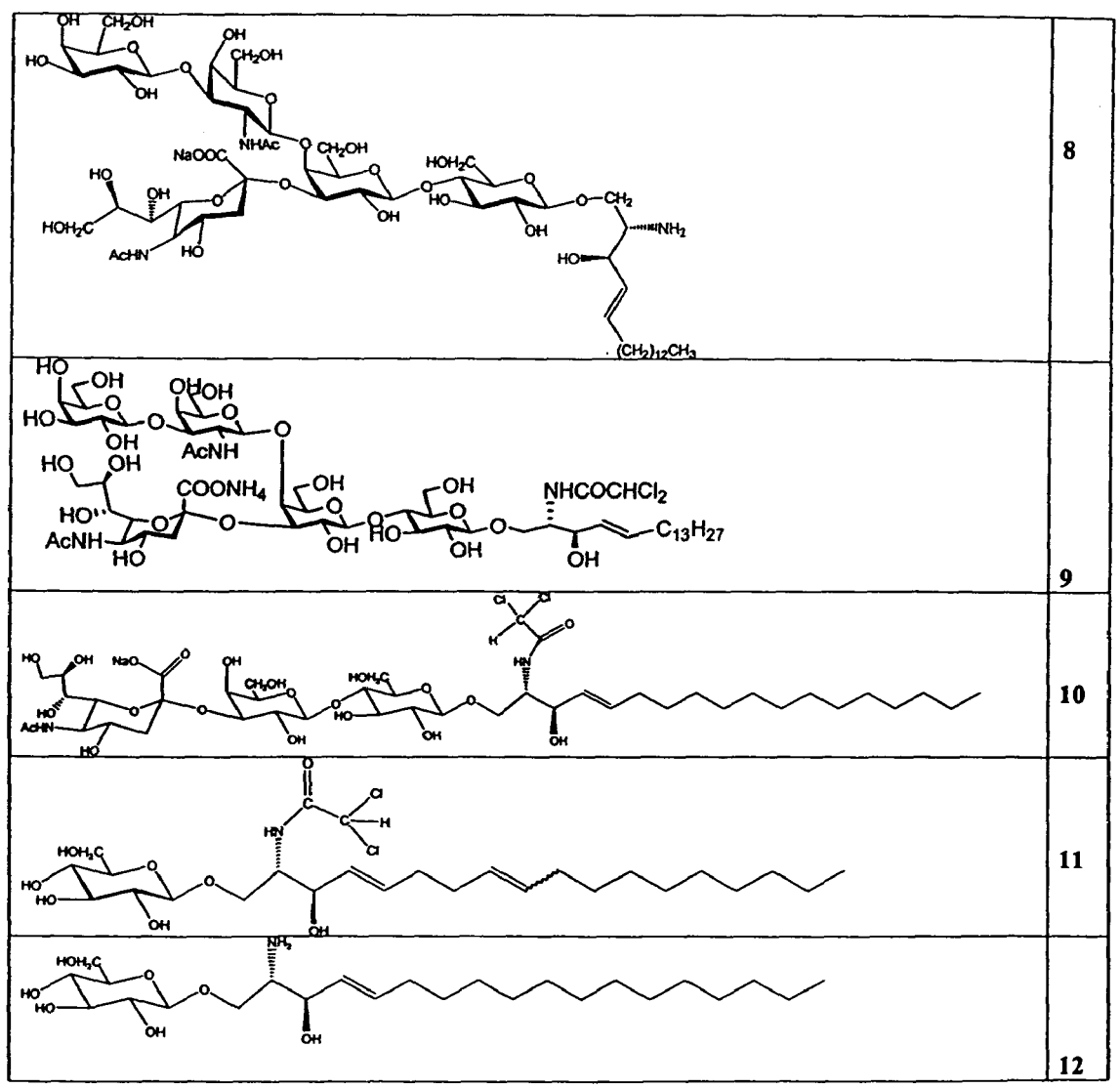
Figure 16C:
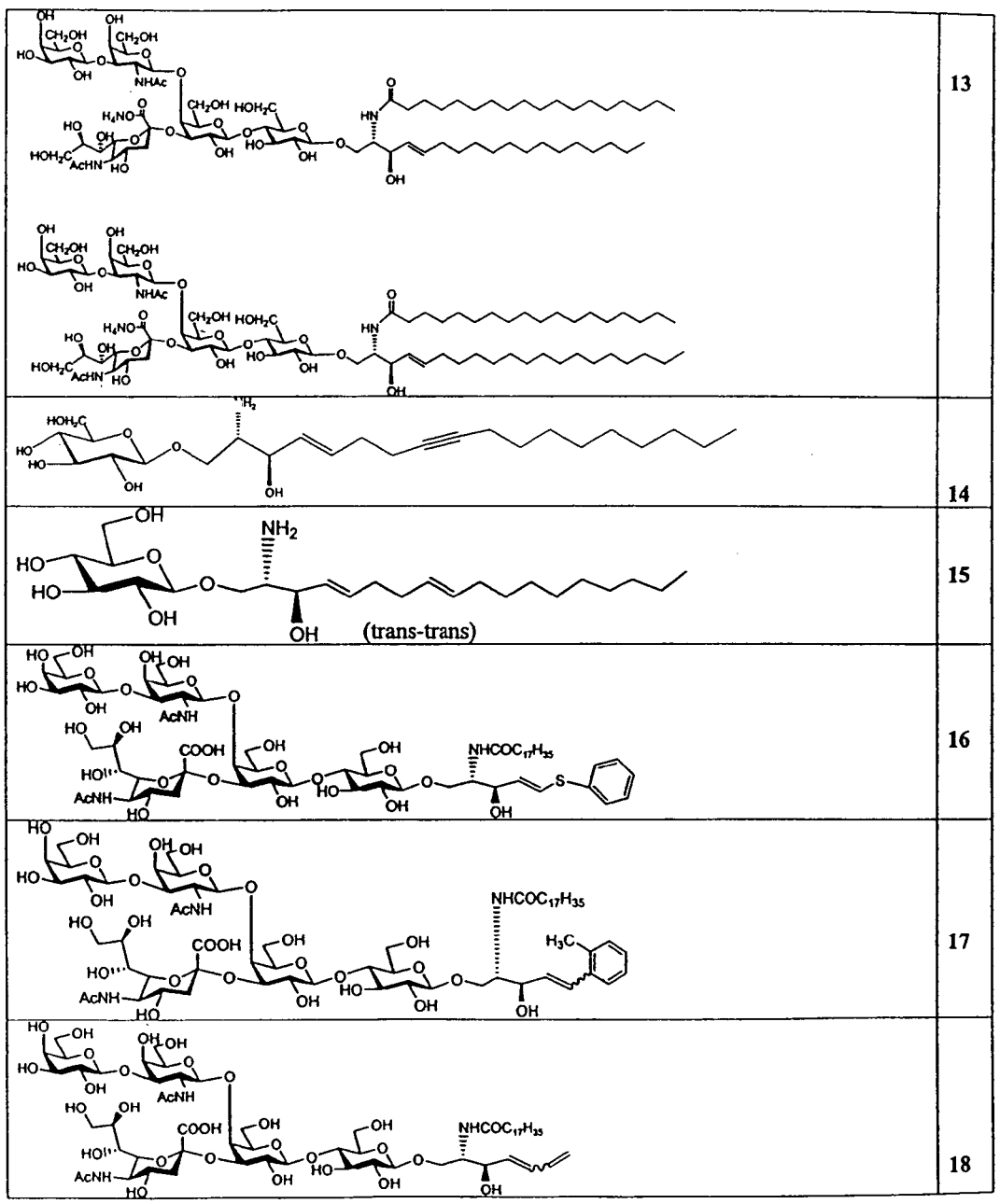
Figure 16D:
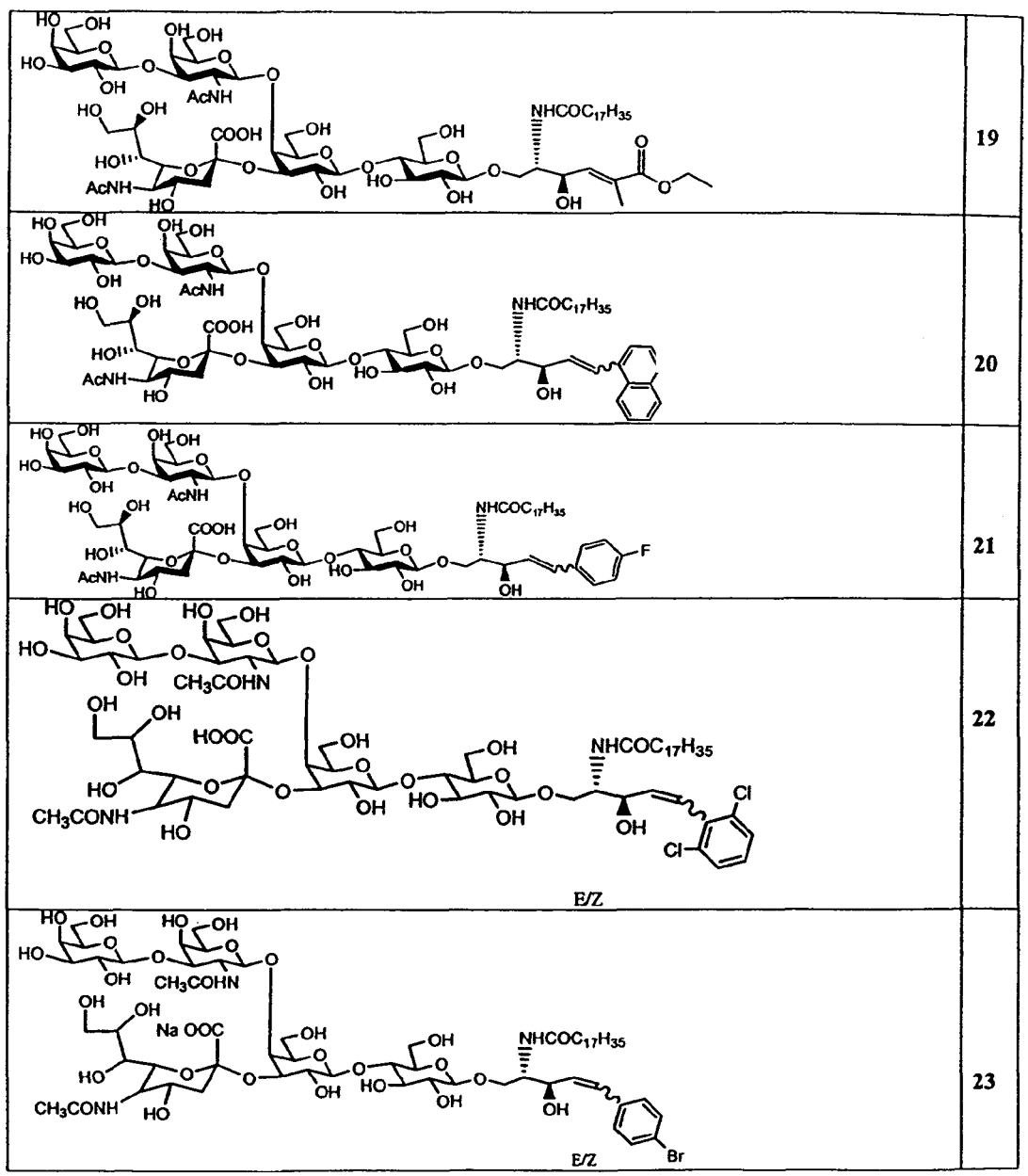
Figure 16E:
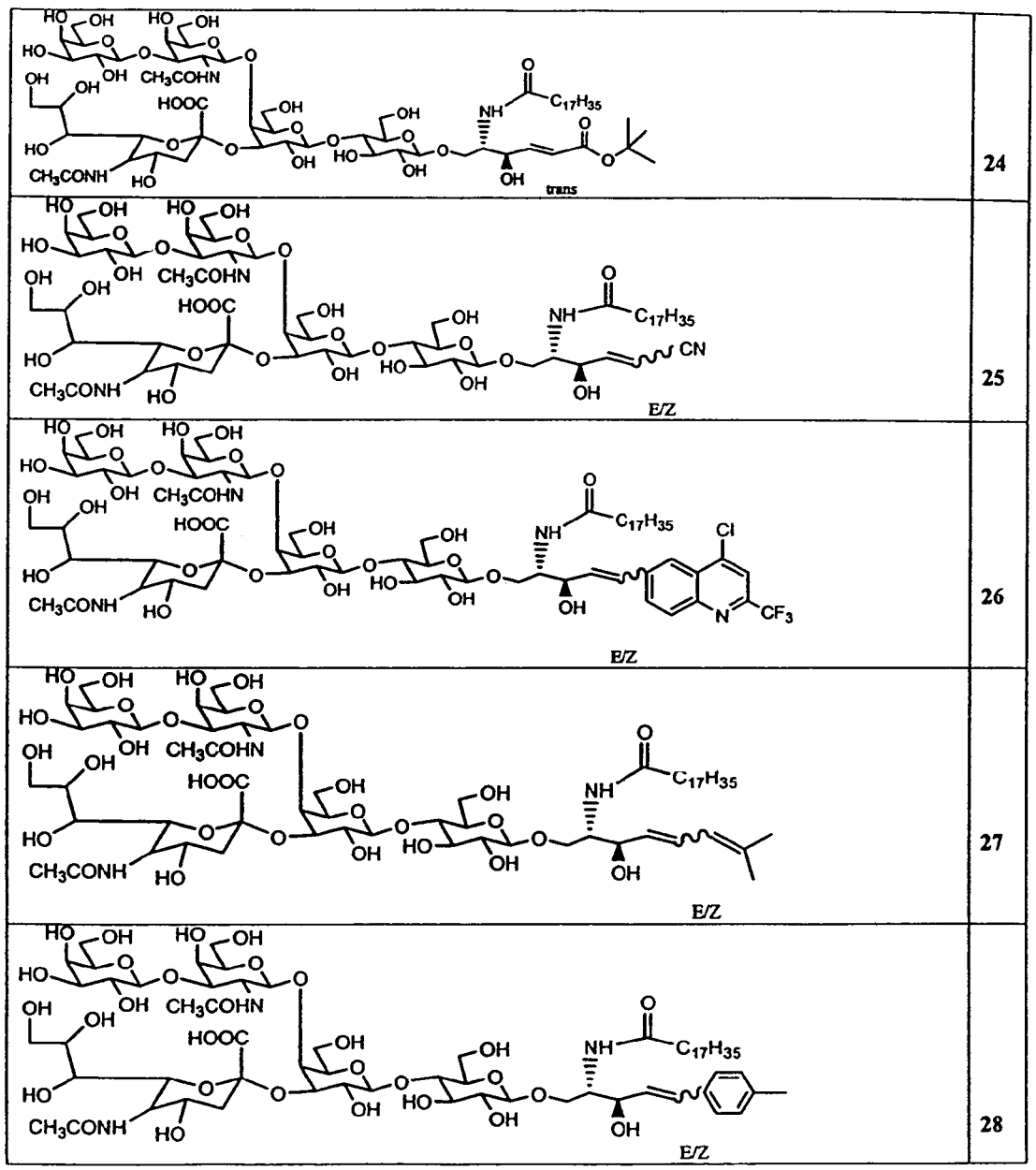
Figure 16F:
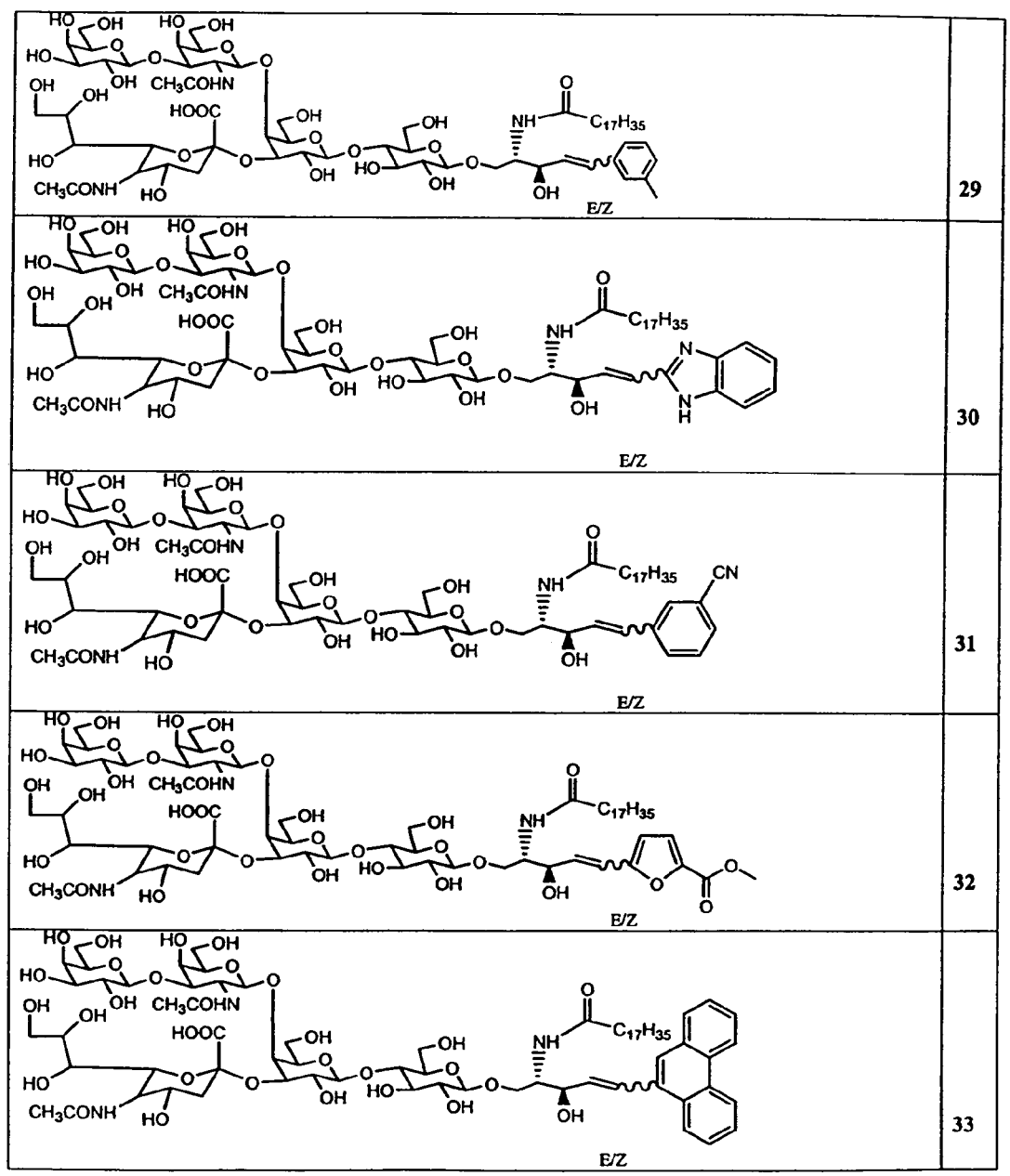
Figure 16G:
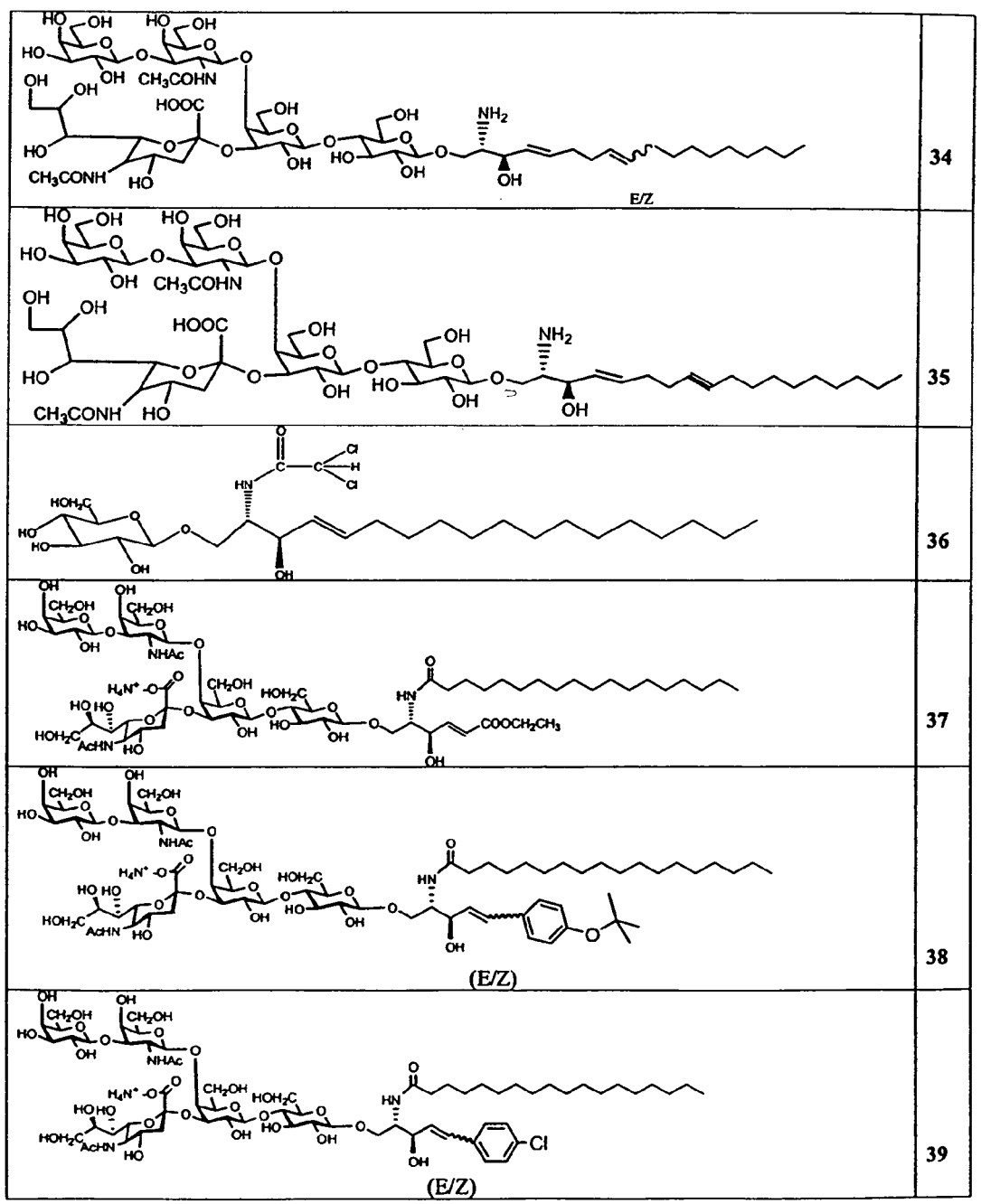
Figure 16H:
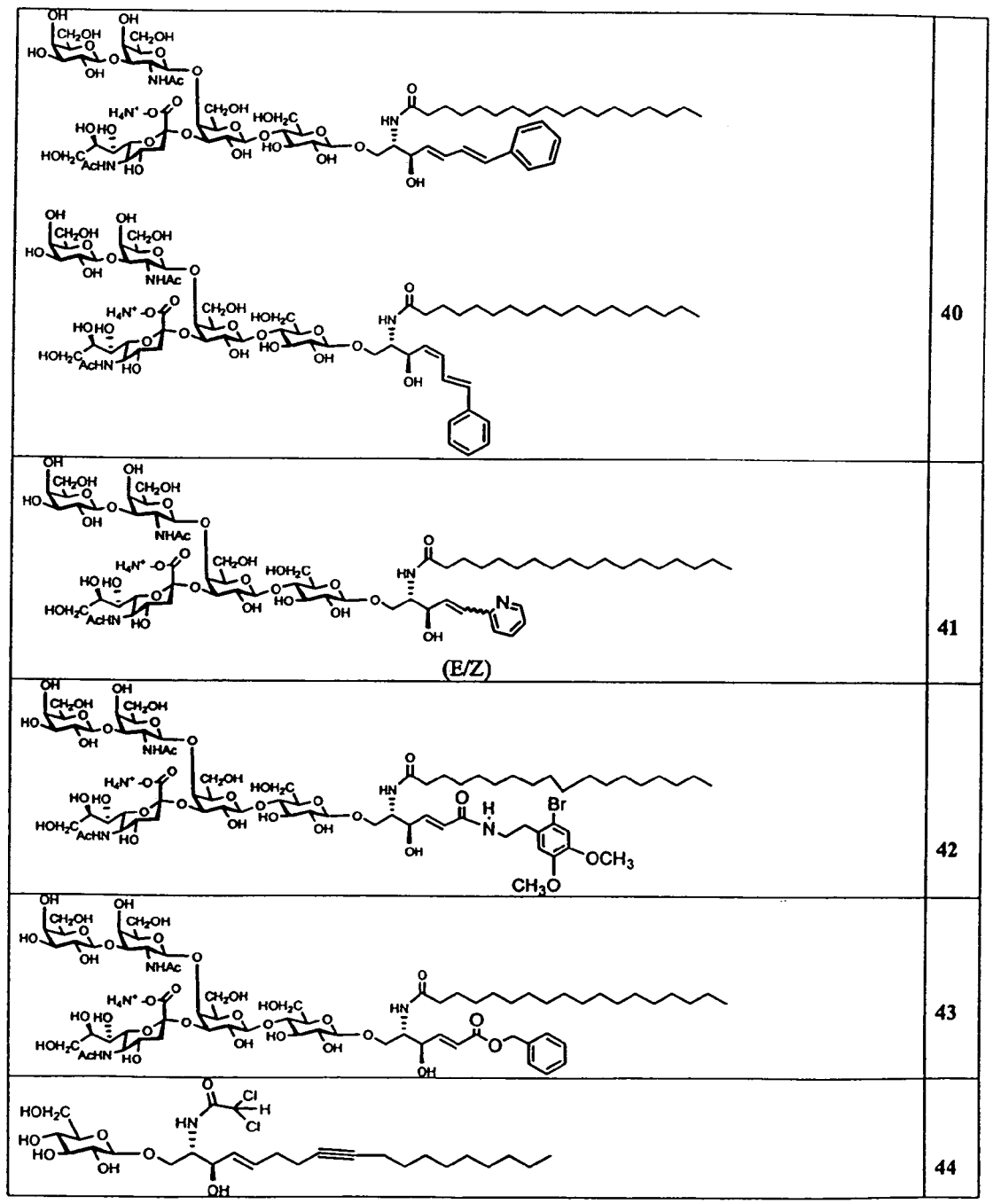
Figure 16I:
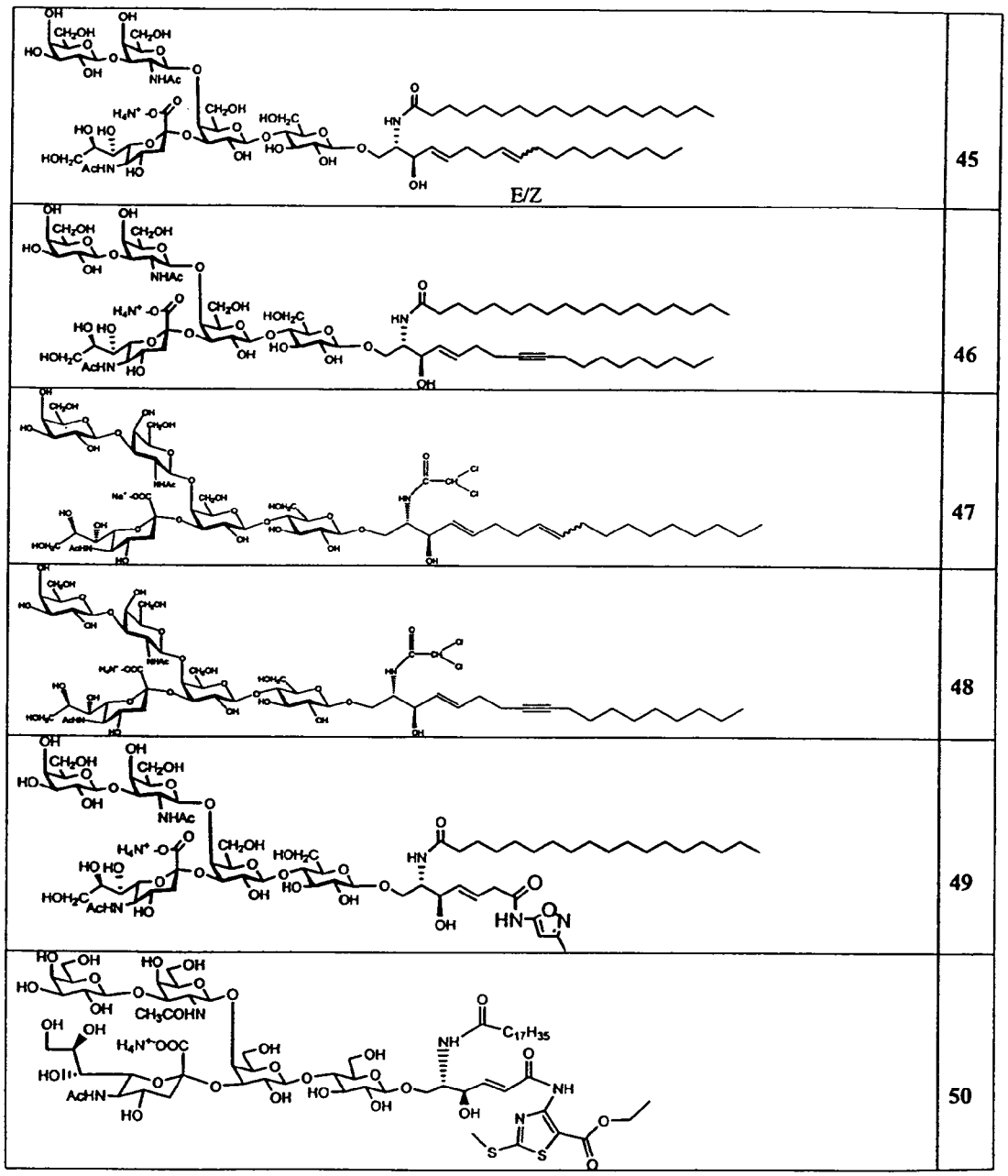
Figure 16J:
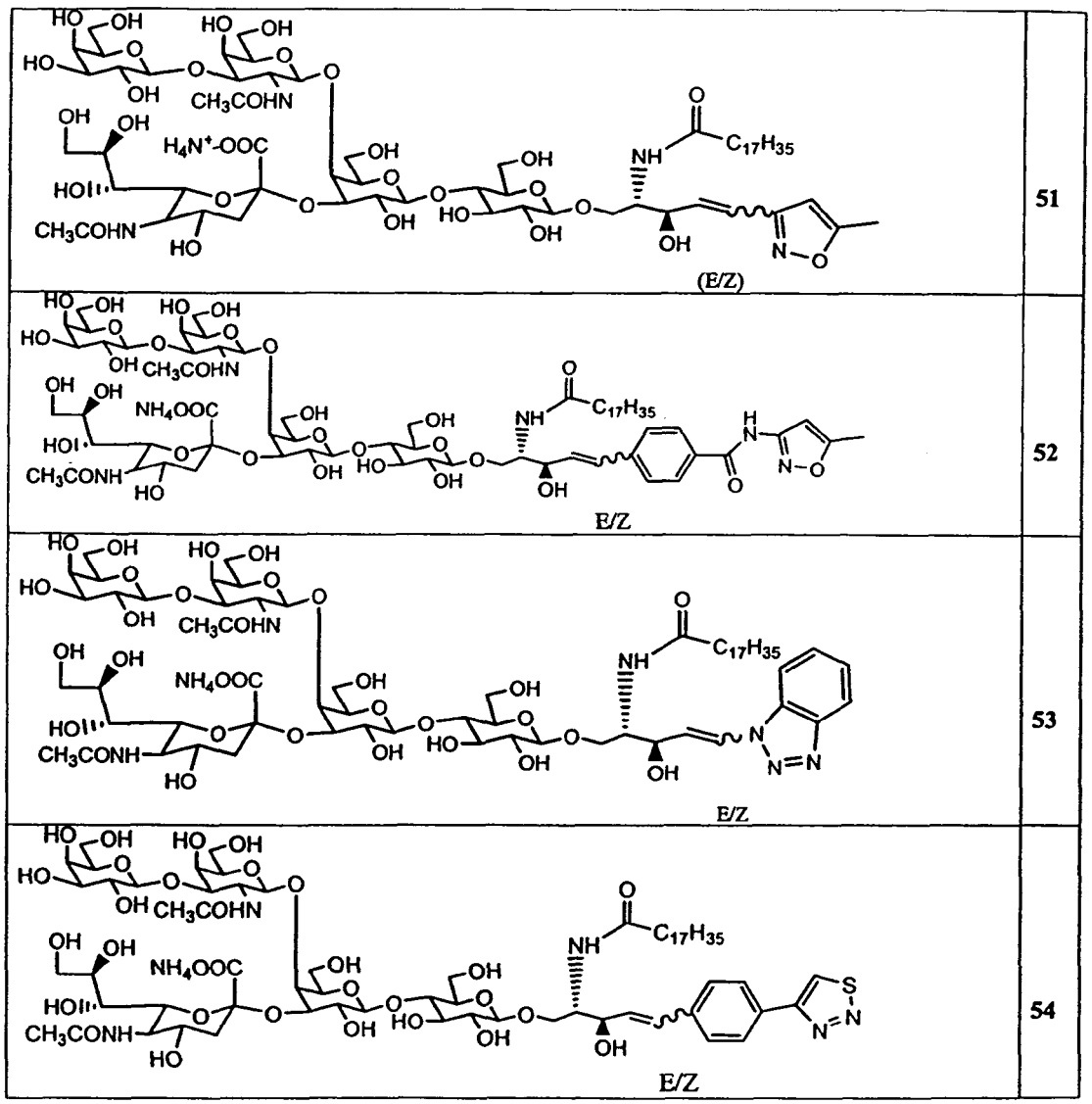
Figure 16K:
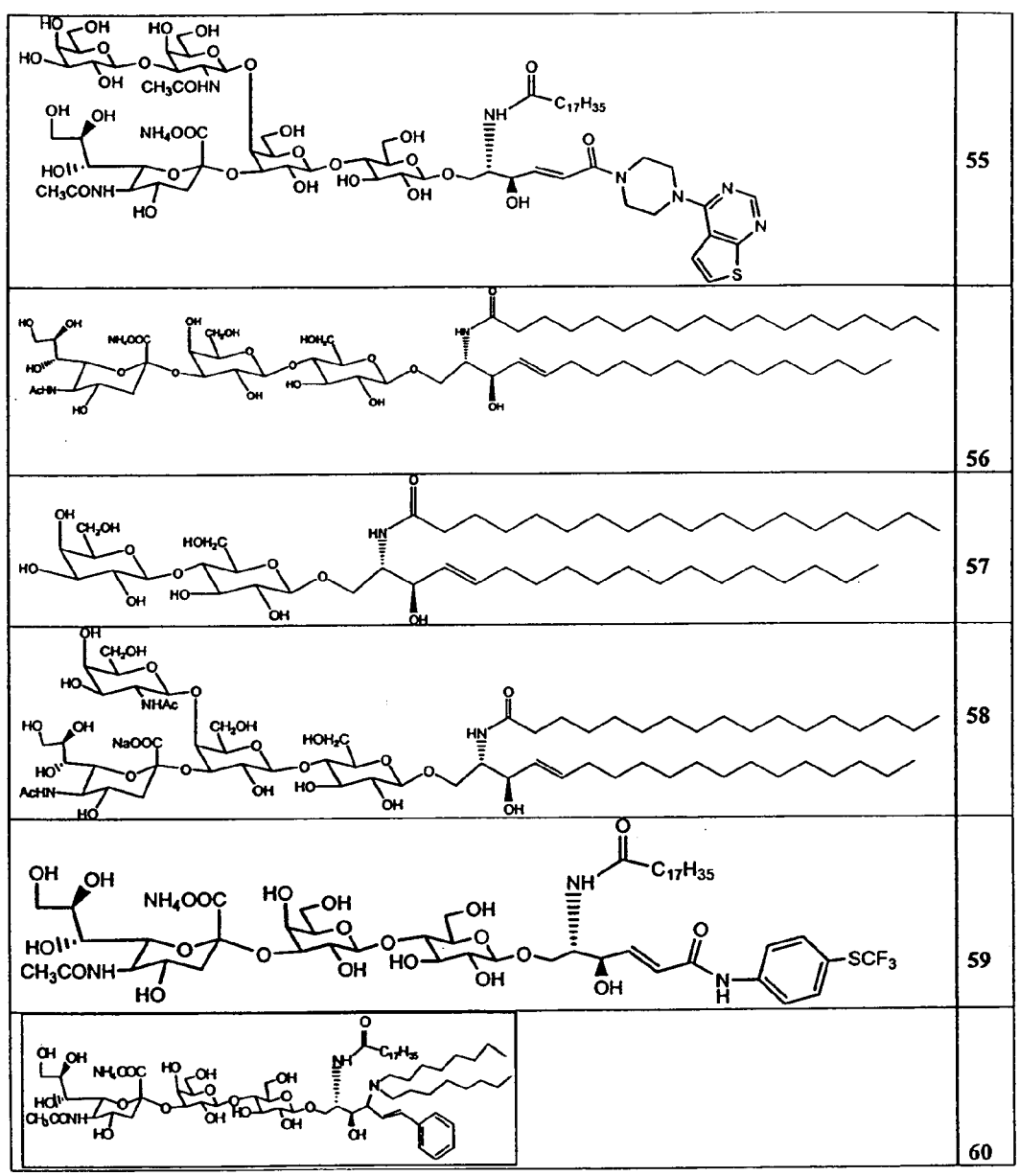
Figure 16L:
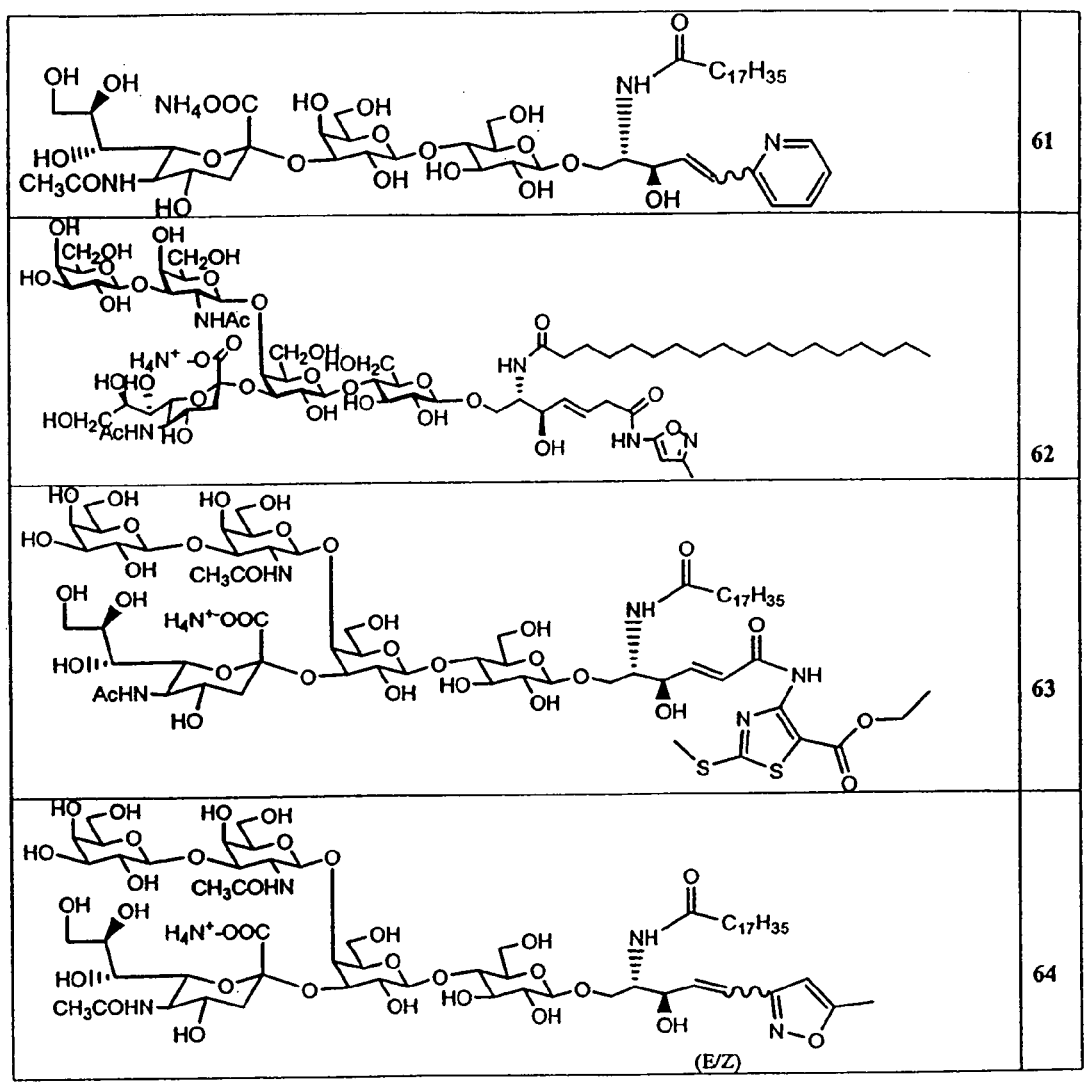
Figure 16M:
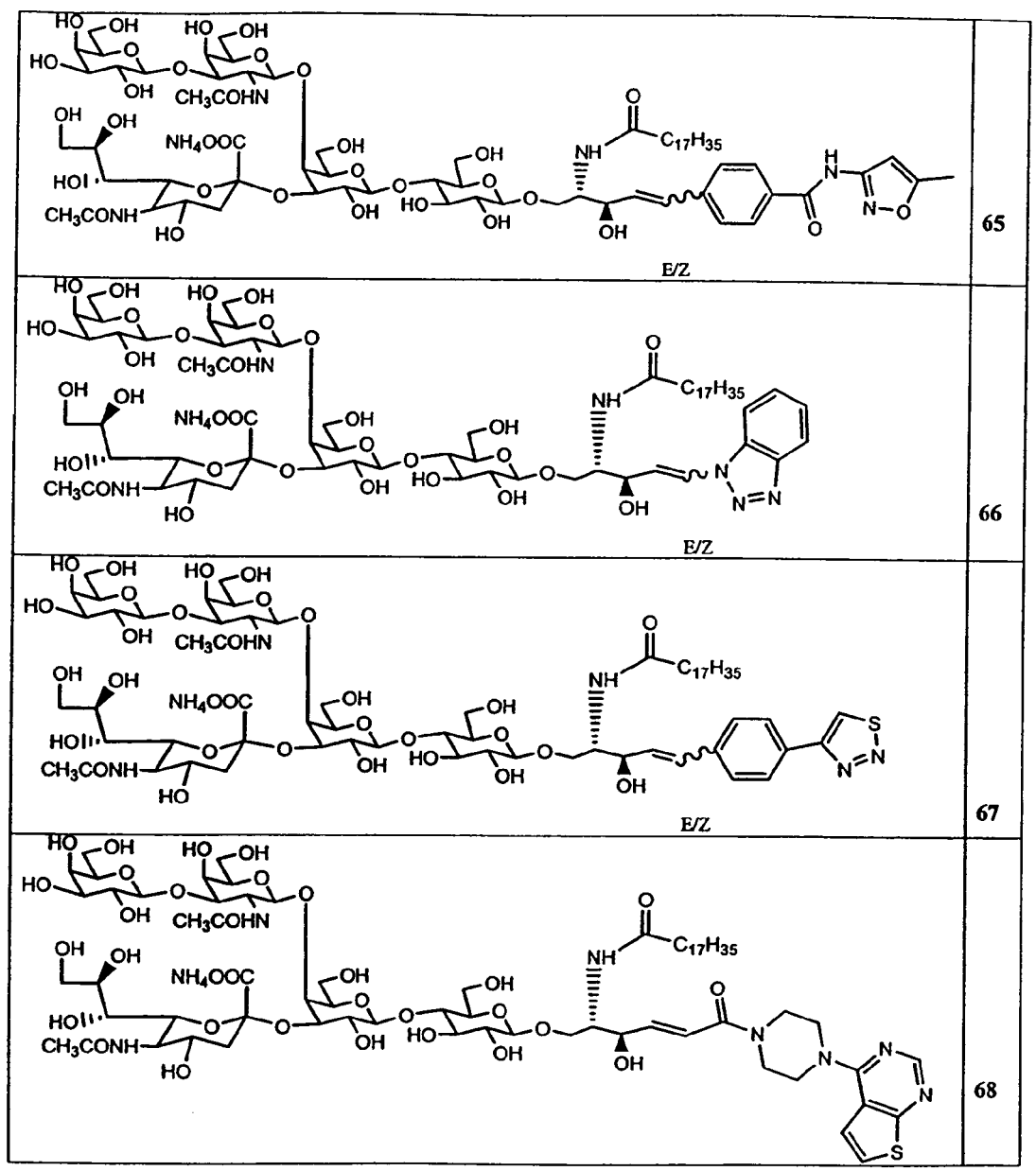
Figure 16N:
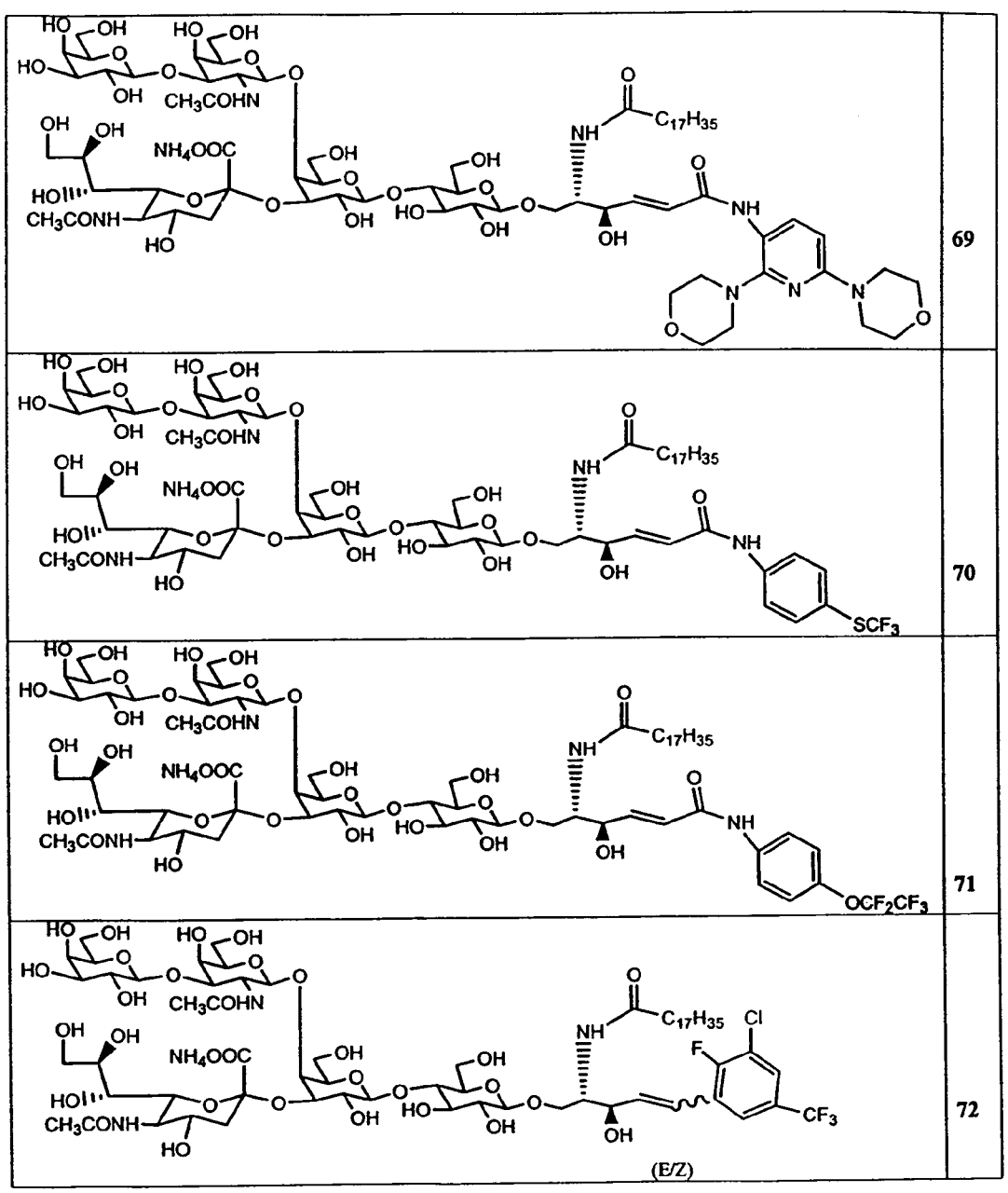
Figure 16O:
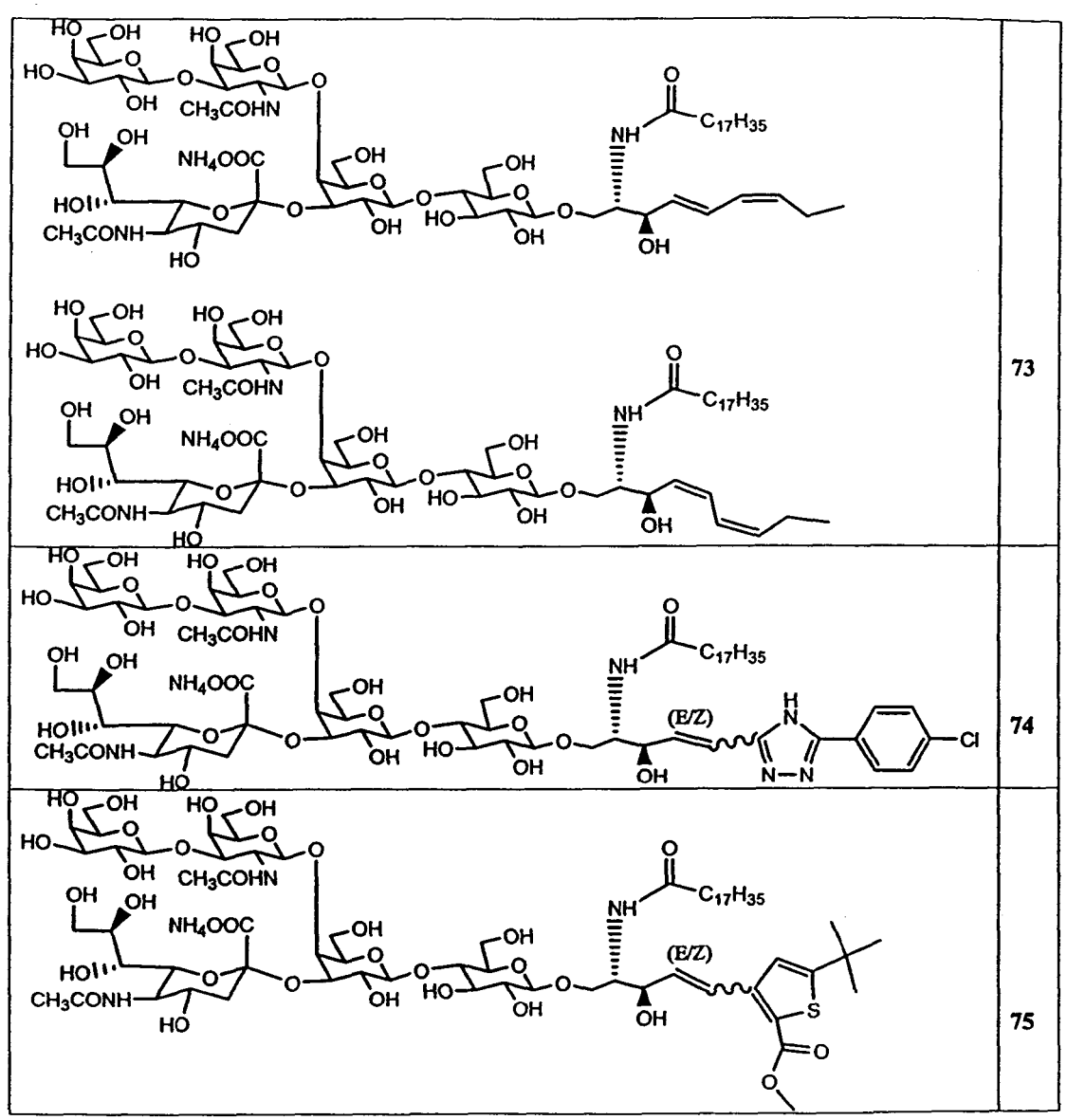
Figure 16P:
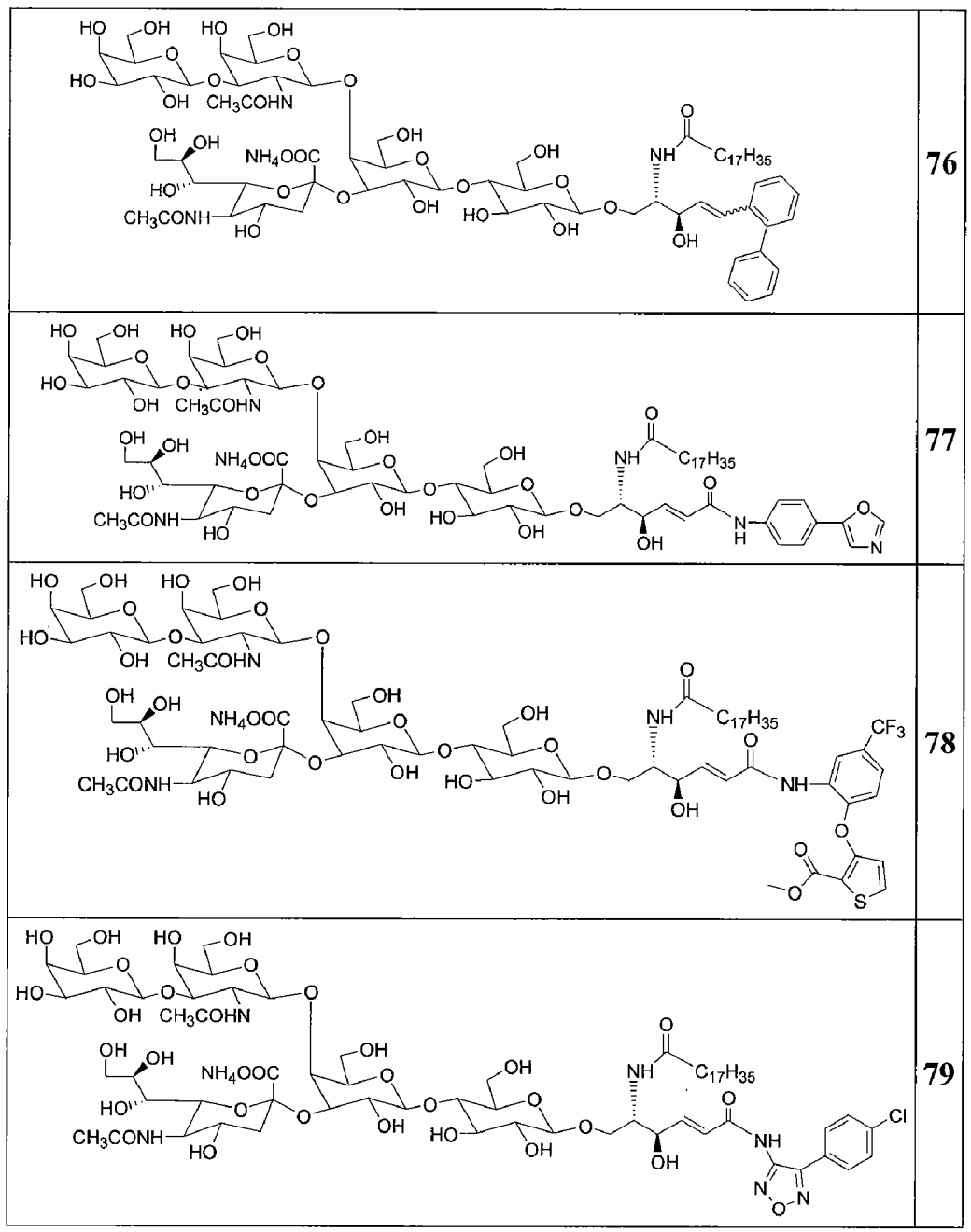
Figure 16Q:
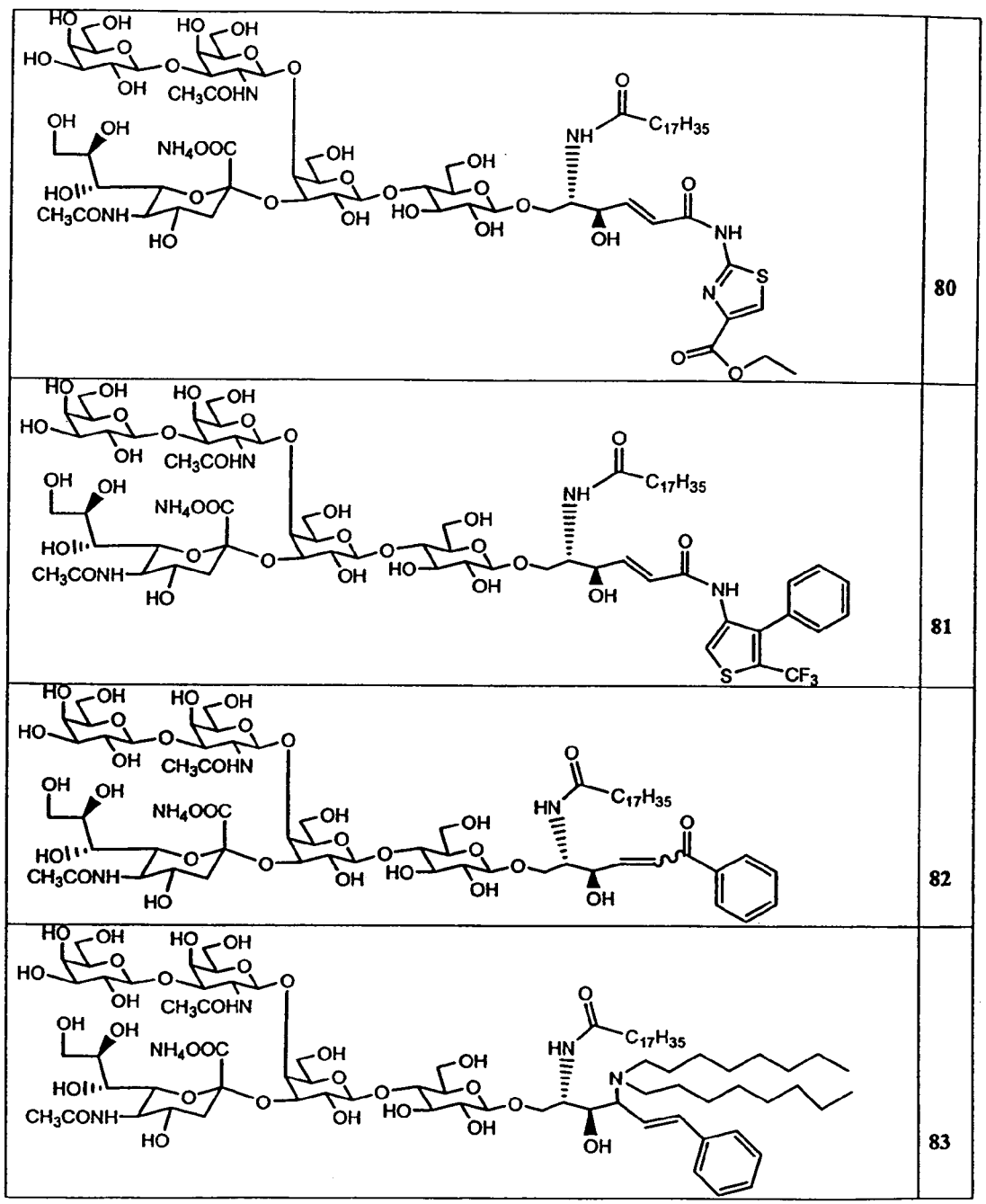
Figure 16R:
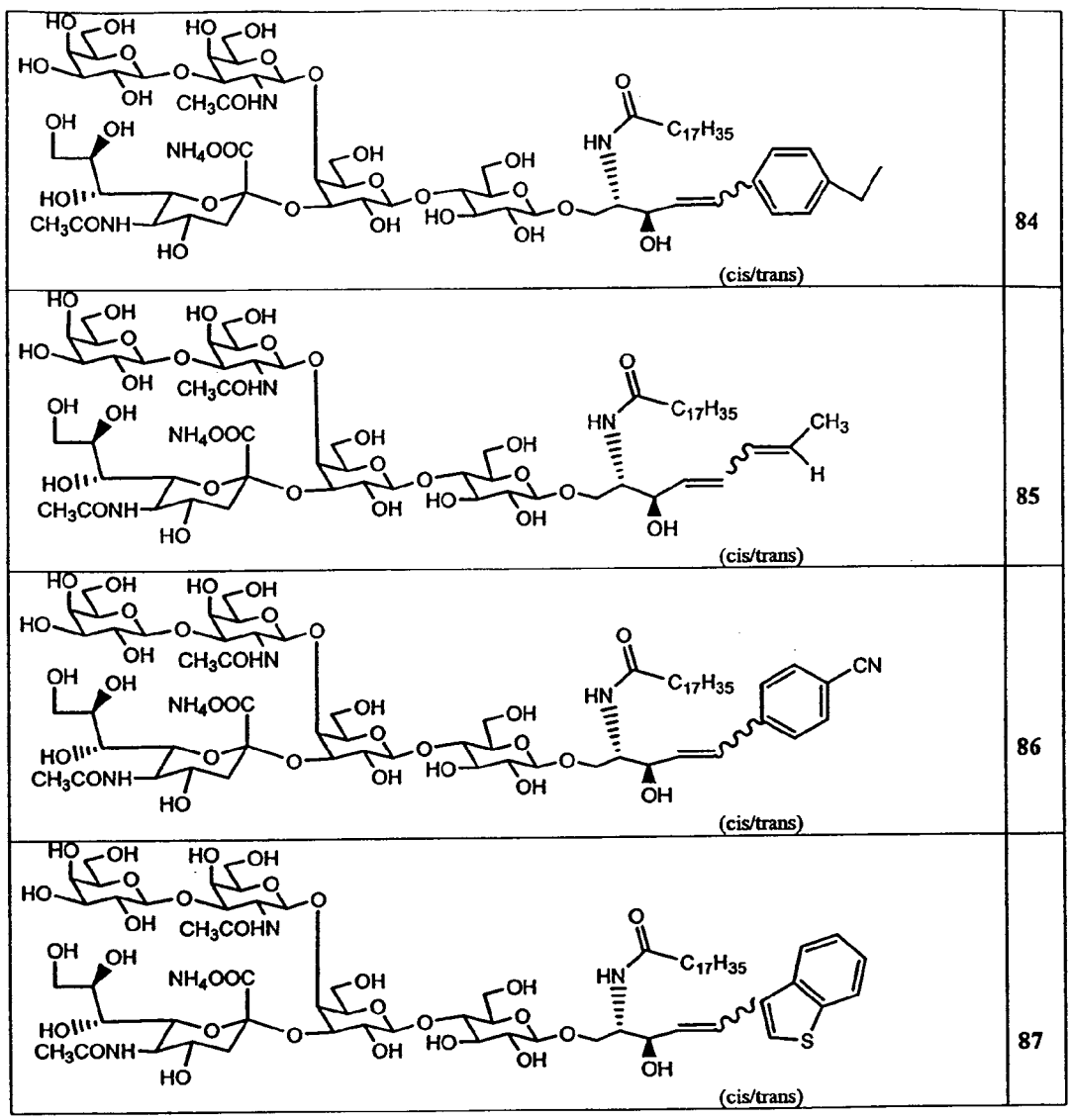
Figure 16S:
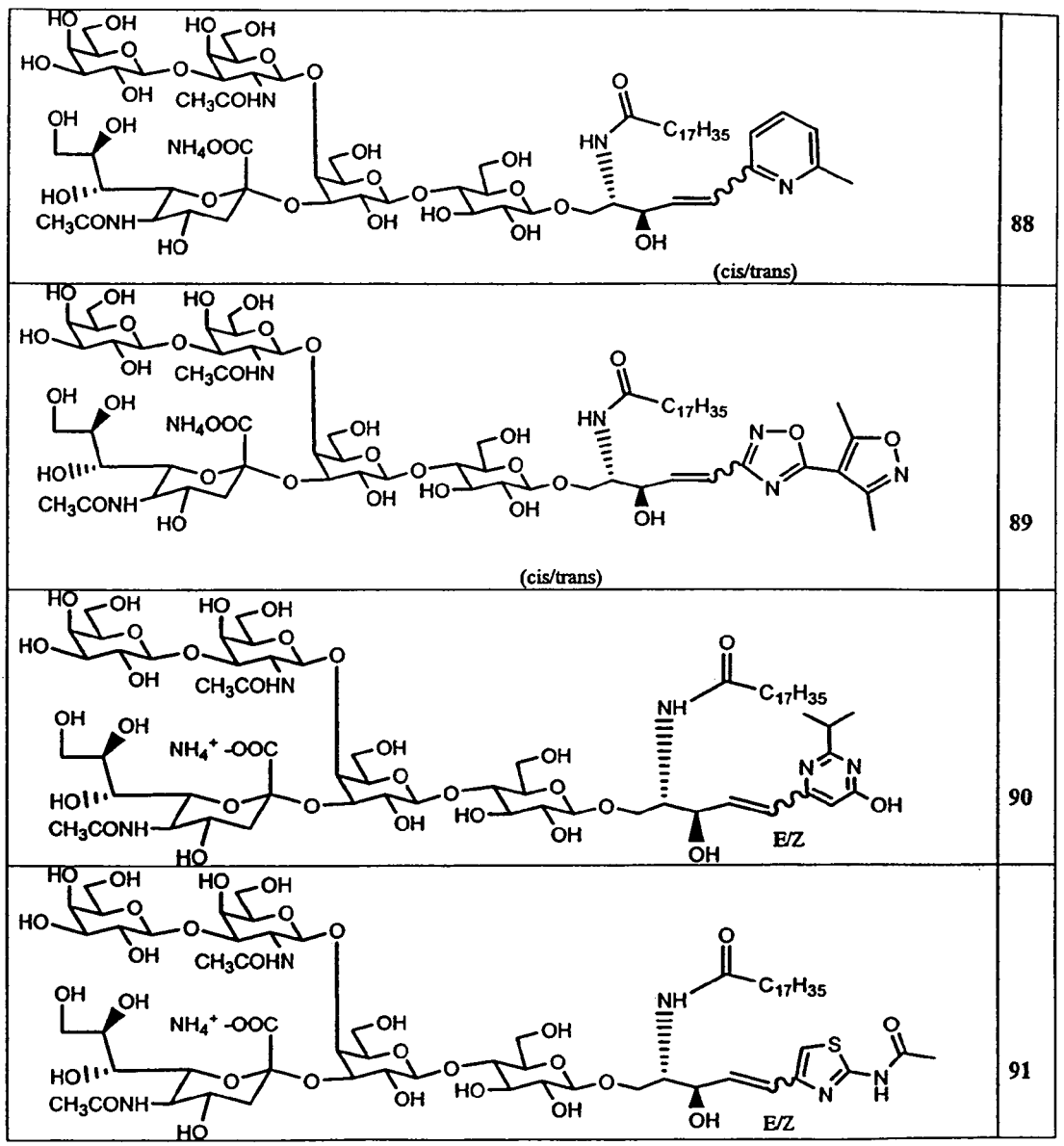
Figure 16T:
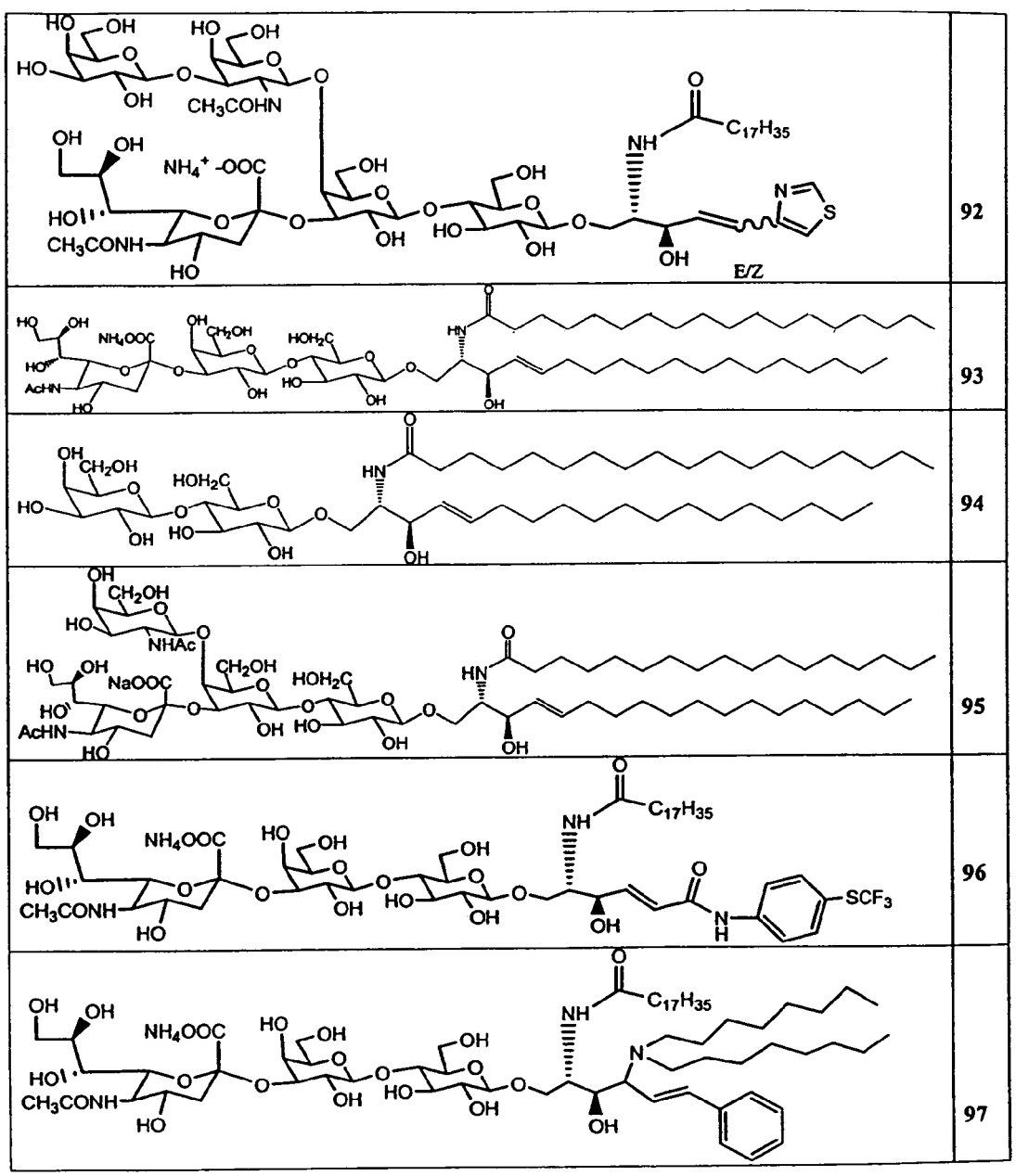
Figure 16U:
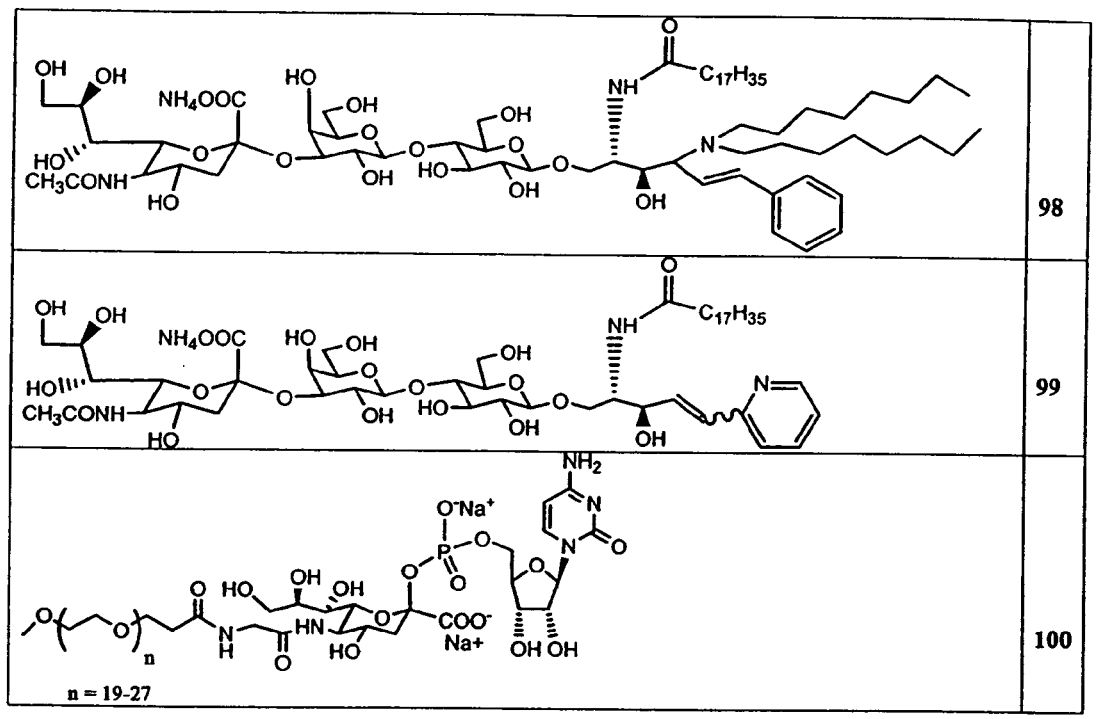
Figure 17:
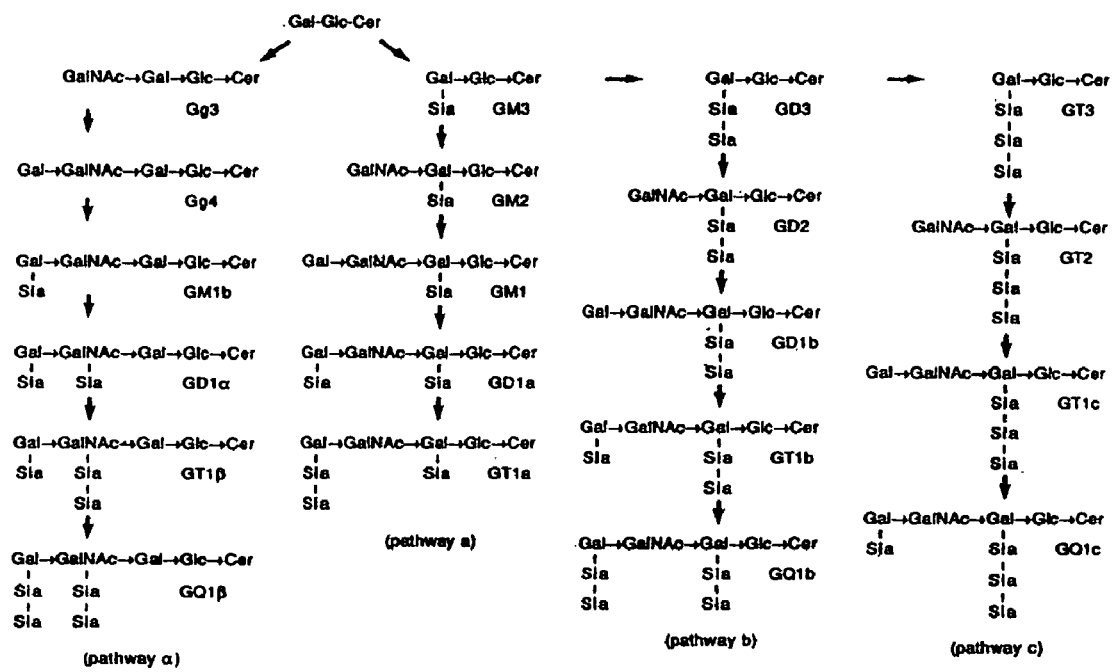
FIG. 17 is a table of representative saccharide moieties that are included in the compounds of the invention.

An additional scheme is provided in FIG. 5. A glycosyl ceramide is hydrolyzed to the corresponding sphingosine, which is contacted with a sialyltransferase. The sialylated compound is treated with a GalNAc transferase and a GalNAC donor. The resulting compound is converted into a ceramide by acylation of the amine moiety with an activated carboxylic acid derivative.

The Enzymes
  a. Glycosyltransferases and Methods for preparing Substrates Having Selected Glycosylation Patterns The methods of the invention utilize glycosyltransferases (e.g., fucosyltransferases) that are selected for their ability to produce saccharides having a selected glycosylation pattern. For example, glycosyltransferases are selected that not only have the desired specificity, but also are capable of glycosylating a high percentage of desired acceptor groups in the substrate. It is preferable to select the glycosyltransferase based upon results obtained using an assay system that employs an oligosaccharide acceptor moiety, e.g., a soluble oligosaccharide or an oligosaccharide that is attached to a relatively short peptide. In certain embodiments, the glycosyltransferase is a fusion protein. Exemplary fusion proteins include glycosyltransferases that exhibit the activity of two different glycosyltransferases (e.g., sialyltransferase and fucosyltransferase). Other fusion proteins will include two different variations of the same transferase activity (e.g., FucT-VI and FucT-VII). Still other fusion proteins will include a domain that enhances the utility of the transferase activity (e.g, enhanced solubility, stability, turnover, etc.).

A number of methods of using glycosyltransferases to synthesize desired oligosaccharide structures are known and are generally applicable to the instant invention. Exemplary methods are described, for instance, WO 96/32491, Ito et al., Pure Appl. Chem. 65: 753 (1993), and U.S. Pat. Nos. 5,352,670, 5,374,541, and 5,545,553.

Glycosyltransferases catalyze the addition of activated sugars (donor NDP-sugars), in a step-wise fashion, to a substrate (e.g., protein, glycopeptide, lipid, glycolipid or to the non-reducing end of a growing oligosaccharide). A very large number of glycosyltransferases are known in the art.

The method of the invention may utilize any glycosyltransferase, provided that it can add the desired glycosyl residue at a selected site. Examples of such enzymes include galactosyltransferase, N-acetylglucosaminyltransferase, N-acetylgalactosaminyltransferase, facosyltransferase, sialyltransferase, mannosyltransferase, xylosyltransferase, glucosyltransferase, glucurononyltransferase and the like.

The present invention is practiced using a trans-sialidase or a sialyltransferase and a combination of glycosyltransferases. For example, one can use a combination of a sialyltransferase and a galactosyltransferase in addition to the trans-sialidase. In those embodiments using more than one enzyme, more than one enzyme and the appropriate glycosyl donors are optionally combined in an initial reaction mixture. Alternatively, the enzymes and reagents for a subsequent enzymatic reaction are added to the reaction medium once the previous enzymatic reaction is complete or nearly complete. By conducting two enzymatic reactions in sequence in a single vessel, overall yields are improved over procedures in which an intermediate species is isolated. Moreover, cleanup and disposal of extra solvents and by-products is reduced.

Glycosyltransferases that can be employed in the methods of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, and galacturonic acid transferases. Suitable glycosyltransferases include those obtained from eukaryotes, as well as from prokaryotes.

For enzymatic saccharide syntheses that involve glycosyltransferase reactions, glycosyltransferase can be cloned, or isolated from any source. Many cloned glycosyltransferases are known, as are their polynucleotide sequences. See, e.g., "The WWW Guide To Cloned Glycosyltransferases," (http://www.vei.co.uk/TGN/gt guide.htm). Glycosyltransferase amino acid sequences and nucleotide sequences encoding glycosyltransferases from which the amino acid sequences can be deduced are also found in various publicly available databases, including GenBank, Swiss-Prot, EMBL, and others.

DNA encoding the glycosyltransferases may be obtained by chemical synthesis, by screening reverse transcripts of mRNA from appropriate cells or cell line cultures, by screening genomic libraries from appropriate cells, or by combinations of these procedures. Screening of MRNA or genomic DNA may be carried out with oligonucleotide probes generated from the glycosyltransferases gene sequence. Probes may be labeled with a detectable group such as a fluorescent group, a radioactive atom or a chemiluminescent group in accordance with known procedures and used in conventional hybridization assays. In the alternative, glycosyltransferases gene sequences may be obtained by use of the polymerase chain reaction (PCR) procedure, with the PCR oligonucleotide primers being produced from the glycosyltransferases gene sequence. See, U.S. Pat. No. 4,683,195 to Mullis et al. and U.S. Pat. No. 4,683,202 to Mullis.

The glycosyltransferase may be synthesized in host cells transformed with vectors containing DNA encoding the glycosyltransferase. A vector is a replicable DNA construct. Vectors are used either to amplify DNA encoding the glycosyltransferases enzyme and/or to express DNA, which encodes the glycosyltransferases enzyme. An expression vector is a replicable DNA construct in which a DNA sequence encoding the glycosyltransferases enzyme is operably linked to suitable control sequences capable of effecting the expression of the glycosyltransferase in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences that control the termination of transcription and translation. Amplification vectors do not require expression control domains. All that is needed is the ability to replicate in a host, usually conferred by an origin of replication, and a selection gene to facilitate recognition of transformants.

Examples of suitable glycosyltransferases for use in the preparation of the compositions of the invention are described herein. One can readily identify other suitable glycosyltransferases by reacting various amounts of each enzyme (e.g., 1-100 mU/mg protein) with a substrate (e.g., at 1-10 mg/ml) to which is linked an oligosaccharide that has a potential acceptor site for the glycosyltransferase of interest. The abilities of the glycosyltransferases to add a sugar residue at the desired site are compared. Glycosyltransferases showing the ability to glycosylate the potential acceptor sites of substrate-linked oligosaccharides more efficiently than other glycosyltransferases having the same specificity are suitable for use in the methods of the invention.

The amount of a particular enzyme needed to accomplish a desired transformation is readily determined by those of skill in the art. In other embodiments, however, it is desirable to use a greater amount of enzyme. A temperature of about 30 to about 37° C., for example, is suitable.

The efficacy of the methods of the invention can be enhanced through use of recombinantly produced glycosyltransferases. Recombinant production enables production of glycosyltransferases in the large amounts that are required for large-scale substrate modification. Deletion of the membrane-anchoring domain of glycosyltransferases, which renders the glycosyltransferases soluble and thus facilitates production and purification of large amounts of glycosyltransferases, can be accomplished by recombinant expression of a modified gene encoding the glycosyltransferases. For a description of methods suitable for recombinant production of glycosyltransferases see, U.S. Pat. No. 5,032,519.

Also provided by the invention are glycosylation methods in which the target substrate is immobilized on a solid support. The term "solid support" also encompasses semi-solid supports. Preferably, the target substrate is reversibly immobilized so that the substrate can be released after the glycosylation reaction is completed. Suitable matrices are known to those of skill in the art. Ion exchange, for example, can be employed to temporarily immobilize a substrate on an appropriate resin while the glycosylation reaction proceeds. A ligand that specifically binds to the substrate of interest can also be used for affinity-based immobilization. Antibodies that bind to a substrate of interest are suitable. Dyes and other molecules that specifically bind to a substrate of interest that is to be glycosylated are also suitable.

In an exemplary embodiment, all of the enzymes used, with the exception of the trans-sialidase, are glycosyltransferases. In another exemplary embodiment, one or more enzymes is a glycosidase.

Fucosyltransferase Reactions

Many saccharides require the presence of particular fucosylated structures in order to exhibit biological activity. Intercellular recognition mechanisms often require a fucosylated oligosaccharide. For example, a number of proteins that function as cell adhesion molecules, including P-selectin, E-selectin, bind specific cell surface fucosylated carbohydrate structures, for example, the sialyl Lewis x and the sialyl Lewis a structures. In addition, the specific carbohydrate structures that form the ABO blood group system are fucosylated. The carbohydrate structures in each of the three groups share a Fucα1,2Galβ1-dissaccharide unit. In blood group O structures, this disaccharide is the terminal structure. The group A structure is formed by an α1,3GalNAc transferase that adds a terminal GalNAc residue to the dissacharide. The group B structure is formed by an α1,3Galactosyltransferase that adds terminal galactose residue. The Lewis blood group structures are also fucosylated. For example the Lewis x and Lewis a structures are Galβ1,4(Fucα1,3)GlcNac and Galβ1,4(Fucα1,4)GlcNac, respectively. Both these structures can be further sialylated (NeuAcα2,3-) to form the corresponding sialylated structures. Other Lewis blood group structures of interest are the Lewis y and b structures which are Fucα1,2Galβ1,4 (Fucα1,3)GlcNAcβ-OR and Fucα1,2Galβ1,3(Fucα1,4)GlcNAc—OR, respectively. For a description of the structures of the ABO and Lewis blood group stuctures and the enzymes involved in their synthesis see, *Essenitials of Glycobiology*, Varki et al. eds., Chapter 16 (Cold Spring Harbor Press, Cold Spring Harbor, N.Y., 1999).

Fucosyltransferases have been used in synthetic pathways to transfer a fucose unit from guanosine-5'-diphosphofucose to a specific hydroxyl of a saccharide acceptor. For example, Ichikawa prepared sialyl Lewis-X by a method that involves the fucosylation of sialylated lactosamine with a cloned fucosyltransferase (Ichikawa et al., *J. Am. Chem. Soc.* 114: 9283-9298 (1992)). Lowe has described a method for expressing non-native fucosylation activity in cells, thereby producing fucosylated glycoproteins, cell surfaces, etc. (U.S. Pat. No. 5,955,347).

In one embodiment, the methods of the invention are practiced by contacting a substrate, having an acceptor moiety for a fucosyltransferase, with a reaction mixture that includes a fucose donor moiety, a facosyltransferase, and other reagents required for fucosyltransferase activity. The substrate is incubated in the reaction mixture for a sufficient time and under appropriate conditions to transfer fucose from the facose donor moiety to the fucosyltransferase acceptor moiety. In preferred embodiments, the fucosyltransferase catalyzes the fucosylation of at least 60% of the fucosyltransferase respective acceptor moieties in the composition.

A number of fucosyltransferases are known to those of skill in the art. Briefly, fucosyltransferases include any of those enzymes, which transfer L-fucose from GDP-fucose to a hydroxy position of an acceptor sugar. In some embodiments, for example, the acceptor sugar is a GlcNAc in a Galβ(1→3,4)GlcNAc group in an oligosaccharide glycoside. Suitable fucosyltransferases for this reaction include the known Galβ(1→3,4)GlcNAc α(1→3,4)fucosyltransferase (FucT-III E.C. No. 2.4.1.65) which is obtained from human milk (see, e.g., Palcic et al., *Carboliydrate Res.* 190:1-11 (1989); Prieels, et al., *J. Biol. Chem.* 256:10456-10463 (1981); and Nunez, et al., *Can. J. Chem.* 59:2086-2095 (1981)) and the βGal(1→4) βGlcNAc α(1→3)fucosyltransferases (FucT-IV, FucT-V, FucT-VI, and FucT-VII, E.C. No. 2.4.1.65) which are found in human serum. A recombinant form of βGal(1→3,4) βGlcNAc α(1→3,4)fucosyltransferase is also available (see, Dumas, et al., *Bioorg. Med. Letters* 1: 425-428 (1991) and Kukowska-Latallo, et al., *Genes and Development* 4: 1288-1303 (1990)). Other exemplary fucosyltransferases include α1,2 fucosyltransferase (E.C. No. 2.4.1.69). Enzymatic fucosylation may be carried out by the methods described in Mollicone et al., *Eur. J. Biochem.* 191:169-176 (1990) or U.S. Pat. No. 5,374,655; an α1,3-fucosyltransferase from *Schistosoma mansoni* (Trottein et al. (2000) *Mol. Biochem. Parasitol.* 107: 279-287); and an α1,3 fucosyltransferase IX (nucleotide sequences of human and mouse FucT-IX are described in Kaneko et al. (1999) *FEBS Lett.* 452: 237-242, and the chromosomal location of the human gene is described in Kaneko et al. (1999) *Cytogenet. Cell Genet.* 86: 329-330. Recently reported α1,3-fucosyltransferases that use an N-linked GlcNAc as an acceptor from the snail *Lymnaea stagnalis* and from mung bean are described in van Tetering et al. (1999) *FEBS Lett.* 461: 311-314 and Leiter et al. (1999) *J. Biol. Chem.* 274: 21830-21839, respectively. In addition, bacterial fucosyltransferases such as the α(1,¾) fucosyltransferase of Helicobacter pylori as described in Rasko et al. (2000) *J. Biol. Chem.* 275:4988-94, as well as the α1,2-fucosyltransferase of *H. Pylori* (Wang et al. (1999) *Microbiology.* 145: 3245-53. See, also Staudacher, E. (1996) *Trends in Glycoscience and Glycotechnology,* 8: 391-408 for description of fucosyltransferases useful in the invention.

Suitable acceptor moieties for fucosyltransferase-catalyzed attachment of a fucose residue include, but are not limited to, GlcNAc—OR, Galβ1,3GlcNAc—OR, NeuAcα2, 3Galβ1,3GlcNAc—OR, Galβ1,4GlcNAc—OR and NeuAcα2,3Galβ1,4GlcNAc—OR, where R is an amino acid, a saccharide, an oligosaccharide or an aglycon group having at least one carbon atom. R is linked to or is part of a substrate. The appropriate fucosyltransferase for a particular reaction is chosen based on the type of fucose linkage that is desired (e.g., α2, α3, or α4), the particular acceptor of interest, and the ability of the fucosyltransferase to achieve the desired high yield of fucosylation. Suitable fucosyltransferases and their properties are described above.

If a sufficient proportion of the substrate-linked oligosaccharides in a composition does not include a fucosyltransferase acceptor moiety, one can synthesize a suitable acceptor. For example, one preferred method for synthesizing an acceptor for a fucosyltransferase involves use of a GlcNAc transferase to attach a GlcNAc residue to a GlcNAc transferase acceptor moiety, which is present on the substrate-linked oligosaccharides. In preferred embodiments a transferase is chosen, having the ability to glycosylate a large fraction of the potential acceptor moieties of interest. The resulting GlcNAcβ-OR can then be used as an acceptor for a fucosyltransferase.

The resulting GlcNAcβ-OR moiety can be galactosylated prior to the fucosyltransferase reaction, yielding, for example, a Galβ1,3GlcNAc—OR or Gal β1,4GlcNAc—OR residue. In some embodiments, the galactylation and fucosylation steps can be carried out simultaneously. By choosing a fucosyltransferase that requires the galactosylated acceptor, only the desired product is formed. Thus, this method involves:

(a) galactosylating a compound of the formula GlcNAcβ-OR with a galactosyltransferase in the presence of a UDP-galactose under conditions sufficient to form the compounds Galβ1,4GlcNAcβ-OR or Galβ1,3GlcNAc—OR; and (b) fucosylating the compound formed in (a) using a fucosyltransferase in the presence of GDP-fucose under conditions sufficient to form a compound selected from:

Fucα1,2Galβ1,4GlcNAc1β-O1R;
Fucα1,2Galβ1,3GlcNAc—OR;
Fucα1,2Galβ1,4GalNAc1β-O1R;
Fucα1,2Galβ1,3GalNAc—OR;
Galβ1,4(Fuc1,α3)GlcNAcβ-OR; or
Galβ1,3(Fucα1,4)GlcNAc—OR.

One can add additional fucose residues to the above structures by including an additional fucosyltransferase, which has the desired activity. For example, the methods can form oligosaccharide determinants such as Fucα1,2Galβ1,4 (Fucα1,3)GlcNAcβ-OR and Fucα1,2Galβ1,3(Fucα1,4) GlcNAc—OR. Thus, in another preferred embodiment, the method includes the use of at least two fucosyltransferases. The multiple fucosyltransferases are used either simultaneously or sequentially. When the fucosyltransferases are used sequentially, it is generally preferred that the glycoprotein is not purified between the multiple fucosylation steps. When the multiple fucosyltransferases are used simultaneously, the enzymatic activity can be derived from two separate enzymes or, alternatively, from a single enzyme having more than one fucosyltransferase activity.

Sialyltransferases

Examples of recombinant sialyltransferases, including those having deleted anchor domains, as well as methods of producing recombinant sialyltransferases, are found in, for example, U.S. Pat. No. 5,541,083. At least 15 different mammalian sialyltransferases have been documented, and the cDNAs of thirteen of these have been cloned to date (for the systematic nomenclature that is used herein, see, Tsuji et al. (1996) *Glycobiology* 6: v-xiv). These cDNAs can be used for recombinant production of sialyltransferases, which can then be used in the methods of the invention.

The sialylation can be accomplished using either a trans-sialidase or a sialyltransferase, except where a particular determinant requires an α2,6-linked sialic acid, in which case a sialyltransferase is used. The present methods involve sialylating an acceptor for a sialyltransferase or a trans-sialidase by contacting the acceptor with the appropriate enzyme in the presence of an appropriate donor moiety. For sialyltransferases, CMP-sialic acid is a preferred donor moiety. Trans-sialidases, however, preferably use a donor moiety that includes a leaving group to which the trans-sialidase cannot add sialic acid.

Acceptor moieties of interest include, for example, Galβ-OR. In some embodiments, the acceptor moieties are contacted with a sialyltransferase in the presence of CMP-sialic acid under conditions in which sialic acid is transferred to the non-reducing end of the acceptor moiety to form the compound NeuAcα2,3Galβ-OR or NeuAcα2,6Galβ-OR. In this formula, R is an amino acid, a saccharide, an oligosaccharide or an aglycon group having at least one carbon atom. In an exemplary embodiment, Galβ-OR is Galβ1,4GlcNAc—R, wherein R is linked to or is part of a substrate.

In an exemplary embodiment, the method provides a compound that is both sialylated and fucosylated. The sialyltransferase and fucosyltransferase reactions are generally conducted sequentially, since most sialyltransferases are not active on a fucosylated acceptor. FucT-VII, however, acts only on a sialylated acceptor. Therefore, FucT-VII can be used in a simultaneous reaction with a sialyltransferase.

If the trans-sialidase is used to accomplish the sialylation, the fucosylation and sialylation reactions can be conducted either simultaneously or sequentially, in either order. The substrate to be modified is incubated with a reaction mixture that contains a suitable amount of a trans-sialidase, a suitable sialic acid donor substrate, a fucosyltransferase (capable of making an α1,3 or α1,4 linkage), and a suitable fucosyl donor substrate (e.g., GDP-fucose).

Examples of sialyltransferases that are suitable for use in the present invention include ST3Gal III (e.g., a rat or human ST3Gal III), ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al., *Glycobiology* 6: v-xiv (1996)). An exemplary α(2,3)sialyltransferase referred to as α(2,3)sialyltransferase (EC 2.4.99.6) transfers sialic acid to the non-reducing terminal Gal of a Galβ1→3Glc disaccharide or glycoside. See, Van den Eijnden et al., *J. Biol. Chem.* 256: 3159 (1981), Weinstein et al., *J. Biol. Chem.* 257: 13845 (1982) and Wen et al., *J. Biol. Chem.* 267: 21011 (1992). Another exemplary α2,3-sialyltransferase (EC 2.4.99.4) transfers sialic acid to the non-reducing terminal Gal of the disaccharide or glycoside. see, Rearick et al., *J. Biol. Chem.* 254: 4444 (1979) and Gillespie et al., *J. Biol. Chem.* 267: 21004 (1992). Further exemplary enzymes include Gal-β-1,4-GlcNAc α-2,6 sialyltransferase (See, Kurosawa et al. *Eur. J. Biochem.* 219: 375-381 (1994)). An α2,8-sialyltransferase can also be used to attach a second or multiple sialic acid residues to substrates useful in methods of the invention. A still further example is the alpha2,3-sialyltransferases from *Streptococcus agalactiae* (ST known as cpsK gene), *Haemophilus ducreyi* (known as 1st gene), *Haemophilus influenza* (known as H10871 gene). See, Chaffin et al., *Mol. Microbiol.*, 45: 109-122 (2002).

An example of a sialyltransferase that is useful in the claimed methods is CST-I from Campylobacter (see, for example, U.S. Pat. Nos. 6,503744, 6,096,529, and 6,210933 and WO99/49051, and published U.S. Pat. Application 2002/2,042,369). This enzyme catalyzes the transfer of sialic acid to the Gal of a Galβ1,4Glc or Galβ1,3GalNAc Other exemplary sialyltransferases of use in the present invention include those isolated from Campylobacter jejuni, including the α(2,3) sialyltransferase. See, e.g, WO99/49051. In another embodiment, the invention provides bifunctional sialyltransferase polypeptides that have both an α2,3 sialyltransferase activity and an α2,8 sialyltransferase activity. The bifunctional sialyltransferases, when placed in a reaction mixture with a suitable saccharide acceptor (e.g., a saccharide having a terminal galactose), and a sialic acid donor (e.g., CMP-sialic acid) can catalyze the transfer of a first sialic acid from the donor to the acceptor in an α2,3 linkage. The sialyltransferase then catalyzes the transfer of a second sialic acid from a sialic acid donor to the first sialic acid residue in an α2,8 linkage. This type of Siaα2,8-Siaα2,3-Gal structure is often found in glycosphingolipids. See, for example, EP Pat. App. No. 1147200.

A recently reported viral α2,3-sialyltransferase is also suitable use in the sialylation methods of the invention (Sujino et al. (2000) *Glycobiology* 10: 313-320). This enzyme, v-ST3Gal I, was obtained from Myxoma virus-infected cells and is apparently related to the mammalian ST3Gal IV as indicated by comparison of the respective amino acid sequences. v-ST3Gal I catalyzes the sialylation of Type I (Galβ1,3-GlcNAc,β1-R), Type II (Galβ1,4GlcNAc-β1-R) and III (Gal β1,3GalNAcβ1-R) acceptors. The enzyme can also transfer sialic acid to fucosylated acceptor moieties (e.g., Lewis$^x$ and Lewis$^a$).

Galactosyltransferases

In another group of embodiments, the glycosyltransferase is a galactosyltransferase. Exemplary galactosyltransferases include α(1,3) galactosyltransferases (E.C. No. 2.4.1.151, see, e.g., Dabkowski et al., *Transplant Proc.* 25:2921 (1993) and Yamamoto et al. *Nature* 345: 229-233 (1990), bovine (GenBankjO4989, Joziasse et al., *J. Biol. Chem.* 264: 14290-14297 (1989)), murine (GenBank m26925; Larsen et al., *Proc. Nat'l. Acad. Sci. USA* 86: 8227-8231 (1989)), porcine (GenBank L36152; Strahan et al., *Immunogenetics* 41: 101-105 (1995)). Another suitable α1,3Galactosyltransferase is that which is involved in synthesis of the blood group B antigen (EC 2.4.1.37, Yamamoto et al., *J. Biol. Chem.* 265: 1146-1151 (1990) (human)). The present invention can also be practiced using α1,4-galactosyltransferases.

Also suitable for use in the methods of the invention are β(1,4) galactosyltransferases, which include, for example, EC 2.4.1.90 (LacNAc synthetase) and EC 2.4.1.22 (lactose synthetase) (bovine (D'Agostaro et al., *Eur. J. Biochem.* 183: 211-217 (1989)), human (Masri et al., *Biochem. Biophys. Res. Commun.* 157: 657-663 (1988)), murine (Nakazawa et al., J. Biochem. 104: 165-168 (1988)), as well as E.C. 2.4.1.38 and the ceramide galactosyltransferase (EC 2.4.1.45, Stahl et al., *J. Neurosci. Res.* 38: 234-242 (1994)). Other suitable galactosyltransferases include, for example, α1,2 galactosyltransferases (from e.g., *Schizosaccharomyces pombe*, Chapell et al., *Mol. Biol. Cell* 5: 519-528 (1994)). Other 1,4-galactosyltransferases are those used to produce globosides (see, for example, Schaeper, et al. *Carbohydrate Research* 1992, vol. 236, pp. 227-244. Both mammalian and bacterial enzymes are of use.

Other exemplary galactosyltransferases of use in the invention include β1,3-galactosyltransferases. When placed in a suitable reaction medium, the β1,3-galactosyltransferases, catalyze the transfer of a galactose residue from a donor (e.g., UDP-Gal) to a suitable saccharide acceptor (e.g., saccharides having a terminal GalNAc residue). An example of a β1,3-galactosyltransferase of the invention is that produced by *Campylobacter* species, such as *C. jejuni*. A presently preferred β1,3-galactosyl-transferase of the invention is that of *C. jejuni* strain OH4384 as Exemplary linkages in compounds formed by the method of the invention using galactosyltransferases include: (1) Galβ1→4Glc; (2) Galβ1→4GlcNAc; (3) Galβ1→3GlcNAc; (4) Galβ1→6GlcNAc; (5) Galβ1→3GalNAc; (6) Galβ1→6GalNAc; (7) Galα1→3GalNAc; (8) Galα1→3Gal; (9) Galα1→4Gal; (10) Galβ1→3Gal; (11) Galβ1→4Gal; (12) Galβ1→6Gal; (13) Galβ1→4xylose; (14) Galβ1→1'-sphingosine; (15) Galβ1→1'-ceramide; (16) Galβ1→3 diglyceride; (17) Galβ1→O-hydroxylysine; and (18) Gal-S-cysteine. See, for example, U.S. Pat. No. 6,268,193; and 5,691, 180.

Trans-sialidase

As discussed above, the process of the invention involves at least one step in which a sialic acid moiety is added to a substrate using a trans-sialidase. As used herein, the term "trans-sialidase" refers to an enzyme that catalyzes the addition of a sialic acid to galactose through an α-2,3 glycosidic linkage. Trans-sialidases are found in many *Trypanosomy* species and some other parasites. Trans-sialidases of these parasite organisms retain the hydrolytic activity of usual sialidase, but with much less efficiency, and catalyze a reversible transfer of terminal sialic acids from host sialoglycoconjugates to parasite surface glycoproteins in the absence of CMP-sialic acid. *Trypanosonie cruzi*, which causes Chagas disease, has a surface trans-sialidase the catalyzes preferentially the transference of α-2,3-linked sialic acid to acceptors containing terminal β-galactosyl residues, instead of the typical hydrolysis reaction of most sialidases (Ribeirão et al., *Glycobiol.* 7: 1237-1246 (1997); Takahashi et al., *Anal. Biochem.* 230: 333-342 (1995); Scudder et al., *J. Biol. Chem.* 268: 9886-9891 (1993); and Vandekerckhove et al., *Glycobiol.* 2: 541-548 (1992)). *T. cruzi* trans-sialidase (TcTs) has activity towards a wide range of saccharide, glycolipid, and glycoprotein acceptors which terminate with a β-linked galactose residue, and synthesizes exclusively an α2-3 sialosidic linkage (Scudder et al., supra). At a low rate, it also transfers sialic acid from synthetic o-sialosides, such as p-nitrophenyl-β-N-acetylneuraminic acid, but NeuAc2-3Galβ1-4(Fucα1-3)Glc is not a donor-substrate. Modified 2-[4-methylumbelliferone]-α-ketoside of N-acetyl-D-neuraminic acid (4MU-NANA) and several derivatives thereof can also serve as donors for TcTs (Lee & Lee, *Anal. Biochem.* 216: 358-364 (1994)). Enzymatic synthesis of 3'-sialyl-lacto-N-biose I has been catalyzed by TcTs from lacto-N-biose I as acceptor and 2'-(4-methylumbellyferyl)-α-D-N-acelyneuraminic as donor of the N-acetylneuraminil moiety (Vetere et al., *Eur. J. Biochem.* 267: 942-949 (2000)). Further information regarding the use of trans-sialidase to synthesize β2,3-sialylated conjugates can be found in European Patent Application No. 0 557 580 A2 and U.S. Pat. No. 5,409,817, each of which is incorporated herein by reference. The intramolecular trans-sialidase from the leech *Macrobdella decora* exhibits strict specificity toward the cleavage of terminal Neu5Ac (N-acetylneuraminic acid) β2→3Gal linkage in sialoglycoconjugates and catalyzes an intramolecular trans-sialosyl reaction (Luo et al., *J. Mol. Biol.* 285: 323-332 (1999). Trans-sialidases primarily add sialic acid onto galactose acceptors, although, they will transfer sialic acid onto some other sugars. Transfer of sialic acid onto GalNAc, however, requires a sialyltransferase. Further information on the use of trans-sialidases can be found in PCT Application No. WO 93/18787; and Vetere et al., *Eur. J. Biochem.* 247: 1083-1090 (1997).

GalNAc Transferases

The invention also may utilize β1,4-GalNAc transferase polypeptides. The β1,4-GalNAc transferases, when placed in a reaction mixture, catalyze the transfer of a GalNAc residue from a donor (e.g., UTDP-GalNAc) to a suitable acceptor saccharide (typically a saccharide that has a terminal galactose residue). The resulting structure, GalNAcβ1,4-Gal-, is often found in glycosphingolipids and other sphingoids, among many other saccharide compounds.

An example of a β1,4-GalNAc transferase useful in the present invention is that produced by *Campylobacter* species, such as *C. jejuni*. A presently preferred β1,4-GalNAc transferase polypeptide is that of *C. jejuni* strain OH4384.

Exemplary GalNAc transferases of use in the present invention form the following linkages: (1) (GalNAcα1→3) [(Fucα1→2)]Galβ-; (2) GalNAcα1→Ser/Thr; (3) GalNAcβ1→4Gal; (4) GalNAcβ1→3Gal; (5) GalNAcα1→3GalNAc; (6) (GalNAcβ1→4GlcUAβ1→3)$_n$; (7) (GalNAcβ1→41dUAα1→3-)$_n$; (8)-Manβ→GalNAcβGlcNAcαAsn. See, for example, U.S. Pat. Nos. 6,268,193; and 5,691,180.

GlcNAc Transferases

The present invention optionally makes use of GlcNAc transferases. Exemplary N-Acetylglucosaminyltransferases useful in practicing the present invention are able to form the following linkages: (1) GlcNAcβ1→4GlcNAc; (2) GlcNAcβ1→Asn; (3) GlcNAcβ1→2Man; (4) GlcNAcβ1→4Man; (5) GlcNAcβ1→6Man; (6) GlcNAcβ1→3Man; (7) GlcNAcα1→3Man; (8) GlcNAcβ1→.3Gal; (9) GlcNAcβ1→4Gal; (10) GlcNAcβ1→6Gal; (11) GlcNAcα1→4Gal; (12) GlcNAcα1→4GlcNAc; (13) GlcNAcβ1→6GalNAc; (14) GlcNAcβ1→3GalNAc; (15) GlcNAcβ→4GlcUA; (16) GlcNAcβ1→4GlcUA; (17) GlcNAcα1→4IdUA. See, for example, U.S. Pat. Nos. 6,268,193; and 5,691,180.

Other Glycosyltransferases

Other glycosyltransferases can be substituted into similar transferase cycles as have been described in detail for the fucosyltransferases and sialyltransferases. In particular, the glycosyltransferase can also be, for instance, glucosyltransferases, e.g., Alg8 (Stagljov et al., *Proc. Nat. Acad. Sci. USA* 91:5977 (1994)) or Alg5 (Heesen et al. *Eur. J. Biochem.* 224:71 (1994)), N-acetylgalactosaminyltransferases such as, for example, α(1,3) N-acetylgalactosaminyltransferase, β(1,4) N-acetylgalactosaminyltransferases (Nagata et al. *J. Biol. Chem.* 267:12082-12089 (1992) and Smith et al. *J. Biol Chem.* 269:15162 (1994)) and polypeptide N-acetylgalactosaminyltransferase (Homa et al. *J. Biol Chem.* 268:12609 (1993)). Suitable N-acetylglucosaminyltransferases include GnTI (2.4.1.101, Hull et al., *BBRC* 176:608 (1991)), GnTII, and GnTIII (Ihara et al. *J. Biochem.* 113:692 (1993)), GnTV (Shoreiban et al. *J. Biol. Chem.* 268: 15381 (1993)), O-linked N-acetylglucosaminyltransferase (Bierhuizen et al. *Proc. Natl. Acad. Sci. USA* 89:9326 (1992)), N-acetylglucosamine-1-phosphate transferase (Rajput et al. *Biochem J.* 285:985 (1992), and hyaluronan synthase. Suitable mannosyltransferases include α(1,2) mannosyltransferase, α(1,3) mannosyltransferase, β(1,4) mannosyltransferase, Dol-P-Man synthase, OCh1, and Pmt1.

Multiple-enzyme Oligosacclaride Syitaliesis

As discussed above, in some embodiments, two or more enzymes are used to form a desired oligosaccharide moiety. For example, a particular oligosaccharide moiety might require addition of a galactose, a sialic acid, and a fucose in order to exhibit a desired activity. Accordingly, the invention provides methods in which two or more enzymes, e.g., glycosyltransferases, trans-sialidases, or sulfotransferases, are used to obtain high-yield synthesis of a desired oligosaccharide determinant.

In some cases, a substrate-linked oligosaccharide will include an acceptor moiety for the particular glycosyltransferase of interest upon in vivo biosynthesis of the substrate. Such substrates can be glycosylated using the methods of the invention without prior modification of the glycosylation pattern of the substrate. In other cases, however, a substrate of interest will lack a suitable acceptor moiety. In such cases, the methods of the invention can be used to alter the glycosylation pattern of the substrate so that the substrate-linked oligosaccharides then include an acceptor moiety for the glycosyltransferase-catalyzed attachment of a preselected saccharide unit of interest to form a desired oligosaccharide determinant.

In an exemplary embodiment, the multiple enzyme methodology discussed in the preceding section leads to the formation of a saccharide that include a GalNAc, glucose, galactose, fucose and a sialic acid.

Either a sialyltransferase or a trans-sialidase (for α2,3-linked sialic acid only) can be used in these methods. The trans-sialidase reaction involves incubating the protein to be modified with a reaction mixture that contains a suitable amount of a galactosyltransferase (galβ1,3 or galβ1,4), a suitable galactosyl donor (e.g., UDP-galactose), a trans-sialidase, a suitable sialic acid donor substrate, a fucosyltransferase (capable of making an α1,3 or α1,4 linkage), a suitable fucosyl donor substrate (e.g., GDP-facose), and a divalent metal ion. These reactions can be carried out either sequentially or simultaneously.

If a sialyltransferase is used, in an exemplary embodiment, the method involves incubating the protein to be modified with a reaction mixture that contains a suitable amount of a galactosyltransferase (galβ1,3 or galβ1,4), a suitable galactosyl donor (e.g., UDP-galactose), a sialyltransferase (α2,3 or α2,6) and a suitable sialic acid donor substrate (e.g., CMP sialic acid). The reaction is allowed to proceed substantially to completion, and then a fucosyltransferase (capable of making an α1,3 or α1,4 linkage) and a suitable fucosyl donor substrate (eg. GDP-fucose) are added. If a fucosyltransferase is used that requires a sialylated substrate (e.g., FucT VII), the reactions can be conducted simultaneously.

Glycosyltransferase Reaction Mixtures

The glycosyltransferases, substrates, and other reaction mixture ingredients described above are combined by admixture in an aqueous reaction medium (solution). The medium generally has a pH value of about 5 to about 9. The selection of a medium is based on the ability of the medium to maintain pH value at the desired level. Thus, in some embodiments, the medium is buffered to a pH value of about 7.5. If a buffer is not used, the pH of the medium should be maintained at about 5 to 8.5, depending upon the particular glycosyltransferase used. For fucosyltransferases, the pH range is preferably maintained from about 7.2 to 7.8. For sialyltransferases, the range is preferably from about 5.5 and about 6.5. A suitable base is NaOH, preferably 6 M NaOH.

Enzyme amounts or concentrations are expressed in activity Units, which is a measure of the initial rate of catalysis. One activity Unit catalyzes the formation of 1 μmol of product per minute at a given temperature (typically 37° C.) and pH value (typically 7.5). Thus, 10 Units of an enzyme is a catalytic amount of that enzyme where 10 μmol of substrate are converted to 10 μmol of product in one minute at a temperature of 37° C. and a pH value of 7.5.

The reaction medium may also comprise solubilizing detergents (e.g., Triton or SDS) and organic solvents, e.g., methanol or ethanol, if necessary. The enzymes can be utilized free in solution or can be bound to a support such as a polymer. The reaction mixture is thus substantially homogeneous at the beginning, although some precipitate can form during the reaction.

The temperature at which an above process is carried out can range from just above freezing to the temperature at which the most sensitive enzyme denatures. That temperature range is preferably about zero degrees C. to about 45° C., and more preferably at about 20° C. to about 37° C.

The reaction mixture so formed is maintained for a period of time sufficient to obtain the desired high yield of desired oligosaccharide determinants present on oligosaccharide groups attached to the substrate to be glycosylated. For large-scale preparations, the reaction will often be allowed to proceed for about 8-240 hours, with a time of between about 12 and 72 hours being more typical.

In embodiments in which more than one glycosyltransferase is used to obtain the compositions of substrates having substantially uniform substrates, the enzymes and reagents for a second glycosyltransferase reaction can be added to the reaction medium once the first glycosyltransferase reaction has neared completion. For some combinations of enzymes, the glycosyltransferases and corresponding substrates can be combined in a single initial reaction mixture; the enzymes in such simultaneous reactions preferably do not form a product that cannot serve as an acceptor for the other enzyme. For example, most sialyltransferases do not sialylate a fucosylated acceptor, so unless a fucosyltransferase that only works on sialylated acceptors is used (e.g., FucT VII), a simultaneous reaction by both enzymes will most likely not result in the desired high yield of the desired oligosaccharide determinant. By conducting two glycosyltransferase reactions in sequence in a single vessel, overall yields are improved over procedures in which an intermediate species is isolated. Moreover, cleanup and disposal of extra solvents and by-products is reduced.

One or more of the glycosyltransferase reactions can be carried out as part of a glycosyltransferase cycle. Preferred conditions and descriptions of glycosyltransferase cycles have been described. A number of glycosyltransferase cycles (for example, sialyltransferase cycles, galactosyltransferase cycles, and fucosyltransferase cycles) are described in U.S. Pat. Nos. 5,374,541 and WO 9425615 A. Other glycosyltransferase cycles are described in Ichikawa et al. *J. Am. Chem. Soc.* 114:9283 (1992), Wong et al. *J. Org. Chem.* 57: 4343 (1992), DeLuca, et al., *J. Am. Chem. Soc.* 117:5869-5870 (1995), and Ichikawa et al. *In Carbohydrates and Carbohydrate Polymers.* Yaltami, ed. (ATL Press, 1993).

For the above glycosyltransferase cycles, the concentrations or amounts of the various reactants used in the processes depend upon numerous factors including reaction conditions such as temperature and pH value, and the choice and amount of acceptor saccharides to be glycosylated. Because the glycosylation process permits regeneration of activating nucleotides, activated donor sugars and scavenging of produced PPi in the presence of catalytic amounts of the enzymes, the process is limited by the concentrations or amounts of the stoichiometric substrates discussed before. The upper limit for the concentrations of reactants that can be used in accordance with the method of the present invention is determined by the solubility of such reactants.

Preferably, the concentrations of activating nucleotides, phosphate donor, the donor sugar and enzymes are selected such that glycosylation proceeds until the acceptor is consumed. The considerations discussed below, while in the context of a sialyltransferase, are generally applicable to other glycosyltransferase cycles.

Each of the enzymes is present in a catalytic amount. The catalytic amount of a particular enzyme varies according to the concentration of that enzyme's substrate as well as to reaction conditions such as temperature, time and pH value. Means for determining the catalytic amount for a given enzyme under preselected substrate concentrations and reaction conditions are well known to those of skill in the art.

In another exemplary embodiment the reaction mixture contains at least one glycosyl transferase, a donor substrate, an acceptor sugar and a divalent metal cation. The concentration of the divalent metal cation in the reaction medium is maintained between about 2 mm and about 75 mm, preferably between about 5 mm and about 50 mm and more preferably between about 5 and about 30 mm.

By periodically monitoring the metal ion concentration in the reaction medium and supplementing the medium by additional amounts of divalent metal ions, the reaction cycles can be driven to completion within a suitable timeframe. Additionally, if more than one glycosyltransferase is used, consecutive cycles can be carried out in the same reaction vessel without isolation of the intermediate product. Moreover, by removing the inhibitory pyrophosphate, the reaction cycles can be run at substantially higher substrate (acceptor) concentration. Preferred divalent metal ions for use in the present invention include $Mn^{++}$, $Mg^{++}$, $Co^{++}$, $Ca^{++}$, $Zn^{++}$ and combinations thereof. More preferably, the divalent metal ion is $Mn^{++}$.

In other embodiments, the saccharyl moiety is prepared using an activated sugar. Activated sugars, which are useful in the present invention are typically glycosides which have been synthetically altered to include an activated leaving group. As used herein, the term "activated leaving group" refers to those moieties, which are easily displaced in enzyme-regulated nucleophilic substitution reactions. Many activated sugars are known in the art. See, for example, Vocadlo et al., In CARBOHYDRATE CHEMISTRY AND BIOLOGY, Vol. 2, Ernst et al. *Ed., Wiley-VCH Verlag: Weinheim, Germany*, 2000; Kodama et al., *Tetrahedron Lett.* 34: 6419 (1993); Lougheed, et al., *J. Biol. Chem.* 274: 37717 (1999)).

Examples of activating groups include fluoro, chloro, bromo, tosylate ester, mesylate ester, triflate ester and the like. Preferred activated leaving groups, for use in the present invention, are those that do not significantly sterically encumber the enzymatic transfer of the glycoside to the acceptor. Accordingly, preferred embodiments of activated glycoside derivatives include glycosyl fluorides and glycosyl mesylates, with glycosyl fluorides being particularly preferred. Among the glycosyl fluorides, α-galactosyl fluoride, α-mannosyl fluoride, α-glucosyl fluoride, α-fucosyl fluoride, α-xylosyl fluoride, α-sialyl fluoride, α-N-acetylglucosaminyl fluoride, α-N-acetylgalactosaminyl fluoride, β-galactosyl fluoride, β-mannosyl fluoride, β-glucosyl fluoride, β-fucosyl fluoride, β-xylosyl fluoride, β-sialyl fluoride, β-N-acetylglucosaminyl fluoride and β-N-acetylgalactosaminyl fluoride are most preferred.

By way of illustration, glycosyl fluorides can be prepared from the free sugar by first acetylating the sugar and then treating it with HF/pyridine. This generates the thermodynamically most stable anomer of the protected (acetylated) glycosyl fluoride (i.e., the α-glycosyl fluoride). If the less stable anomer (i.e., the β-glycosyl fluoride) is desired, it can be prepared by converting the peracetylated sugar with HBr/HOAc or with HCl to generate the anomeric bromide or chloride. This intermediate is reacted with a fluoride salt such as silver fluoride to generate the glycosyl fluoride. Acetylated glycosyl fluorides may be deprotected by reaction with mild (catalytic) base in methanol (e.g. NaOMe/MeOH). In addition, many glycosyl fluorides are commercially available.

Other activated glycosyl derivatives can be prepared using conventional methods known to those of skill in the art. For example, glycosyl mesylates can be prepared by treatment of the fully benzylated hemiacetal form of the sugar with mesyl chloride, followed by catalytic hydrogenation to remove the benzyl groups.

In a preferred embodiment, the method results in glycosylation, e.g., sialylation of greater than about 80% of the appropriate glycosyl acceptor moieties on the saccharide. Generally, the time required to obtain greater than about 80% glycosylation is less than or equal to about 48 hours.

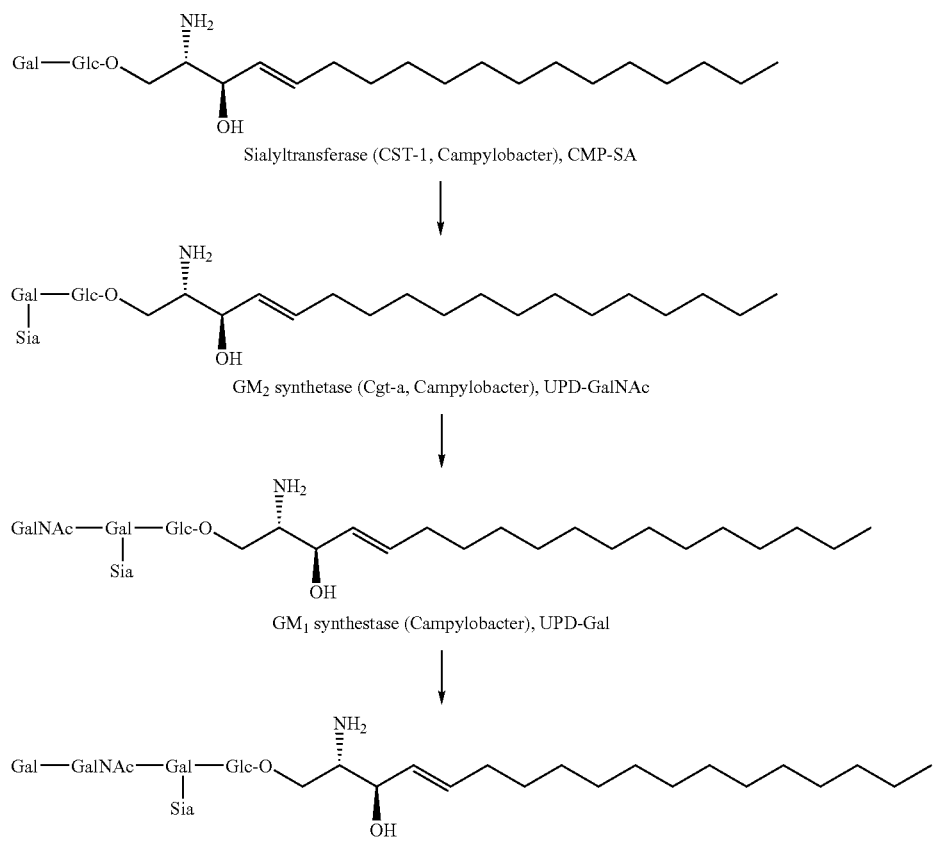

Scheme 1

In Scheme 1, the ceramide scaffold, prepared either chemically or enzymatically, is contacted with a sialyltransferase and a sialic acid donor. The resulting sialylated adduct is contacted with GM2 synthetase and a GalNAc donor. The resulting product is contacted with GM1 synthetase to afford the desired glycosyl sphingosine.

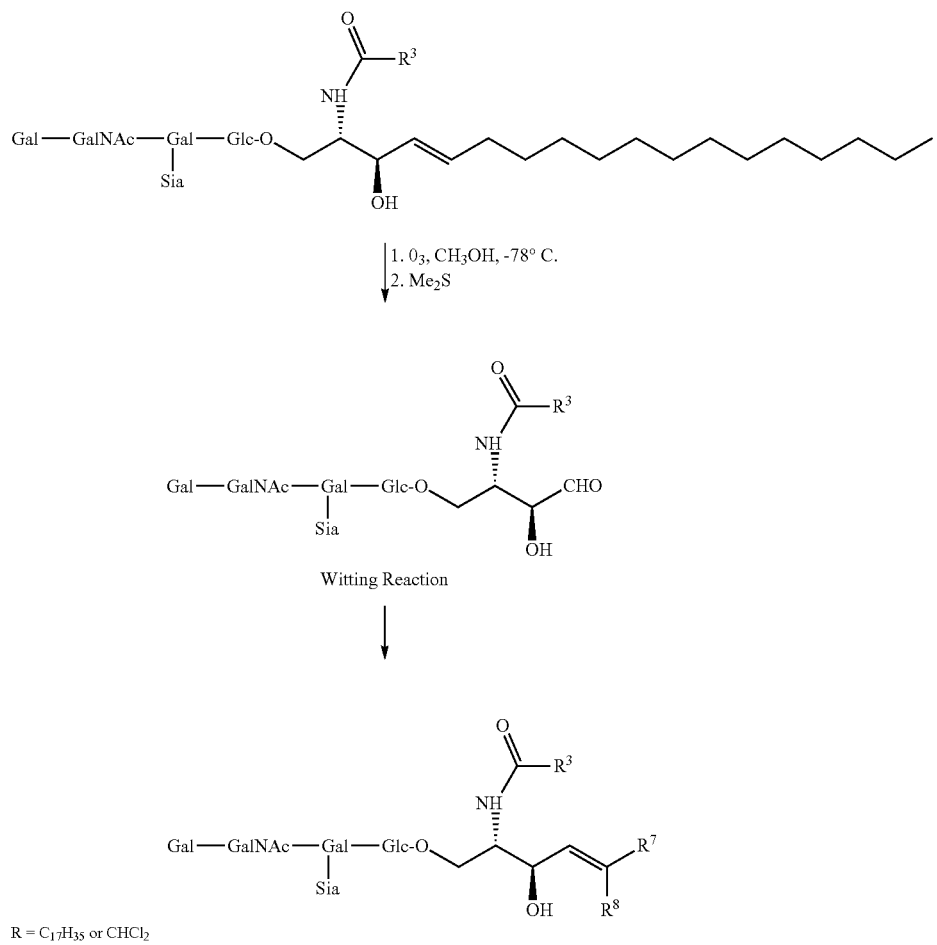

In Scheme 2, a ceramide is ozonized, cleaving the alkyl chain of the sphingosine at the point of unsaturation, resulting in the formation of an aldehyde. The aldehyde is a substrate for a Wittig reaction that converts the aldehyde into the desired alkene.

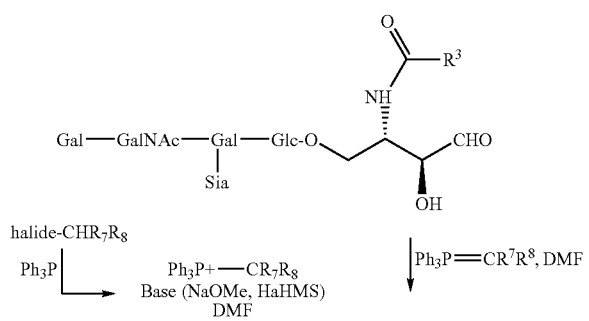

-continued

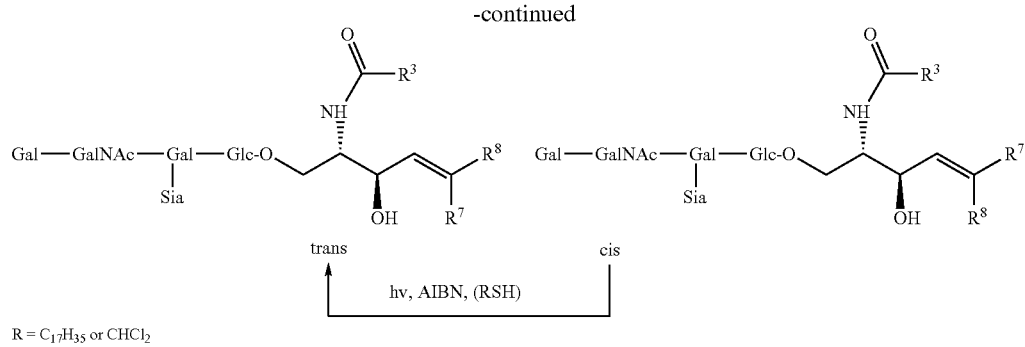

R = C$_{17}$H$_{35}$ or CHCl$_2$

Scheme 3 provides another example of the formation of a compound of the invention under Wittig conditions. The configuration of the alkene portion of the glycosphingolipid can be converted between cis and trans isomers by treating the cis isomer with AIBN and irradiating the mixture.

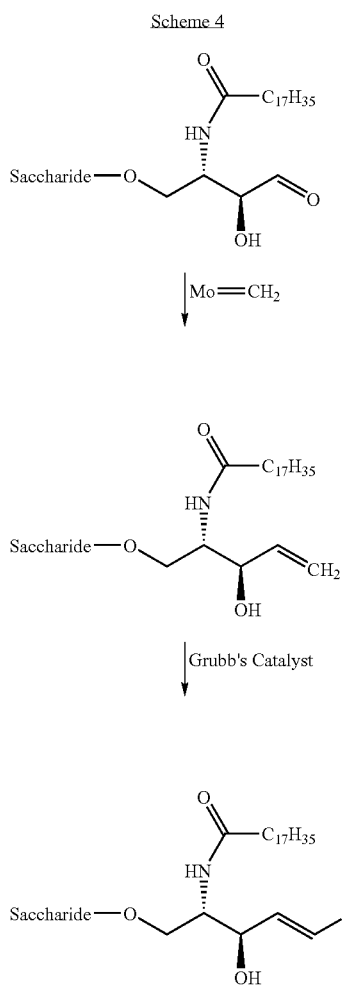

Scheme 4 sets forth a method for preparing a glycosphingolipid. A glycosylated ceramide aldehyde is converted to the corresponding methylene derivative by the action of Mo=CH2. The resulting methylene adduct is contacted with Grubb's catalyst and an alkene. The resulting olefin metathesis reaction produces the desired glycosphingolipid.

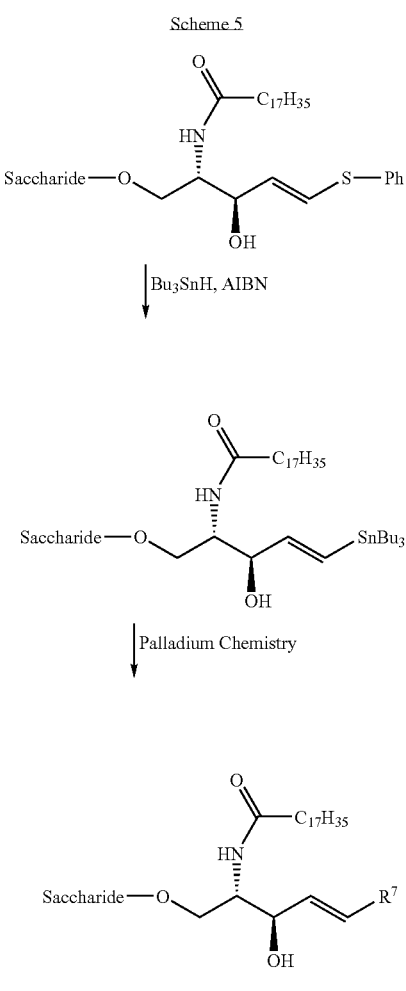

Scheme 5 provides another exemplary route to a glycosphingolipid of the invention. A glycosylated thiophenyl ceramide is converted to a stannane derivative by reaction with Bu$_3$SnH and AIBN. Palladium coupling chemistry is used to couple alkyl group, R$^7$, to the glycosylated ceramide backbone.

Scheme 6

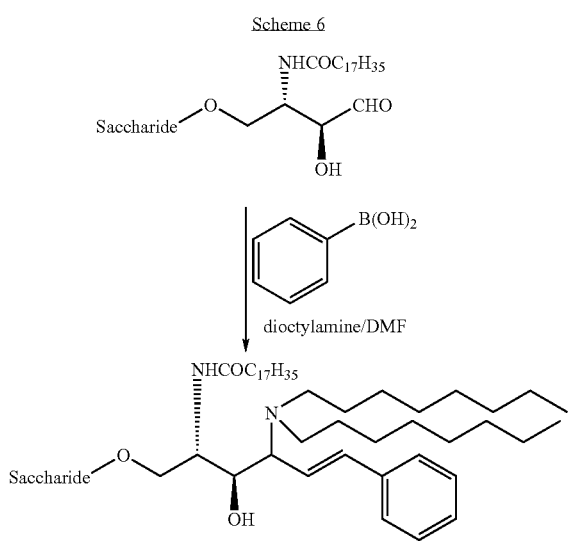

In Scheme 6, the aldehyde is converted to the corresponding benzylic alkene derivative by the action of a phenyl boronic acid. The secondary hydroxyl moiety of the base is converted to a dioctylamino moiety.

Scheme 7

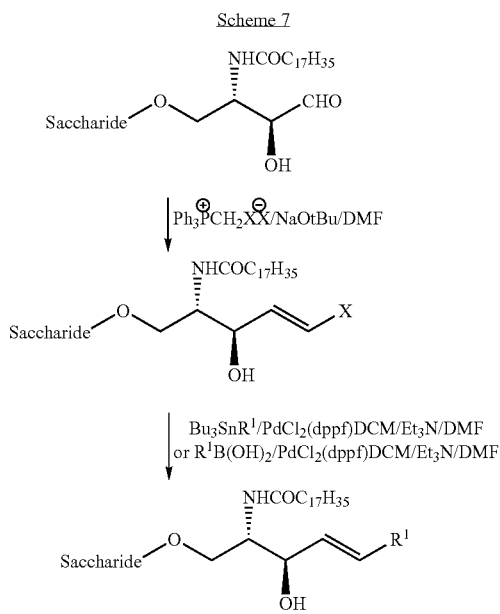

According to Scheme 7, the aldehyde is converted to corresponding vinylic halide. The halide is displaced via an appropriate stannous compound or boronic acid to provide the desired compound.

If the acceptor is a ceramide, the enzymatic step is optionally preceded by hydrolysis of the fatty acid moiety from the ceramide. Methods of removing a fatty acid moiety from a glycosphingolipid are known to those of skill in the art. Standard carbohydrate and glycosphingolipid chemistry methodology can be employed, such as that described in, for example, Paulson et al. (1985) *Carbohydrate Res.* 137: 39-62; Beith-Halahmi et al. (1967) *Carbohydrate Res.* 5: 25-30; Alais and Veyrieries (1990) *Carbohydrate Res.* 207: 11-31; Grudler and Schmidt (1985) *Carbohydrate Res.* 135: 203-218; Ponpipom et al. (1978) *Tetrahedron Lett.* 1717-1720; Murase et al. (1989) *Carbohydrate Res.* 188: 71-80; Kameyama et al. (1989) *Carbohydrate Res.* 193: c1-c5; Hasegawa et al. (1991) *J. Carbohydrate Chem.* 10: 439-459; Schwarzmann and Sandhoff (1987) *Meth. Enzymol.* 138: 319-341; Guadino and Paulson (1994) *J. Am. Chem. Soc.* 116: 1149-1150 (including supplemental material, which is also incorporated herein by reference). For example, the fatty acid moiety can be removed by base hydrolysis. Once the glycosylation reactions are completed, the same or a different fatty acid can be attached to the product of the glycosylation reactions. Methods for coupling a fatty acid are generally known in the art and examples are discussed herein, supra.

Purification

The products produced by the above processes can be used without purification. However, for some applications it is desirable to purify the compounds. Standard, well-known techniques for purification of substrates are generally suitable. For example, thin or thick layer chromatography, column chromatography, ion exchange chromatography, or membrane filtration can be used. Moreover, membrane filtration, preferably utilizing a reverse osmotic membrane, or one or more column chromatographic techniques, can be utilized. For instance, membrane filtration wherein the membranes have molecular weight cutoff of about 3000 to about 10,000 can be used to remove proteins such as glycosyl transferases. Nanofiltration or reverse osmosis can then be used to remove salts and/or purify the product saccharides (see, e.g., WO 98/15581). Nanofilter membranes are a class of reverse osmosis membranes that pass monovalent salts but retain polyvalent salts and uncharged solutes larger than about 100 to about 2,000 Daltons, depending upon the membrane used. Thus, in a typical application, saccharides prepared by the methods of the present invention will be retained in the membrane and contaminating salts will pass through.

Another exemplary purification strategy makes use of a membrane in conjunction with an organic solvent. Both glycolipids and glycosphingolipids can be purified by this method. Moreover, any of the intermediate enzyme reaction products described herein can be purified according to this method. The method includes concentrating a reaction product in a membrane purification system with the addition of an organic solvent. Suitable solvents include, but are not limited to alcohols (e.g., methanol), halocarbons (e.g., chloroform), and mixtures of hydrocarbons and alcohols (e.g., xylenes/methanol). In a preferred embodiment, the solvent is methanol. The concentration step can concentrate the reaction product to any selected degree. Generally, the degree of concentration is from about 1- to about 100-fold, including from about 5- to about 50-fold, also including from about 10-to about 20-fold. The membrane purification system is selected from a variety of such systems known to those of skill in the art. For example, one useful membrane purification system is a 10K hollow fiber. In an exemplary embodiment, the method comprises concentrating the reaction mixture about ten-fold using a 10K hollow fiber membrane purification system, adding water and diafiltering the solution to about one-tenth the original volume, adding methanol to the retentate, and diafiltering to allow the reaction product to pass in the permeate. Concentration of the permeate solution yields the reaction product.

Detectable Labels

In an exemplary embodiment, the compound of the invention includes a detectable label, such as a fluorophores or radioactive isotope. For example, the detectable label can be appended to a glycosyl moiety (e.g., sialic acid) by means of a linker arm in a manner that still allows the labeled glycosyl moiety serves as a substrate for an appropriate glycosyltransferase as discussed herein.

The embodiment of the invention in which a label is utilized is exemplified by the use of a fluorescent label. Fluorescent labels have the advantage of requiring few precautions in their handling, and being amenable to high-throughput visualization techniques (optical analysis including digitization of the image for analysis in an integrated system comprising a computer). Preferred labels are typically characterized by high sensitivity, high stability, low background, long lifetimes, low environmental sensitivity and high specificity in labeling.

Many fluorescent labels can be incorporated into the compositions of the invention. Many such labels are commercially available from, for example, the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie A G, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

Pharmaceutical Formulations

In yet another embodiment, the invention provides a pharmaceutical formulation that includes a compound produced by a method according to the invention in admixture with a pharmaceutically acceptable carrier.

The substrates having desired oligosaccharide determinants described above can then be used in a variety of applications, e.g., as antigens, diagnostic reagents, or as therapeutics. Thus, the present invention also provides pharmaceutical compositions, which can be used in treating a variety of conditions. The pharmaceutical compositions are comprised of substrates made according to the methods described above.

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985). For a brief review of methods for drug delivery, see, Langer, *Science* 249: 1527-1533 (1990).

The pharmaceutical compositions are intended for parenteral, intranasal, topical, oral or local administration, such as by aerosol or transdermally, for prophylactic and/or therapeutic treatment. Commonly, the pharmaceutical compositions are administered parenterally, e.g., intravenously. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils, intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. The compositions may contain pharmaceutically acceptable auxiliary substances as required to approximate physiological conditions, such as pH adjusting and buffering agents, tonicity adjusting agents, wetting agents, detergents and the like.

The composition may also contain a glycolipid prepared by a method of the invention that is conjugated to an immunogenic species, e.g., KLH. Moreover, the compositions prepared by methods of the invention and their immunogenic conjugates may be combined with an adjuvant.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9 and most preferably from 7 and 8.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective dose." Amounts effective for this use will depend on the severity of the disease and the weight and general state of the patient, but generally range from about 0.5 mg to about 2,000 mg of substrate per day for a 70 kg patient, with dosages of from about 5 mg to about 200 mg of the compounds per day being more commonly used.

In prophylactic applications, compositions containing the substrates of the invention are administered to a patient susceptible to or otherwise at risk of a particular disease. Such an amount is defined to be a "prophylactically effective dose." In this use, the precise amounts again depend on the patient's state of health and weight, but generally range from about 0.5 mg to about 2,000 mg per 70 kilogram patient, more commonly from about 5 mg to about 200 mg per 70 kg of body weight.

Single or multiple administrations of the compositions can be carried out with dose levels and pattern being selected by the treating physician. In any event, the pharmaceutical formulations should provide a quantity of the substrates of this invention sufficient to effectively treat the patient.

The substrates can also find use as diagnostic reagents. For example, labeled substrates can be used to determine the locations at which the substrate becomes concentrated in the body due to interactions between the desired oligosaccharide determinant and the corresponding ligand. For this use, the compounds can be labeled with appropriate radioisotopes, for example, $^{125}$I, $^{14}$C, or tritium, or with other labels known to those of skill in the art.

The dosage ranges for the administration of the glycosphingolipids of the invention are those large enough to produce the desired effect in which the symptoms of the immune response show some degree of suppression. The dosage should not be so large as to cause adverse side effects. Generally, the dosage will vary with the age, condition, sex and extent of the disease in the animal and can be determined by one of skill in the art. The dosage can be adjusted by the individual physician in the event of any counterindications.

Additional pharmaceutical methods may be employed to control the duration of action. Controlled release preparations may be achieved by the use of polymers to conjugate, complex or adsorb the glycosphingolipid. The controlled delivery may be exercised by selecting appropriate macromolecules (for example, polyesters, polyamino carboxymethylcellulose, and protamine sulfate) and the concentration of macromolecules as well as the methods of incorporation in order to control release. Another possible method to control the duration of action by controlled release preparations is to incorporate the glycosphingolipid into particles of a polymeric material such as polyesters, polyamino acids, hydrogels, poly (lactic acid) or ethylene vinylacetate copolymers.

In order to protect the glycosphingolipids from binding with plasma proteins, it is preferred that the glycosphingolipids be entrapped in microcapsules prepared, for example, by coacervation techniques or by interfacial polymerization, for example, hydroxymethylcellulose or gelatin-microcapsules and poly (methymethacrylate) microcapsules, respectively, or in colloidal drug delivery systems, for example, liposomes, albumin microspheres, microemulsions, nanoparticles, and nanocapsules or in macroemulsions. Such teachings are disclosed in Remington's Pharmaceutical Sciences (16th Ed., A. Oslo, ed., Mack, Easton, Pa., 1980).

The glycosphingolipids of the invention are well suited for use in targetable drug delivery systems such as synthetic or natural polymers in the form of macromolecular complexes, nanocapsules, microspheres, or beads, and lipid-based systems including oil-in-water emulsions, micelles, mixed micelles, liposomes, and resealed erythrocytes. These systems are known collectively as colloidal drug delivery systems. Typically, such colloidal particles containing the dispersed glycosphingolipids are about 50 mn-2 µm in diameter. The size of the colloidal particles allows them to be administered intravenously such as by injection, or as an aerosol. Materials used in the preparation of colloidal systems are typically sterilizable via filter sterilization, nontoxic, and biodegradable, for example albumin, ethylcellulose, casein, gelatin, lecithin, phospholipids, and soybean oil. Polymeric colloidal systems are prepared by a process similar to the coacervation of microencapsulation.

In an exemplary embodiment, the glycosphingolipids are components of a liposome, used as a targeted delivery system. When phospholipids are gently dispersed in aqueous media, they swell, hydrate, and spontaneously form multilamellar concentric bilayer vesicles with layers of aqueous media separating the lipid bilayer. Such systems are usually referred to as multilamellar liposomes or multilamellar vesicles (MLVs) and have diameters ranging from about 100 nm to about 4 µm. When MLVs are sonicated, small unilamellar vesicles (SUVS) with diameters in the range of from about 20 to about 50 nm are formed, which contain an aqueous solution in the core of the SUV.

Examples of lipids useful in liposome production include phosphatidyl compounds, such as phosphatidylglycerol, phosphatidylcholine, phosphatidylserine, and phosphatidylethanolamine. Particularly useful are diacylphosphatidylglycerols, where the lipid moiety contains from 14-18 carbon atoms, particularly from 16-18 carbon atoms, and are saturated. Illustrative phospholipids include egg phosphatidylcholine, dipalmitoylphosphatidylcholine, and distearoylphosphatidylcholine.

In preparing liposomes containing the glycosphingolipids of the invention, such variables as the efficiency of glycosphingolipid encapsulation, lability of the glycosphingolipid, homogeneity and size of the resulting population of liposomes, glycosphingolipid-to-lipid ratio, permeability instability of the preparation, and pharmaceutical acceptability of the formulation should be considered. Szoka, et al, *Annual Review of Biophysics and Bioengineerinzg,* 9: 467 (1980); Deamer, et al., in LIPOSOMES, Marcel Dekker, New York, 1983, 27: Hope, et al., *Chem. Phys. Lipids,* 40: 89 (1986)).

The targeted delivery system containing the glycosphingolipids of the invention may be administered in a variety of ways to a host, particularly a mammalian host, such as intravenously, intramuscularly, subcutaneously, intra-peritoneally, intravascularly, topically, intracavitarily, transdermally, intranasally, and by inhalation. The concentration of the glycosphingolipids will vary upon the particular application, the nature of the disease, the frequency of administration, or the like. The targeted delivery system-encapsulated glycosphingolipid may be provided in a formulation comprising other compounds as appropriate and an aqueous physiologically acceptable medium, for example, saline, phosphate buffered saline, or the like.

The compounds produced by a method of the invention can also be used as an immunogen for the production of monoclonal or polyclonal antibodies specifically reactive with the compounds of the invention. The multitude of techniques available to those skilled in the art for production and manipulation of various immunoglobulin molecules can be used in the present invention. Antibodies may be produced by a variety of means well known to those of skill in the art.

The production of non-human monoclonal antibodies, e.g., murine, lagomorpha, equine, etc., is well known and may be accomplished by, for example, immunizing the animal with a preparation containing the substrates of the invention. Antibody-producing cells obtained from the immunized animals are immortalized and screened, or screened first for the production of the desired antibody and then immortalized. For a discussion of general procedures of monoclonal antibody production see Harlow and Lane, *Antibodies, A Laboratory Manual* Cold Spring Harbor Publications, N.Y. (1988).

Subjects (animals or humans), preferably mammalian, in need of treatment may be administered a therapeutically effective amount, i.e., a dosage that will provide optimal efficacy, of a compound of the invention, alone or as part of pharmaceutical composition. As would be recognized by those of skill in the art, a "therapeutically effective amount" and mode of administration will vary from subject to subject and thus will be determined on a case by case basis. Factors to be considered include, but are not limited to, the subject (e.g. mammal) being treated, its sex, weight, diet, concurrent medication, overall clinical condition, the particular compounds employed, and the specific use for which these compounds are employed. Therapeutically effective amounts or dosages may be determined by either in vitro or in vivo methods. In general, a "therapeutically effective amount" of a compound or composition is an amount that will result in the prophylaxis, treatment or cure of neuronal cell disorders. For example, a therapeutically effective amount of a compound or composition of the invention in the prophylaxis, treatment or cure of Parkinson's disease will be that amount that results in slower progression of the disease and/or development of motor skills. A therapeutically effective amount of a compound or composition of the invention in the prophylaxis, treatment or cure of Alzheimer's disease will be that amount that results in, for example, improvement of the subject's memory. A therapeutically effective amount of a compound or composition of the invention in the prophylaxis, treatment or cure of the lasting effects of eschemia/stroke will be that amount that results in, for example, reduction of loss of neurological function (e.g., speech, motor, etc.) and/or improvement of sympathetic or parasympathetic pathways.

Modes of administration include those known in the art including, but not limited to, oral, injection, intravenous (bolus and/or infusion), subcutaneous, intramuscular, colonic, rectal, nasal and intraperitoneal administration. Preferably, compounds of the invention, alone or as part of a pharmaceutical composition are taken orally.

For injection by hypodermic needle, it may be assumed the dosage is delivered into the body's fluids. For other routes of administration, the absorption efficiency may be individually determined for each compound of the invention by methods well known in pharmacology. Accordingly, as would be understood by one of skill in the art, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, a compound of the invention is administered at lower dosage levels, with dosage levels being increased until the desired effect is achieved.

A typical dosage might range from about 0.1 mg/kg to about 1000 mg/kg, preferably from 0.1 mg/kg to about 100 mg/kg, more preferably from about 0.1 mg/kg to about 30 mg/kg, more preferably from about 0.1 mg/kg to about 10 mg/kg, and more preferably 0.1 mg/kg to about 3 mg/kg. Advantageously, the compounds of the invention, alone or as part of a pharmaceutical composition, may be administered several times daily, and other dosage regimens may also be useful. A compound of the invention may be administered on a regimen in a single or multidose (e.g. 2 to 4 divided daily doses) and/or continuous infusion.

A compound of the invention, alone or as part of a pharmaceutical composition, for administration may be sterilized prior to administration. Sterility may be readily accomplished by filtration through sterile membranes such as 0.2 micron membranes, or by other conventional methods. A compound of the invention, alone or as part of a pharmaceutical composition, typically may be stored in lyophilized form or as an aqueous solution. pH may be a factor for certain modes of administration. In such instances, the pH typically will range between about 2-10, preferably, between about 5-8, more preferably 6.5-7.5, i.e., physiological pH.

The Methods

Treatment and Neuroprotection

In another embodiment, the invention provides a method for the prevention or treatment of a disorder of the nervous system in an animal or human comprising the step of administering to an animal or human in need thereof a therapeutically effective amount of the compound of the invention. The compounds of the invention are of use to treat any number of nervous system disorders. Exemplary disorders of the nervous system is selected from the group consisting of Parkinson's disease, ischemia, stroke, Alzheimer's disease, depression, anxiety, encephalitis, meningitis, amyotrophic lateral sclerosis, trauma, spinal cord injury, nerve injury, and nerve regeneration. In another exemplary embodiment, the disorder is a proliferative disorder such as a glioma.

The compounds of the present invention are neuroprotective (e.g., protects neurons and glia). The term "neuroprotection" relates to any prophylaxis (pre-onset), treatment (on-set) and/or cure (post-onset) of indications resulting from the impairment or destruction of neuronal cells. Such indications include Parkinson's disease, ischemia, hypoxia, stroke, epilepsy, metabolic dysfunction, aging, toxic diseases, Alzheimer's, central nervous system disorders (e.g., spinal cord injury), multiple sclerosis, Huntington's disease, CABG, depression, anxiety, encephalitis, meningitis, amyotrophic lateral sclerosis, trauma, spinal cord injury, nerve injury, neuropathy and nerve regeneration.

The compounds of the invention are also neurogenic (e.g., promotes differentiation of neurons and proliferation or differentiation of stem cells and progenitor cells) and/or neuritogenic (e.g., promotes neurite outgrowth and synaptogenesis) and are therefore expected to be useful to treat a wide variety of neurological diseases and conditions. For example, neuritogenic compounds can advantageously be used, for example, in therapies aimed at nervous function recovery, such as in peripheral neuropathies and pathologies associated with neuronal damage (e.g., stroke, ischemic injuries, transverse myelitis, trauma, spinal cord injuries and neuropathies associated with diabetes).

The compounds of the present invention also inhibit proliferation of a number of different cell types of the immune system (e.g., $CD_4^+$ T cells, lymphocytes and NK cells) and to inhibit the production of certain cytokines. Thus, selected compounds are immunosuppressive and therefore useful for the treatment and/or prevention of systemic or organ-specific autoimmune diseases, such as multiple sclerosis, rheumatoid arthritis, sarcoid, paraneoplastic disease, Sjogren, psoriasis, scleroderma, vasculitides, chronic polyarthritis, lupus erythematosus, juvenile-onset diabetes mellitus, and also to prevent organ transplant rejection as well as rejection by the transplanted material against the host, as in the case of bone marrow or stem cell transplant.

A compound of the invention is also useful in the treatment of cancers in general, including liver, lung, colon, prostate, breast, pancreatic, and cancers of the brain, such as glioma and neuroblastoma. Further, a compound of the present invention is useful as an immunosuppressive and immunostimulatory agent, and has applications in organ transplantation, autoimmune disease, arthritis, Systemic Lupus Erythematosus, irritable bowel disease, radiation toxicity and inflammation, psoriasis, dermatitis, multiple sclerosis, trauma and sepsis.

A compound of the invention can be used to stimulate or suppress T-cells and B-cells, and can be used for antibody suppression or stimulation. Methods of stimulating and suppressing T-cells and B-cells are well known in the art. Further, a compound of the invention may be used in a method to inhibit or activate membrane receptors, including G-protein coupled receptors, cell surface membrane receptor systems, and nuclear membrane receptors. A compound of the invention can further be used to treat type II diabetes and as an ethryopoeitin replacement.

A compound of the present invention is also useful as an inhibitor of platelet aggregation. Further, a compound of the present invention is useful in AIDS treatment, by inhibiting viral adhesion through G-protein coupled receptors, including CCRC5 and CXC4. A compound of the invention is also useful in the treatment of diseases such as Chagas disease, as well as diseases, disorders, and conditions described in U.S. Pat. Nos. 4,476,119, 4,593,091, 4,639,437, 4,707,469, 4,713,374, 4,716,223, 4,849,413, 4,940,694, 5,045,532, 5,135,921, 5,183,807, 5,190,925, 5,210,185, 5,218,094, 5,229,373, 5,260,464, 5,264,424, 5,350,841, 5,424,294, 5,484,775, 5,519,007, 5,521,164, 5,523,294, 5,677,285, 5,792,858, 5,795,869, and 5,849,717, each of which is incorporated by reference herein.

One possible mechanism of action of a compound of the invention is to stimulate nerve growth factors. Another possible mechanism of action of a compound of the invention is to inhibit growth of cancer cells, and in particular, neuroblastoma cells. For example, it has been shown that administration of ganglioside GM3 to murine neuroblastoma cells can inhibit the growth of the neuroblastoma cells (Zhang et al., 1995, Anticancer Res. 15:661-6). Glycosphingolipid and glycosphingolipid-like compounds of the present invention can be used in a similar inhibitory capacity.

The compounds and pharmaceutical compositions of the invention may be utilized in vivo, ordinarily in mammals such as primates, such as humans, sheep, horses, cattle, pigs, dogs, cats, rats and mice, or in vitro. The effectiveness of the compounds of the invention as neuroprotective agents may be determined using screening protocols known in the art. For example, the biological properties, as described above, of the compounds of the invention can be readily characterized by methods that are well known in the art including, for example, in vitro screening protocols (e.g. cell culture QPTP (rat ventral mesophenthalic cells), NMDA (mouse primary cortical neurons), ceramide (neuroblastoma-human)), CACO-2 (oral absorption), RBC lysis) and in vivo studies (e.g. mouse and primate MPTP toxicity studies (IP, IV, and/or oral) for effectiveness in the treatment of Parkinson's, rat Stoke studies for effectiveness for treatment of neural damage due to stroke or CABG, and dog studies for treatment of CABG) to evaluate neuroprotective efficacy.

In the cell based assays, as described herein, the compounds of the invention exhibited 50-100% greater neuroprotective activity at markedly lower concentrations than those at which gangliosides, such as GM1 are effective, the lower concentrations ranging between about 0.1 to about 1 µM.

The invention is further described with reference to the following Examples. The Examples are provided for the purpose of illustration only and the invention not be construed as being limited to these Examples, but rather should be construed to encompass any and all variations which become evident as a result of the teaching provided herein.

EXAMPLES

Example 1

General Procedure for Preparing the GM$_1$ Aldehyde

GM$_1$(2.5 g, 1.62 mmol) was dissolved in 2500 mL of methanol. This solution was cooled to −70° C. and ozone bubbled through the solution until the light blue color did not disappear (about 30 mins). The ozone was removed by bubbling nitrogen through the reaction mixture until the solution became colorless. Then, 80 mL of dimethylsulfide was added and the resulting mixture was stirred at room temperature for 2 h. The solvent was evaporated with nitrogen to dryness. The residue was co-evaporated with toluene (50 mL) and the residue dried on a high vacuum pump for 1 h to yield a white solid containing the aldehyde.

Example 2

Wittig Reaction Preparation of:

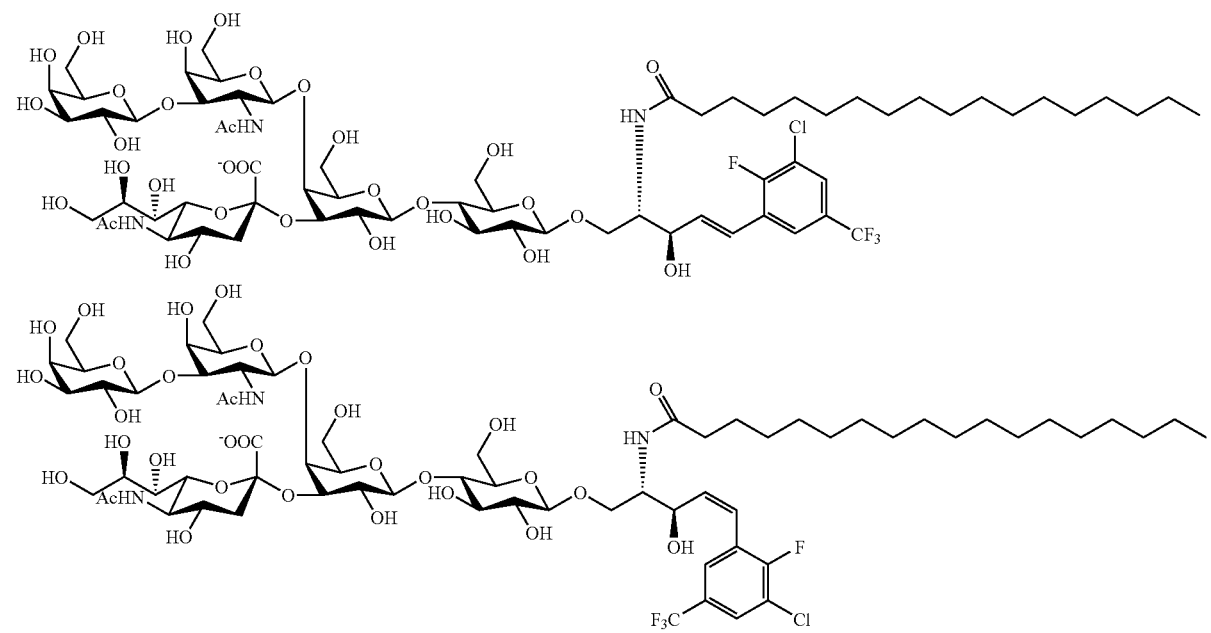

A suspension containing 3-chloro-2-fluoro-5-(trifluoromethyl)benzyl-triphenylphosphonium bromide (2.58 g, 4.66 mmol), dimethylformamide (DMF) (50 mL) was cooled to −40° C. and 1M potassium tert-butyloxide in tert-butylalcohol solution (4.49 mL) was then added. After 10 minutes, this reaction mixture was added slowly to a solution of aldehyde dissolved in DMF (200 mL) and cooled to −40° C. After addition was complete, the reaction mixture was stirred at room temperature for 1 h. The reaction mixture was then concentrated on a rotovap and the residue chromatographed (silica, CHCl$_3$/MeOH 3:1 then, MeOH/H$_2$O/NH$_4$OH 60:40:7:1) to afford 1.5 g (60% yield) of the desired product as a ~70/30 cis/trans mixture. ESI-MS; calcd for C$_{67}$H$_{106}$ClF$_4$N$_3$O$_{31}$, 1559; found 1558 [M−1]$^-$. $^1$H-NMR (500 MHz, 95% DMSO-d$_6$+5% D$_2$O) δ7.98 (d, J 6.0 Hz, 2H), 7.84 (d, J 6.0 Hz, 1H), 7.82 (d, J 5.5 Hz, 2H), 7.60 (d, J 5.5 Hz, 1H), 7.34 (d, J 9.5 Hz, 2H), 6.64 (d, J 16 Hz, 1H), 6.48 (d, J 11.5 Hz, 2H), 5.93 (dd, J 11.5/11.5 Hz, 2H), 4.79 (d, J 8.5 Hz, 2H), 4.27 (d, J 8.0 Hz, 2H), 4.21 (d, J 8.5 Hz, 2H), 3.00-4.00 (m), 1.98 (m, 2H), 1.86 (s, 3H, COCH$_3$), 1.78 (s, 3H, COCH$_3$), 1.25 (m), 0.83 (t, 3H, CH$_3$).

Example 3

Wittig Reaction Preparation of:

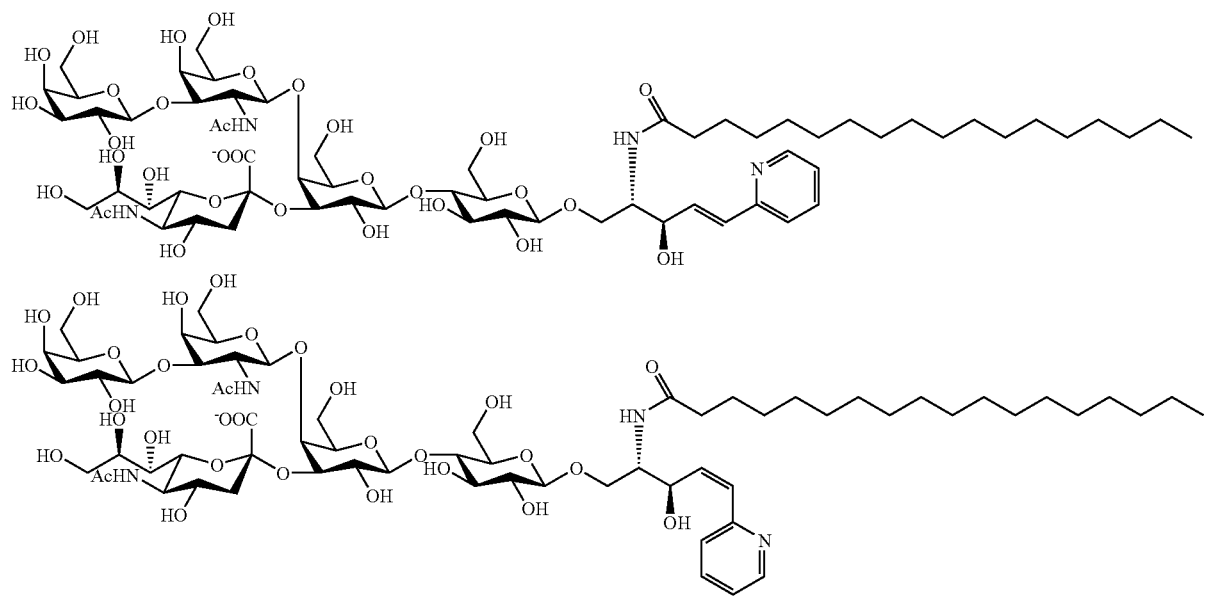

The Wittig procedure of Example 2 was followed except that the starting ylide was changed. The desired product was obtained as a white solid, (43% yield). ESI-MS; calcd for $C_{65}H_{105}N_4O_{31}$, 1440; found 1439 [M−1]⁻. ¹H-NMR (500 MHz, 95% DMSO-d₆+5% D₂O) δ 8.46 (d, J 4 Hz, 1H), 7.70 (dd, J 6.5 and 9.6 Hz, 1H), 7.37 (d, J 8.0 Hz, 1H), 7.18 (dd, J 5.0 and 5.0 Hz, 1H), 6.64 (dd, J 15.5 and 6.0 Hz, 1H), 6.57 (d, J 15.5 Hz, 1H), 4.82 (d, J 8.5 Hz, 1H), 4.27 (d, J 8.0 Hz, 1H), 4.18-4.22 (2d, 2H), 3.10-3.93 (m), 2.02 (t, 2H), 1.86 (s, 3H, COCH₃), 1.75 (s, 3H, COCH₃), 1.36 (m, 2H), 1.22 (s), 1.06 (m, 2H, CH₂), 0.83 (t, 3H, CH₃).

Example 4

Wittig Reaction Preparation of:

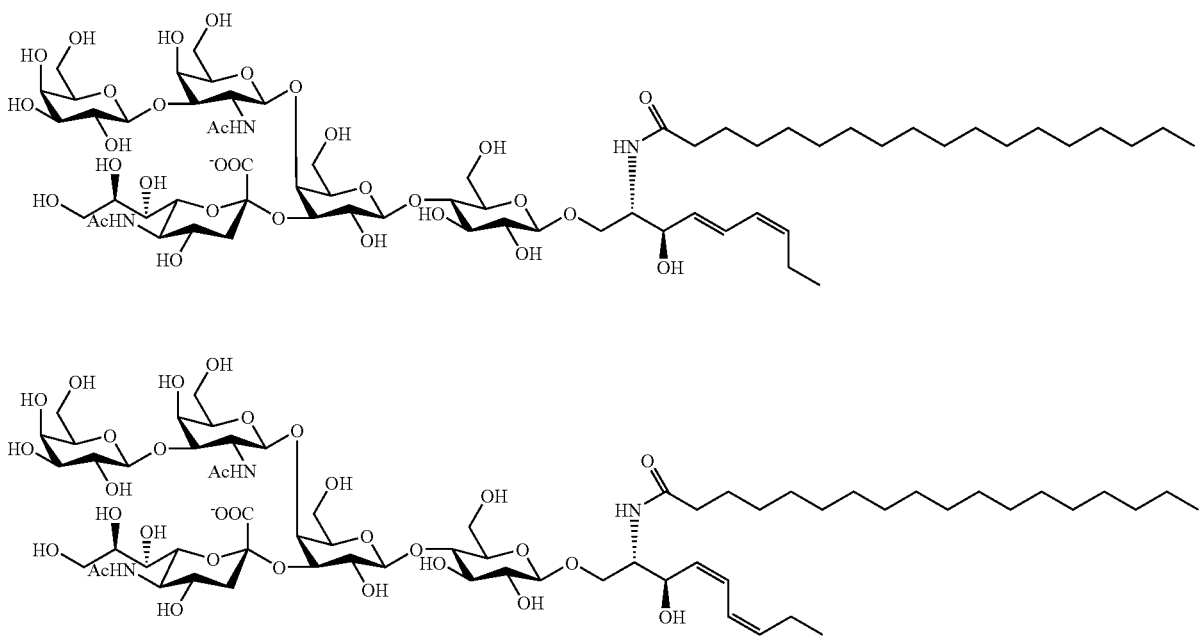

The Wittig procedure of Example 2 was followed except that the starting ylide was changed. The desired product was obtained as a solid (21% yield), as a 50/50 cis/trans mixture. ESI-MS; calcd for $C_{64}H_{111}N_3O_{31}$, 1417; found [M−1]⁻.

Example 5

Wittig Reaction Preparation of:

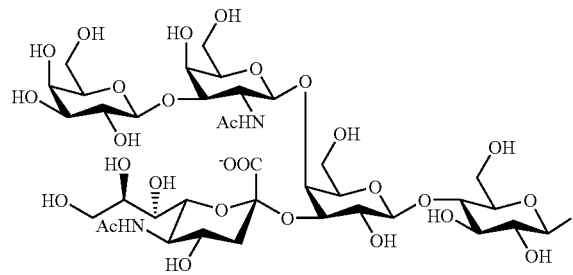

The Wittig procedure of Example 2 was followed except that the starting ylide was changed. The desired product was obtained as a solid (45% yield). ESI-MS; calcd for $C_{68}H_{109}ClN_6O_{31}$ 1540; found 1539[M−1]⁻. $^1$H-NMR (500 MHz, 95% DMSO-$d_6$+5% $D_2O$) δ8.00 (d, J 9.0 Hz, 2H), 7.50 (d, J 9.0 Hz, 2H), 4.80 (d, J 8.5 Hz, 1H), 4.26 (d, J 8.0 Hz), 4.22 (d, J 7.5 Hz, 1H), 4.19 (d, J 8.0 Hz, 1H), 3.05-4.00 (m), 2.02 (m, 2H), 1.87 (s, 3H, $COCH_3$), 1.75 (s, 3H, $COCH_3$), 1.21 (s), 0.83 (t, J 6.5 Hz, $CH_3$).

Example 6

Preparation of:

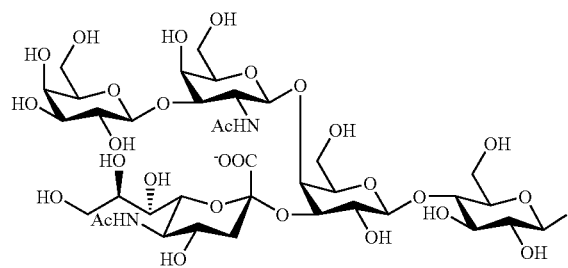

The $GM_1$ aldehyde (20 mg, 0.013 mmol) of Example 1 and dioctylamine (6 mg, 0.024 mmol), was added with stirring to 2.5 mL of dimethylformamide (DMF) at room temperature. Then trans-2-phenylvinylboronic acid (9 mg, 0.045 mmol) in methanol (5 mL) was added. The resulting solution was stirred at room temperature for three days. The reaction mixture was then concentrated to dryness on a rotovap and the residue purified by solid phase extraction using a 1 g HAX cartridge. The eluant was then purified using HPLC to afford 9.5 mg (43% yield) of white solid. ESI-MS; cacld for $C_{83}H_{144}N_4O_{31}$, 1693; found 1692 [M−1]⁻. $^1$H-NMR (500 MHz, 95% DMSO-$d_6$+5% $D_2O$) δ8.05 (d, J 3.0 Hz, 1H), 7.70 (m 5H), 6.40 (m, 1H), 6.25 (dd, J 9.0 and 16 Hz, 1H), 4.80 (d, J 8.5 Hz, 1H), 4.28 (d, J 8.0 Hz, 1H), 4.22 (d, J 8.0 Hz, 1H), 4.16 (d, 4.2 Hz, 1H), 3.00-4.00 (m), 2.10 (m, 2H), 1.86 (s, 3H, $COCH_3$), 1.60 (s, 3H, $COCH_3$), 1.19 (s), 0.83 (t, 3H, $CH_3$).

Example 7

MPTP/VMC Assay (in vitro) for Evaluation of Neuroprotective Efficacy

Ventral Mesophenthalic Cells (VMCs) were isolated from fetal rat brain stems (15 days old). Cells are cultured for several days (48 well plates) with controls on every plate.

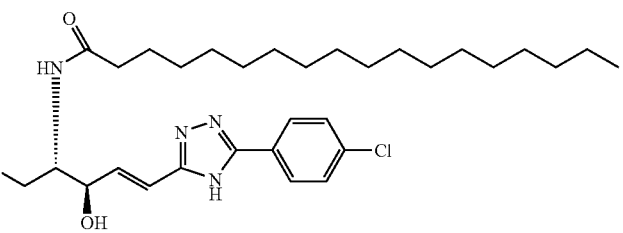

Cells are treated with 1-methyl-4-phenyl-1,2,3,6-tetrahydropyridine (PTP) (10 μM) for 24 hours which results in 30-50% cell death. Toxin is then removed. Cells are then treated with a compound of the invention in DMSO. After 24 hours, a tyrosine hydroxylase immuno-stain and cell count is performed.

The controls are MPTP (10 μM–30-50% cell kill) and $GM_1$ (30 μM) or LIGA-20 (10 μM)–30-50% protection.

NMDA Excitotoxicity

See, Dawson, et al., *Proc. Natl. Acad. Sci. USA* 88:7797 (1991). Stock solutions of 10 mm NMDA and 10 mm glycine

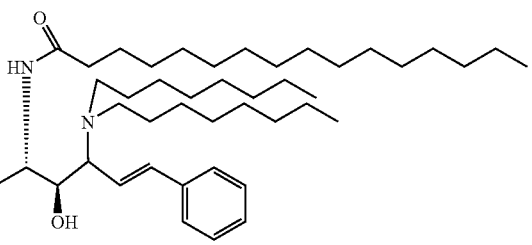

in sterile $H_2O$ are diluted to working concentrations of 500 M and 10 M respectively in control salt solution (CSS) without magnesium (120 mm NaCl, 5.4 mm KCl, 1.8 mm $CaCl_2$, 25 mm Tris-hydrocloride pH 7.4 at room temperature, 15 mm glucose). Cells are pretreated with glycosphingolipid mimetics for 3 days. The complete media is then carefully removed from the cells and gently washed with CSS without magnesium three times. A working solution of NMDA/glycine/CSS is added to the cells for 5 minutes, then promptly aspirated and replaced with CSS containing $MgCl_2$ (1 mM) to stop the reaction. Cells are then cultured in complete media with and without glycosphingolipid mimetics for another 20-24 hours and then assessed for appropriate incubator for cell survival (trypan blue exclusion and Hoescht/propidium iodide staining detailed below).

Example 8

Sialylation of Lyso-lactosyl Ceramide

This Example describes the reaction conditions for sialylation of lyso-lactosyl ceramide. Lactosylceramide was obtained from bovine buttermilk and the fatty acid moiety removed by base hydrolysis to form lyso-lactosyl ceramide. A mixture of the lyso-lactosyl ceramide (1.0 mg, 1.6 μmol) and CMP-sialic acid (2.46 mg, 65% purity, 2.40 μmol in HEPES buffer (200 mm, containing 8% MeOH, pH 7.5, 50 μL) was sonicated for twenty minutes. α2,3 sialyltransferase (10 μL, 5 U/mL, 50 mU) was then added followed by alkaline phosphatase (1 μL, $1.0 \times 10^5$ U/mL, 100 U). The reaction mixture was kept at room temperature. After one day, a further portion of α2,3 sialyltransferase (10 μL, 5 U/mL, 50 mU) was added. After four more days, an additional portion of α2,3 sialyltransferase (10 μL, 5 U/mL, 50 mU) was added. After an additional one day at room temperature, thin layer chromatography indicated that the reaction was nearly complete.

Example 9

Synthesis of GM2 from Lactosylceramide Obtained from Bovine Buttermilk

A schematic diagram of showing two pathways for synthesis of the ganglioside $GM_2$ from lactosylceramide obtained from bovine buttermilk is shown in FIG. 1. In the pathway shown at left, the fatty acid is not removed from the lactosylceramide prior to sialylation, and the reaction is not carried out in the presence of an organic solvent. The reaction at right, in contrast, is carried out in the presence of an organic solvent, and with removal of the fatty acid.

First, the fatty acid is hydrolyzed from the lactosylceramide by treatment with a base and water (Step 1). A sialic acid residue is then added by enzymatic transfer to the galactose residue using an α2,3 sialyltransferase, preferably an ST3GalIV (Step 2). This reaction can be carried out in the presence of an organic solvent. A GalNAc residue is then attached to the galactose in a β1,4 linkage using a GalNAc transferase (Step 3); this step may or may not be carried out in the presence of an organic solvent. Finally, the fatty acid moiety is reattached to the sphingosine to obtain the desired $GM_2$ ganglioside. The reaction typically proceeds nearly to completion due to the presence of an organic solvent during the sialylation.

Example 10

Synthesis of Glycosphingolipids from Plant Glucosyl Ceramide

This Example describes three alternative procedures for the synthesis of the $GM_2$ ganglioside using plant glucosylceramide as the precursor (FIG. 3). In Route 1, β1,4-galactosidase is used to catalyze the transfer of a Gal residue to the glycosylceramide. Simultaneously, an α2,3-sialyltransferase is used in a sialyltransferase cycle to link a sialic acid residue to the Gal. Next, a β1,4-GalNAc transferase is added to the reaction mixture, either with UDP-GalNAc or as part of a GalNAc transferase cycle. In this step, the GalNAc residue is linked to the Gal residue in an α2,3 linkage.

Route 2 differs from the synthesis shown in Route 1 in that the addition of the Gal to the glycosylceramide is catalyzed by a β1,4-galactosyltransferase enzyme, using either a galactosyltransferase cycle or TDP-Glc/Gal as the acceptor sugar. Sialylation and addition of GalNAc are carried out as described above to obtain $GM_2$.

In Route 3, the fatty acid is first removed by treatment with aqueous base prior to the glycosyltransferase steps. The galactosylation, sialylation, and GalNAc transferase reactions are carried out as in Route 2. Following the addition of the GalNAc residue, a fatty acid is linked to the molecule. The fatty acid can be the same as that originally found on the plant glucosylceramide, or can be different. In the example shown in FIG. 4, an activated $C_{18}$ fatty acid is used, resulting in the synthesis of $GM_2$. Greater efficiency is generally observed when the fatty acid is removed prior to the glycosylation reactions.

Example 11

Synthesis of Ganglioside $GM_2$ from Glycosylceramide

Figure 4:
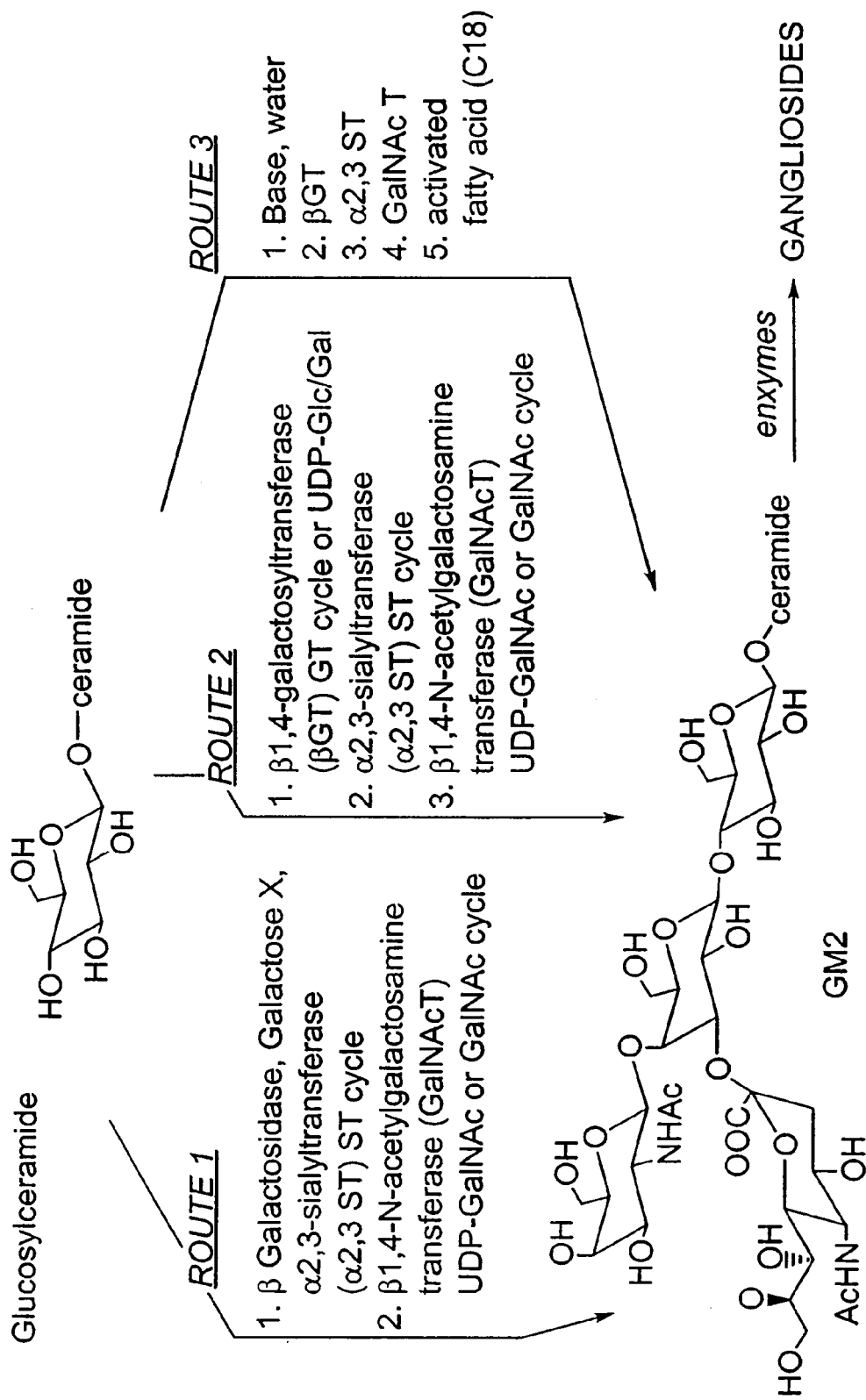
FIG. 4 is a collection of three routes for synthesizing GM2 and other gangliosides starting from a glucosylceramide.

This Example describes three alternative procedures for the synthesis of the $GM_2$ and other glycosphingolipids using a glucosylceramide as the precursor (FIG. 4). In Route 1, a β1,4-galactosidase is used to catalyze the transfer of a Gal residue to the glycosylceramide. Simultaneously, an α2,3-sialyltransferase is used in a sialyltransferase cycle to link a sialic acid residue to the Gal. Next, a β1,4-GalNAc transferase is added to the reaction mixture, either with UDP-GalNAc or as part of a GalNAc transferase cycle. In this step, the GalNAc residue is linked to the Gal residue in an α2,3 linkage.

Route 2 differs from the synthesis shown in Route 1 in that the addition of the Gal to the glycosylceramide is catalyzed by a β1,4-galactosyltransferase enzyme, using either a galactosyltransferase cycle or UDP-Glc/Gal as the acceptor sugar. Sialylation and addition of GalNAc are carried out as described above to obtain $GM_2$.

In Route 3, the fatty acid is first removed by treatment with aqueous base prior to the glycosyltransferase steps. The galactosylation, sialylation, and GalNAc transferase reactions are carried out as in Route 2. Following the addition of the GalNAc residue, a fatty acid is linked to the molecule. In the example shown in FIG. 3, an activated $C_{18}$ fatty acid is used, resulting in the synthesis of $GM_2$. Greater efficiency is generally observed when the fatty acid is removed prior to the glycosylation reactions.

After each synthetic route, additional glycosyltransferases can be used to add additional saccharide residues in order to obtain more complex glycosphingolipids.

Example 12

Effect of Compounds of the Invention on Growth of Mammalian Cells

Materials and Methods

Compounds 2, 8, 10, 13, 56, 57, 58, 59, 60, and 61 were made according to methods of the present invention and stored in powder form until use.

9L cells were obtained from Wake Forest University (Winston-Salem, N.C.) and the other five cell lines from American Type Culture Collection (ATCC, Manassas, Va.). Minimum essential medium Eagles (MEM) and basal medium Eagles (BME) media, fetal bovine serum (FBS), newborn bovine serum, and trypsin-EDTA solution were obtained from Sigma Chemical Co., St. Louis, Mo. Dulbecco's modified Eagle's medium (DMEM) and Liebovitz L-15 medium were obtained from ATCC (Manassas, Va.). MTT dye reagents were obtained from Promega Corporation, Madison, Wis.

Cell Culture 9L cells were grown in BME media with 10% newborn bovine serum, 2 mm glutamine, and 1% penicillin/streptomycin at 37° C. in 5% $CO_2$/95% air. The cell lines obtained from ATCC were grown in the ATCC-recommended medium at 37° C. in 5% $CO_2$/95% air. SK-N-MC (HTB-10) and U-87 (HTB-14) were grown in MEM with Earles salts, 2 mm glutamine, 1 mm pyruvate, 0.1 M non-essential amino acids (NEAA), and 10% FBS. U-118S (HTB-15) and Hs 683 (HTB-138) cells were grown in DMEM, 4 mm glutamine, 4.5 g/L glucose, 1.5 g/L sodium bicarbonate, and 10% FBS. SW 1088 (HTB-12) cells were grown in Liebovitz L-15 medium with 10% FBS in a humidified 37° C. air environment (no added $CO_2$). Medium for each cell line was changed every third day, and cells were passaged weekly using 0.25% trypsin-EDTA solution as the dissociation agent.

Proliferation Assay

Cells at 80% confluence were harvested using 0.25% trypsin-EDTA solution. The trypsinized cells were plated in 96-well plates at 2000 cells per well (with the exception of 9L cells, which were plated at 1200 cells per well, as they grow very fast). Working stocks of each of the ten compounds—2, 8, 10, 13, 56, 57, 58, 59, 60, and 61—were prepared in dimethyl sulfoxide (DMSO). After the cells were allowed to attach for 24 h, the cultures were fed and dosed with each of the ten compounds at concentrations of 0.05, 0.5, 5, and 50 µM. For each concentration, replicates of six wells were used. Controls received the same volume of DMSO diluted in medium that was added to the test wells. The culture medium was renewed with fresh test compound every three days. After seven days of culture, the viable cells were measured using MTT reagent. The MTT assay was performed by removing the medium from each well, adding 100 µL of fresh medium and 15 µL of tetrazolium dye solution to each well and incubating the cells at 37° C. for 4 h. After 4 h, 100 µL of solubilization/stop solution was added to each well. The plates were incubated at room temperature overnight, and the intensity of the yellow color of each well was measured at 575 mn on a Bio-Tek Instruments (Winooski, Vt.) microplate scanning spectrophotometer.

The results of the proliferation assay are provided in FIG. 6-FIG. 15.

Neurite Out Growth Assay

Dorsal root ganglia (DRG) neuronal cultures are established from Sprague-Dawley rats at embryonic age of 15 days (Harlan Inc., Indianapolis, Ind.) (see, Eldridge, et al., *J. Cell. Biol.* 105:1023-1034 1987)). Briefly, the embryos are dissected and the spinal cords isolated. The DRGs are then separated from the spinal cords and placed in CMF medium. The DRG neurons are then dissociated with 0.25% trysin and plated into 8-well chamber slides (Nalge Nunc, Chicago, Ill.) that were coated with rat tail collagen (Collaborative Biomedical Products, Bedford, Mass.). Glycosphingolipid is added in various concentrations from 1 µM to 100 µM. The neurite outgrowth is assessed by measuring the length of the neurite after 48 hours.

Example 13

Immunosupresion Assay

See, Bruunsgaard, et al., *Clin. Exp. Immnol.* 119(3):433 (2000).

Peripheral blood monocyte are isolated by Ficoll—Hypague (Pharmacia) density gradient centrifugation from heparinized (50 U/ml) blood (see, Boyum, et al., *Scand. J. Clin. Lab. Invest. Suppl.* 97:9-29 (1968)). Briefly, heparinized blood is gently laid on top of FICOLL (obtained from Pharmacia) (FICOLL to serum ratio 1:2) and then centrifuged at 1600 rpm for 25 minutes. The buffy coat is aspirated and washed two times and resuspended in RPMI 1640. Cells are cultured in RPMI 1640 with 10% fetal calf serum at the density of $2 \times 10^5$ cells per well in 96 well round-bottom microtiter plates containing 20 mg/mL phytohaemagglutinin for 24 hours with and without glycosphingolipid (1 to 100 µM. The proliferation of lymphocyte is assay be adding [$^3$H] TDR (1 µCi/well, 5 Ci/mmol) for 18 hours. The plates are then harvested and counted using a scintillation counter.

Example 14

Protection of Cortical Cells from Apoptosis

To induce apoptosis, mouse cortical cells were cultured and treated with 50 µM hydrogen peroxide for three hours prior to being treated with the ganglioside analogue. The cells were also treated with the hydrogen peroxide during treatment with the ganglioside analogue and post-treatment for 48 h. Cell death was assayed using the MTT assay.

Approximately 30% of the cells treated with hydrogen peroxide died as a result of the treatment. Treatment with Liga 20 (or GM1) (approx. 0.1 µM) provided approximately 20% protection of the cells from apoptosis. The compounds of the invention, at similar concentrations, provided approximately the same level of protection to the cells.

Example 15

Protection of Cortical Cells from Cell Death

To induce non-apoptotic cell death, mouse cortical cells were cultured and treated with 50 µM hydrogen peroxide and oligomycin (0.01 µM) for three hours prior to being treated with the ganglioside analogue. The cells were also treated with the hydrogen peroxide and oligomycin during treatment with the ganglioside analogue and post-treatment for 48 h. Cell death was assayed using the MTT assay.

Approximately 30% of the cells treated with hydrogen peroxide died as a result of the treatment. Treatment of the cells with the compounds of the invention protected approximately 20% protection of the cells from death.

Example 16

Rescue of Striatal Dopamine Levels in MPTP-Treated Mice

Male C57B1/6 mice 7-8 weeks of age were treated with MPTP (b.i.d., 20 mg/kg, s.c.). The mice also received a daily administration of saline, GM1 (30 mg/kg), a compound of the invention (0.3. 3 mg/kg, i.p. and 30 mg/kg os) fpr three weeks starting 24 h after the last MPTP injection. The brains were removed and analyzed for striatal dopamine levels. The midbrain was fixed for TH immunohistochemistry and dopamine neuron cell counts.

MPTP alone caused approximately 76% loss of striatal dopamine. GMa and compounds of the invention (at all doses and routes of administration) increased striatal dopamine levels to approximately the same extent.

It is understood that the foregoing discussion and examples present a detailed description of certain preferred embodiments of the present invention. It will be apparent to those of ordinary skill in the art that various modifications and equivalents can be made without departing from the spirit and scope of the invention. All the patents, journal articles and other documents discussed or cited above are herein incorporated in their entirety by reference for all purposes.

What is claimed is:

1. A compound having the formula:

Saccharide—Z—CH(X)—CH(Y)—C(R$^{12}$)=C(R$^{11}$)—C(O)R$^{13}$ wherein

Z is a member selected from O, S, C(R$^2$)$_2$ and NR$^2$;

X is a member selected from H, —OR$^3$, —NR$^3$R$^4$, —SR$^3$, and —CHR$^3$R$^4$;

R$^2$, R$^3$ and R$^4$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, —C(=M)R$^5$, —C(=M)—Z—R$^5$, —SO$_2$R$^5$, and —SO$_3$;

wherein

M and Z are members independently selected from O, NR$^6$ and S;

Y is a member selected from H, —OR$^7$, —SR$^7$, —NR$^7$R$^8$, substituted or unsubstituted alkyl, substituted or unsubstituted heteroalkyl, substituted or unsubstituted aryl, substituted or unsubstituted heteroaryl, and substituted or unsubstituted heterocycloalkyl wherein R$^5$, R$^6$, R$^7$ and R$^8$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl;

R$^{11}$ and R$^{12}$ are members independently selected from substituted or unsubstituted alkyl, substituted or unsubstituted heteroalkyl, substituted or unsubstituted aryl, substituted or unsubstituted heteroaryl, substituted or unsubstituted heterocycloalkyl, NR$^{14}$R$^{15}$, OR$^{14}$, —CN and —C(=L)R$^{14}$;

wherein

L is a member selected from O, S, and NR$^{16}$;

R$^{13}$ is selected from substituted or unsubstituted heterocycloalkyl, OR$^{17}$ and NR$^{17}$R$^{18}$; and R$^{14}$ and R$^{15}$ is selected from H, substituted or unsubstituted alkyl, substituted or unsubstituted heteroalkyl, substituted or unsubstituted aryl, substituted or unsubstituted heteroaryl, substituted or unsubstituted heterocycloalkyl, C(O)R$^{17}$, OR$^{17}$ and NR$^{17}$R$^{18}$;

wherein

R$^{16}$, R$^{17}$ and R$^{18}$ are members independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl.

2. The compound according to claim 1, wherein the saccharide has a formula that is selected from the group consisting of:

GalNAc-Gal-Glc—| with NANA branch;
Gal-Glc—| with NANA branch;
Gal-GalNAc-Gal-Glc—| with NANA branch; and
Gal-GalNAc-Gal-Glc—| with NANA branch.

wherein NANA is N-acetyl neuraminic acid.

3. The compound according to claim 1, wherein the saccharide is deacetylated.

4. The compound of claim 1, having the formula:

Saccharide—Z—CH(X)—CH(Y)—C(R$^{12}$)=C(R$^{11}$)—C(O)NR$^{17}$R$^{18}$ wherein at least one of R$^{17}$ and R$^{18}$ is selected from the group consisting of substituted or unsubstituted aryl and substituted or unsubstituted heteroaryl.

5. A compound having a formula which is a member selected from FIG. 16.

6. A pharmaceutical composition comprising the compound of claim 1 and a pharmaceutically acceptable carrier.

7. A compound selected from the group consisting of:

[Structure of a complex glycolipid compound with sialic acid, galactose, N-acetylgalactosamine, glucose moieties linked to a ceramide-like backbone bearing a long acyl chain and a brominated dimethoxyphenethyl amide group]

-continued
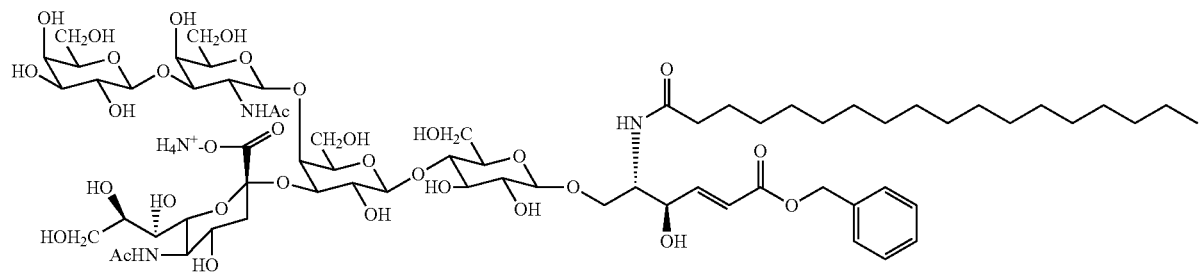
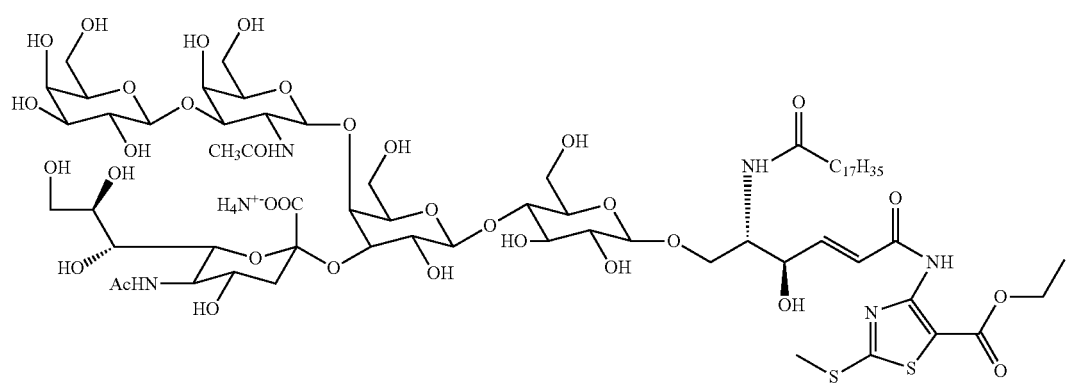
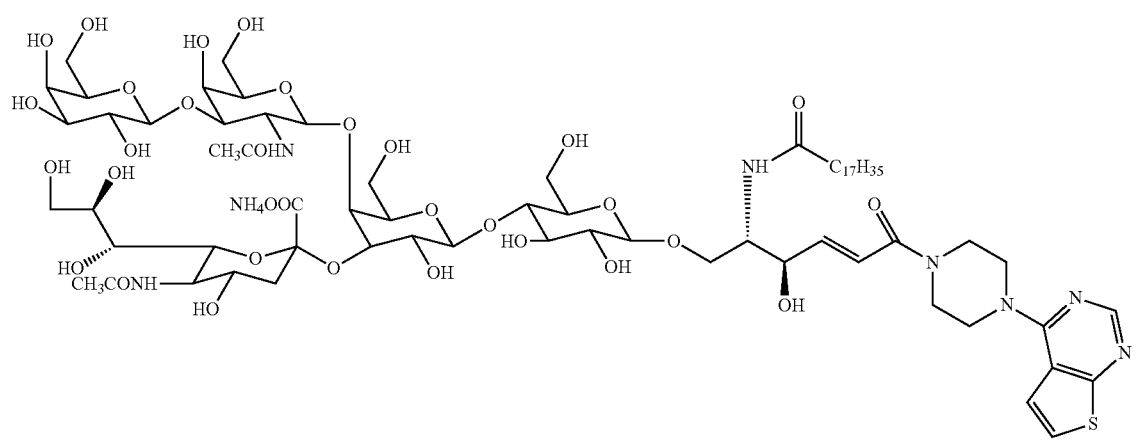
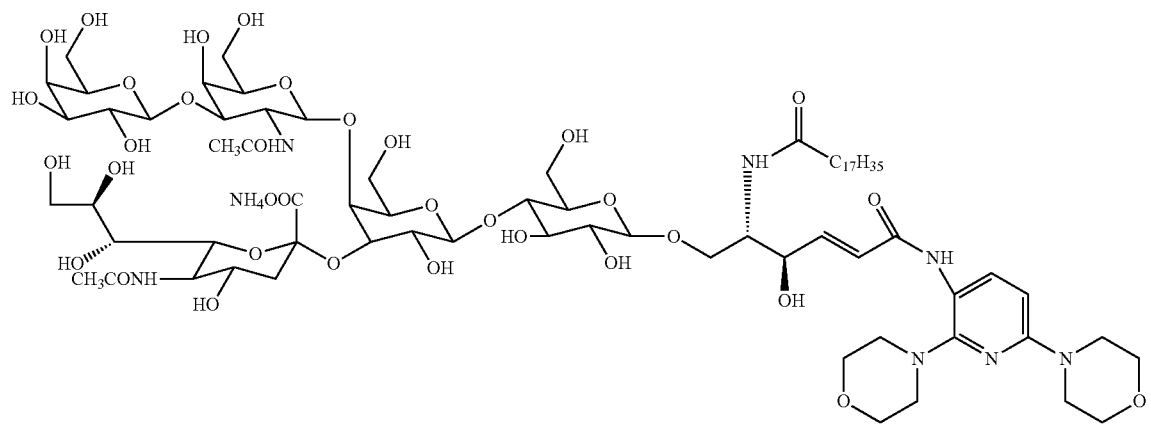

-continued
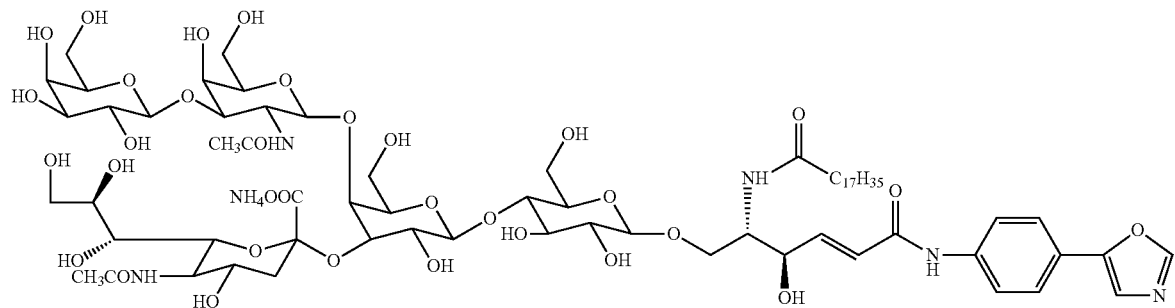
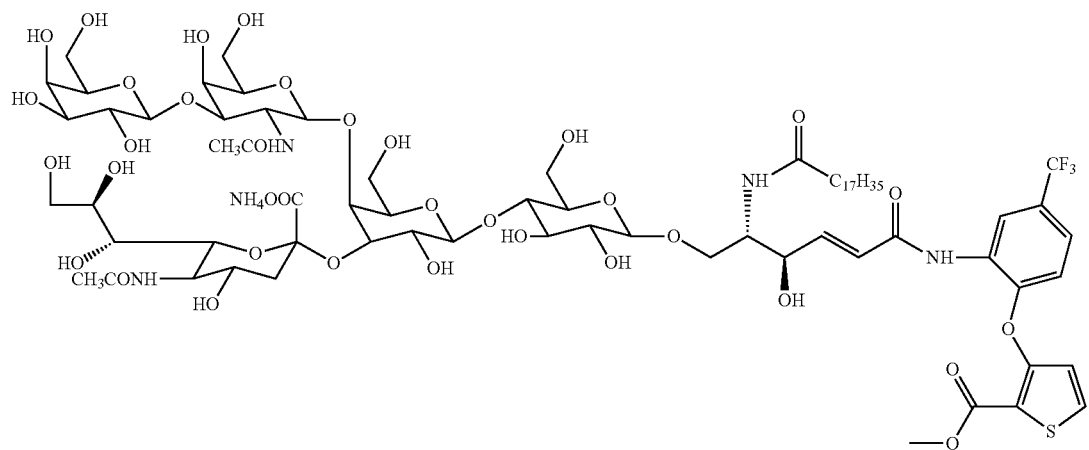
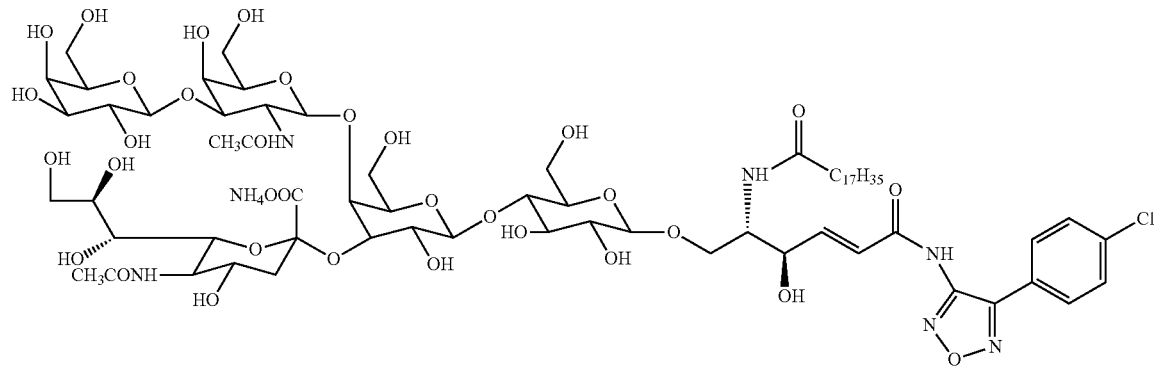
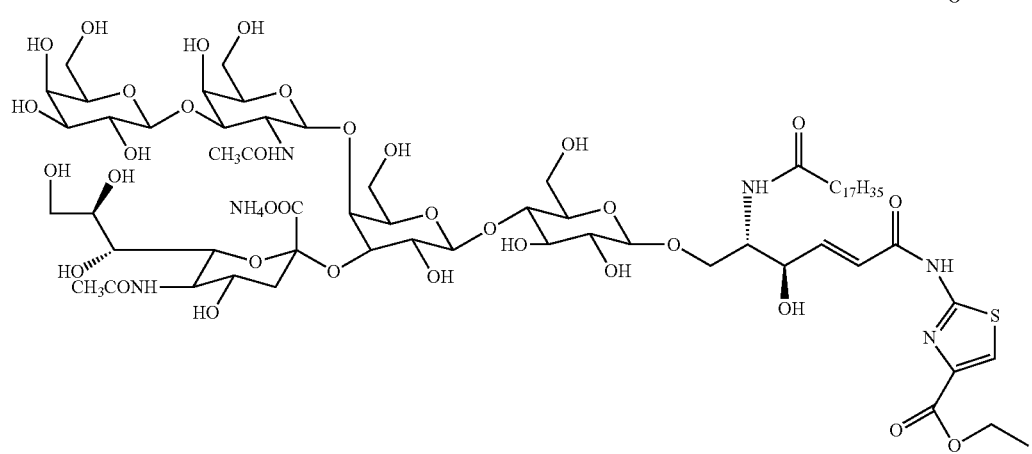

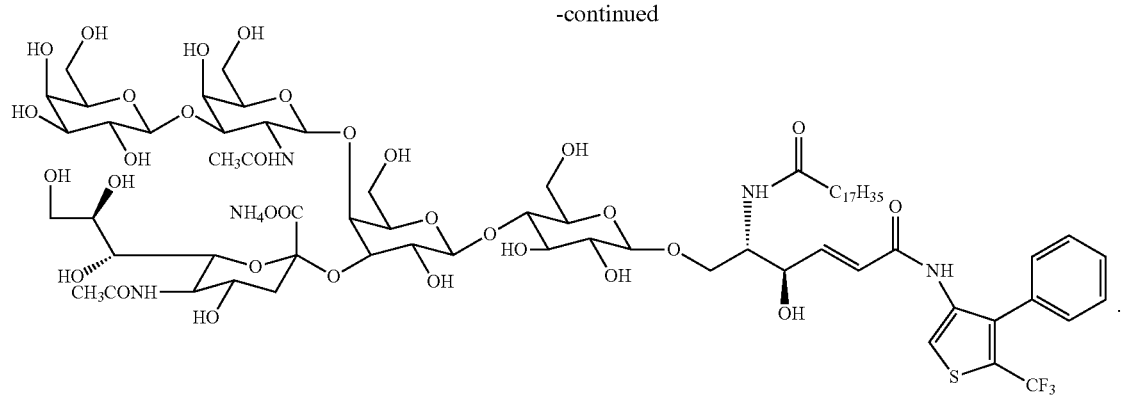
8. The compound of claim 5, having a formula which is a member selected from FIG. 16G-16U.
9. A pharmaceutical composition comprising the compound of claim 5 and a pharmaceutically acceptable carrier.
10. A method for the treatment of a glioma in a human comprising the step of administering to the human in need thereof a therapeutically effective amount of the compound claim 7.
* * * * *